United States Patent
Gazit et al.

(10) Patent No.: US 9,381,273 B2
(45) Date of Patent: Jul. 5, 2016

(54) SCAFFOLDS WITH OXYGEN CARRIERS, AND THEIR USE IN TISSUE REGENERATION

(75) Inventors: Dan Gazit, Maccabim (IL); Gadi Pelled, Rishon-LeZion (IL); Zulma Gazit, Maccabim (IL); Nadav Kimelman-Bleich, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 714 days.

(21) Appl. No.: 12/320,594

(22) Filed: Jan. 29, 2009

(65) Prior Publication Data
US 2009/0214649 A1 Aug. 27, 2009

Related U.S. Application Data

(60) Provisional application No. 61/025,135, filed on Jan. 31, 2008.

(51) Int. Cl.
| | | |
|---|---|---|
| *A61L 27/38* | (2006.01) | |
| *A61L 27/22* | (2006.01) | |
| *A61L 27/36* | (2006.01) | |
| *A61L 27/52* | (2006.01) | |
| *A61L 27/56* | (2006.01) | |

(52) U.S. Cl.
CPC ........... *A61L 27/3843* (2013.01); *A61L 27/225* (2013.01); *A61L 27/3604* (2013.01); *A61L 27/3834* (2013.01); *A61L 27/52* (2013.01); *A61L 27/56* (2013.01)

(58) Field of Classification Search
CPC . A61L 27/3843; A61L 27/3834; A61L 27/56; A61L 27/52
See application file for complete search history.

(56) References Cited

U.S. PATENT DOCUMENTS

| | | | | |
|---|---|---|---|---|
| 6,635,267 | B1* | 10/2003 | Miyoshi et al. | 424/422 |
| 6,835,377 | B2* | 12/2004 | Goldberg et al. | 424/93.7 |
| 7,335,646 | B2* | 2/2008 | Kieffer et al. | 514/44 R |
| 7,790,678 | B1* | 9/2010 | Girsh | 514/17.1 |
| 2004/0115176 | A1* | 6/2004 | Swartz et al. | 424/93.7 |
| 2004/0203146 | A1* | 10/2004 | Gazit et al. | 435/399 |
| 2009/0017092 | A1 | 1/2009 | Dutta et al. | |

FOREIGN PATENT DOCUMENTS

WO WO 01/76507 10/2001

OTHER PUBLICATIONS

Gorden et al. Biotechnol. Prog. 21:1700-1707, 2005.*
Sen Wound Repair Regen 17(1):1-18, 2009.*
Chin et al. "Hydrogel-Perfluorocarbon Composite Scaffold Promotes Oxygen Transport to Immobilized Cells", Biotechnology Progress, 24(2): 358-366, 2008.
D'Ippolito et al. "Low Oxygen Tension Inhibits Osteogenic Differentiation and Enhances Stmness of Human MIAMI Cells", Bone, 39: 513-522, 2006.
Fraker et al. "Enhanced Oxygenation Promotes Beta-Cell Differentiation In Vitro", Stem Cells, 25: 3155-3164, 2007.
Grayson et al. "Effects of Hypoxia on Human Mesenchymal Stem Cell Expansion and Plasticity in 3D Constructs", Journal of Cellular Physiology, 207: 331-339, 2006.
Huang et al. "Combined Angiogenic and Osteogenic Factor Delivery Enhances Bone Marrow Stromal Cell-Driven Bone Regeneration", Journal of Bone and Mineral Research, 20(5): 848-857, 2005.
Khattak et al. "Enhancing Oxygen Tension and Cellular Function in Alginate Cell Encapsulation Devices Through the Use of Perfluorocarbons", Biotechnology and Bioengineering, 96(1): 156-166, Jan. 1, 2007.
Klöpper et al. "High Efficient. Adenoviral-Mediated VEGF and Ang-1 Gene Delivery into Osteogenically Differentiated Human Mesenchymal Stem Cells", Microvascular Research, 75: 83-90, 2008.
Martin-Rendon et al. "Transcriptional Profiling of Human Cord Blood CD133+ and Cultured Bone Marrow Mesenchymal Stem Cells in Response to Hypoxia", Stem Cells, 25: 1003-1012, 2007.
Moutsatsos et al. "Exogenously Regulated Stem Cell-Mediated Gene Therapy for Bone Regeneration", Molecular Therapy, 3(4): 449-461, Apr. 2001.
Muhonen et al. "Osteoblastic Activity and Neoangiogenesis in Distracted Bone of Irradiated Rabbit Mandible With or Without Hyperbaric Oxygen Treatment", International Journal of Oral & Maxillofacial Surgery, 33: 173-178, 2004.
Radisic et al. "Biomimetic Approach to Cardiac Tissue Engineering: Oxygen Carriers and Channeled Scaffolds", Tissue Engineering, 12(8): 2077-2091, 2006.
Radisic et al. "Cardiac Tissue Engineering Using Perfusion Bioreactor Systems", Nature Protocols, 3(4): 719-738, 2008.
Radisic et al. "Mathematical Model of Oxygen Distribution in Engineered Cardiac Tissue With Parallel Channel Array Perfused With Culture Medium Containing Oxygen Carriers", American Journal of Physiology, AJP—Heart and Circulatory Physiology, 288: H1278-H1289, 2005.
Response Dated Oct. 25, 2010 to Official Action of Sep. 29, 2010 From the US Patent and Trademark Office Re. U.S. Appl. No. 12/320,594.
Potier et al. "Hypoxia Affects Mesenchymal Stromal Cell Osteogenic Differentiation and Angiogenic Factor Expression", Bone, 40(4): 1078-1087, Apr. 2007.
Klöpper et al. "High Efficient Adenoviral-Mediated VEGF and Ang-1 Gene Delivery Into Osteogenically Differentiated Human Mesenchymal Stem Cells", Microvascular Research, 75: 83-90, 2008.

* cited by examiner

*Primary Examiner* — Marcia S Noble

(57) ABSTRACT

Provided are fibrin or silk matrices comprising an oxygen carrier, and matrices, which comprise an oxygen carrier and mesenchymal stem cells. Also provided are methods of generating and using same for ex vivo or in vivo tissue regeneration and/or repair such as for treating a non-union bone fracture and a condition requiring spinal fusion.

19 Claims, 17 Drawing Sheets
(7 of 17 Drawing Sheet(s) Filed in Color)

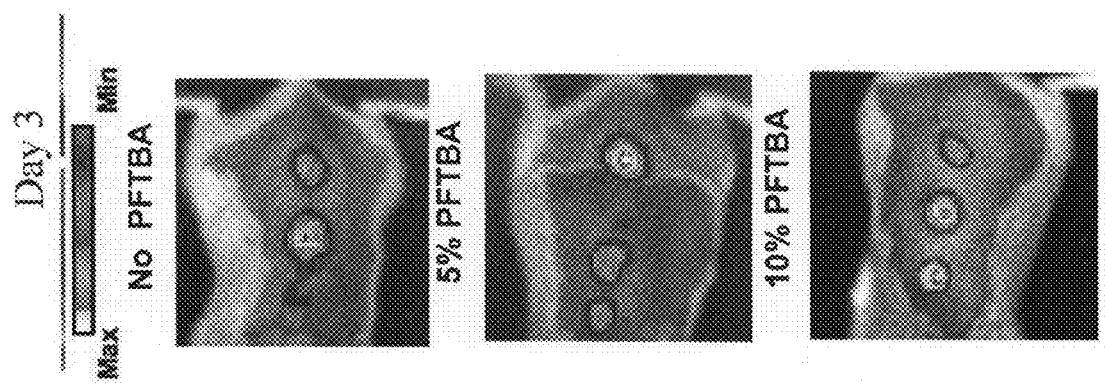

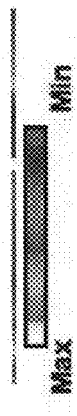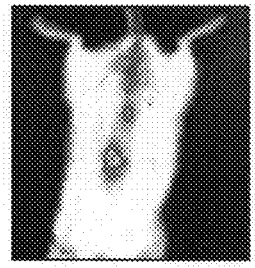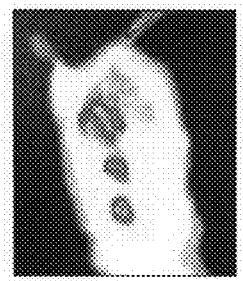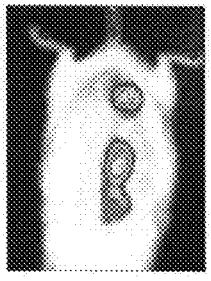
FIG. 3B
FIG. 3C
FIG. 3D

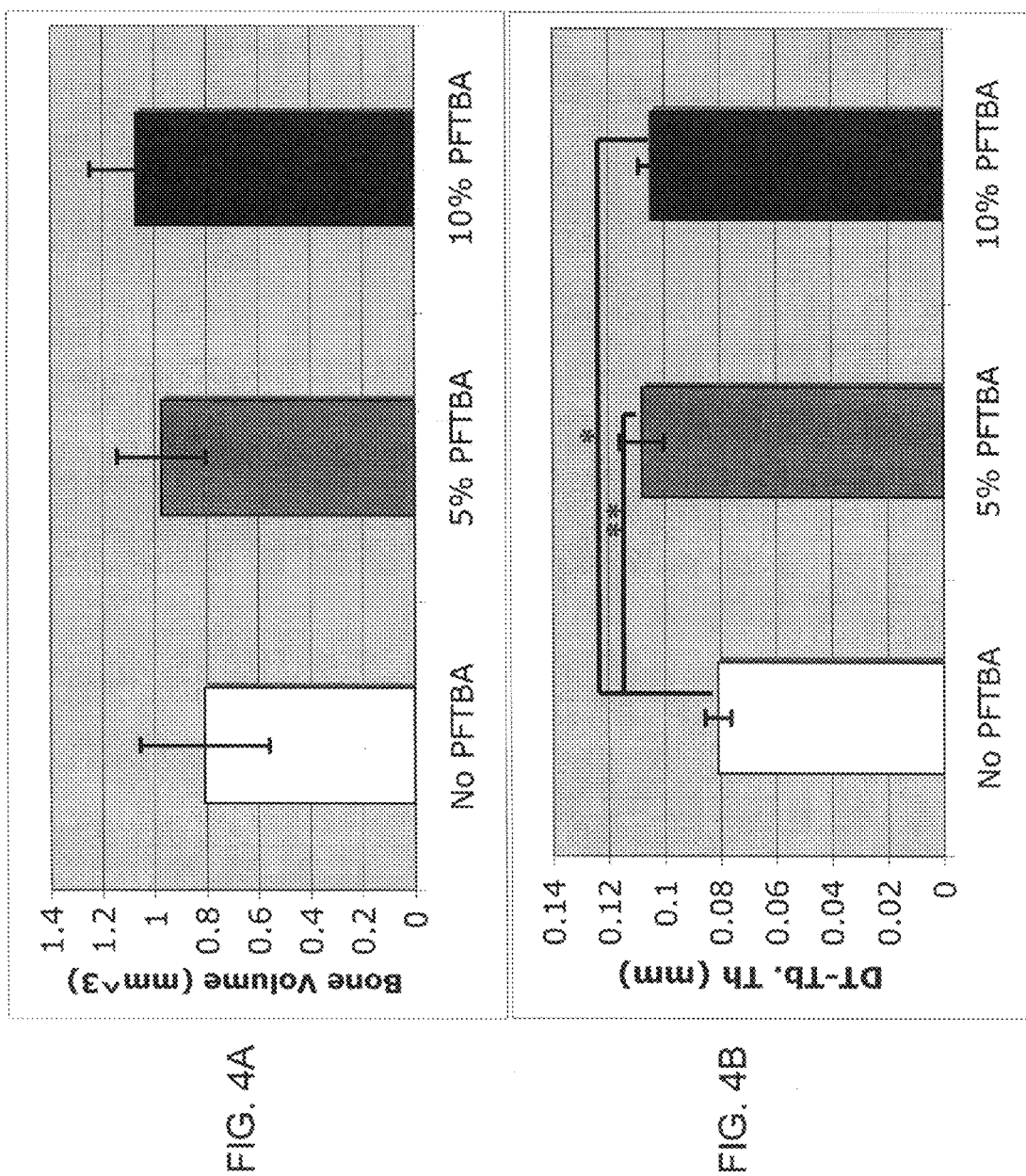

3 weeks      6 weeks

SCAFFOLDS WITH OXYGEN CARRIERS, AND THEIR USE IN TISSUE REGENERATION

RELATED APPLICATION

This application claims priority from U.S. Provisional Patent Application No. 61/025,135, filed Jan. 31, 2008, the teachings of which are fully incorporated herein.

FIELD AND BACKGROUND OF THE INVENTION

The present invention, in some embodiments thereof, relates to matrices which comprise oxygen carriers and methods of generating and using same for tissue formation, regeneration and/or repair.

Mesenchymal stem cells (MSCs) are multipotential stem cells, which can differentiate into the osteogenic, adipogenic, chondrogenic and tenogenic lineages. These cells can be isolated from bone marrow, adipose tissue, muscle tissue, umbilical cord blood and peripheral blood. Genetically engineered—MSCs, which over express osteogenic genes, such as bone morphogenetic proteins (BMP) can promote differentiation of cells into the osteogenic lineage in an autocrine or paracrine manner. BMPs are members of the transforming growth factor beta (TGFβ) superfamily and are known for their ability to induce bone formation in ectopic and orthotropic sites. Recent studies have shown that BMP-2, -6, -7 and -9 are potent inducers of osteogenic differentiation.

In vitro studies, which tested the effect of low oxygen levels on MSCs from various tissue sources, showed that while adipose-derived MSCs grown in culture dish under low oxygen level demonstrate inhibition of osteogenic differentiation (Malladi, Xu et al. 2006), bone marrow-derived MSCs cultured under hypoxic conditions show higher levels of osteoblastic and adipocyte markers (Grayson, Zhao et al. 2006). In addition, bone marrow-derived MSCs, which were subjected to short exposures of hypoxic conditions, exhibit no alterations in the level of osteogenic differentiation as determined by transcriptional profiles (Martin-Rendon, Hale et al. 2006). Yet, multipotential human stromal cells isolated from vertebrae bone marrow exhibit decreased osteogenic differentiation under low oxygen tension of 3% (D'Ippolito, Diabira et al. 2006).

One of the major hurdles in bone tissue engineering is the lack of oxygen supply to the forming tissue resulting in cell death and probably loss or delay of the osteogenic potential. Hyperbaric oxygenation therapy that elevates oxygen levels in tissues was found to increase osteoblastic activity and to accelerate bone formation induced by recombinant human BMP-2 protein (Muhonen, A., et al., 2004, Int. J. Oral Maxillofac Surg 33, 173-178).

Attempts to induce blood vessels formation in the forming bone tissue, mainly by using vascular endothelial growth factor (VEGF) have been reported (Huang, YC., et al., 2005, J. Bone Miner. Res. 20: 848-857; Klopper, J., et al., 2008, Microvasc. Res. 75: 83-90).

Khattak et al. (Biotechnology and Bioengineering, 96: 156-166, 2007) describe the use of alginate gels containing perfluorocarbons such as perfluorotributylamine (PFTBA) and perfluorooctylbromide (PFOB) for increasing oxygen availability and HepG2 cell viability.

WO 01/76507 describes the use of a serum-free aqueous medium comprising an oxygen carrier such as perfluorocarbons for transplantation of stem cells into vertebrate central nervous system for the treatment of neurodegenerative diseases.

Radisic et al. [Nat Protoc 3, 719, 2008; Tissue Eng 12, 2077, 2006; Am J Physiol Heart Circ Physiol 288, H1278, 2005] found that perfluorocarbons—supplemented medium enhances oxygen transport and cell viability of cardiomyocytes and fibroblasts cultured on a highly porous elastomer with a parallel array of channels.

Fraker et al. 2007 (Stem cells 25: 3155-3164) describes the use of the two-dimensional perfluorocarbon-silicone membrane for culturing of pancreatic buds.

Additional background art includes Chin K, et al., 2008 [Biotechnol. Prog. 24(2):358-66. Epub 2008 Feb. 23].

SUMMARY OF THE INVENTION

According to an aspect of some embodiments of the present invention there is provided a matrix comprising a fibrin backbone and an oxygen carrier.

According to an aspect of some embodiments of the present invention there is provided a matrix comprising a silk backbone and an oxygen carrier.

According to an aspect of some embodiments of the present invention there is provided a matrix comprising an oxygen carrier and mesenchymal stem cells.

According to an aspect of some embodiments of the present invention there is provided a method of generating a tissue, comprising: (a) providing the matrix of the invention; and (b) seeding the matrix with cells, thereby generating the tissue.

According to an aspect of some embodiments of the present invention there is provided a method of generating a connective tissue ex vivo, comprising: (a) providing the matrix of the invention, and; (b) culturing the cells under conditions which allow connective tissue formation, thereby generating the connective tissue ex vivo.

According to an aspect of some embodiments of the present invention there is provided a method of treating a subject having a diseased, damaged or loss of tissue, comprising implanting the tissue generated according to the method of the invention in the subject, thereby treating the subject having the diseased, damaged or loss of tissue.

According to an aspect of some embodiments of the present invention there is provided a method of treating a subject having a diseased, damaged or loss of connective tissue, comprising implanting the connective tissue generated according to the method of the invention in the subject, thereby treating the subject having the diseased, damaged or loss of connective tissue.

According to an aspect of some embodiments of the present invention there is provided a method of inducing in vivo tissue regeneration and/or repair, comprising implanting the matrix of the invention in a subject in need thereof, thereby inducing the in vivo tissue regeneration and/or repair.

According to some embodiments of the invention, the matrix further comprising cells.

According to some embodiments of the invention, the cells comprise mesenchymal stem cells.

According to some embodiments of the invention, the matrix is a continuous matrix having a volume at least of a cubic centimeter (cm) range.

According to some embodiments of the invention, the oxygen carrier is embedded within the backbone so that the oxygen carrier is unable to flow through, in or on the backbone.

According to some embodiments of the invention, the matrix comprises a plurality of pores.

According to some embodiments of the invention, the oxygen carrier comprises perfluorocarbon.

According to some embodiments of the invention, the perfluorocarbon comprises perfluorotributylamine (PFTBA).

According to some embodiments of the invention, a concentration of the perfluorocarbon in the matrix is at least about 1% weight per volume (w/v).

According to some embodiments of the invention, a concentration of the perfluorocarbon in the matrix is at least about 5% weight per volume (w/v).

According to some embodiments of the invention, a concentration of the perfluorocarbon in the matrix is at least about 10% weight per volume (w/v).

According to some embodiments of the invention, a concentration of the perfluorocarbon in the matrix is at least about 20% weight per volume (w/v).

According to some embodiments of the invention, the matrix is a hydrogel matrix.

According to some embodiments of the invention, the cells are genetically modified.

According to some embodiments of the invention, the cells exogenously express morphogenetic proteins (BMP).

According to some embodiments of the invention, the matrix further comprises a fibrin backbone.

According to some embodiments of the invention, the matrix further comprises thrombin.

According to some embodiments of the invention, the matrix further comprises a silk backbone.

According to some embodiments of the invention, the oxygen carrier is embedded within a backbone of the matrix so that the oxygen carrier is unable to flow through, in or on the backbone.

According to some embodiments of the invention, the tissue comprises a connective tissue.

According to some embodiments of the invention, the conditions enable proliferation and/or differentiation of the mesenchymal stem cells into the connective tissue.

According to some embodiments of the invention, the connective tissue comprises a bone tissue.

According to some embodiments of the invention, the subject suffers from or is diagnosed with a pathology selected from the group consisting of bone fracture, bone cancer, critical size bone defect, non-union bone fracture, osteoporosis, periodontal disease, periodontal defect, osteolytic bone disease, vertebral fracture, tendon tissue tear, ligament tissue tear, loss of cartilage, injured cartilage, osteoarthritis, diseased intervertebral disc tissue, loss of intervertebral disc tissue, injured intervertebral disc tissue, articular cartilage defect, injured muscle, burn and wound.

According to some embodiments of the invention, the cells exogenously express a SMAD polynucleotide.

According to some embodiments of the invention, the cells exogenously express a Brachyury (T-Box 1) polynucleotide.

According to some embodiments of the invention, the cells exogenously co-express a SMAD polynucleotide and a BMP polynucleotide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
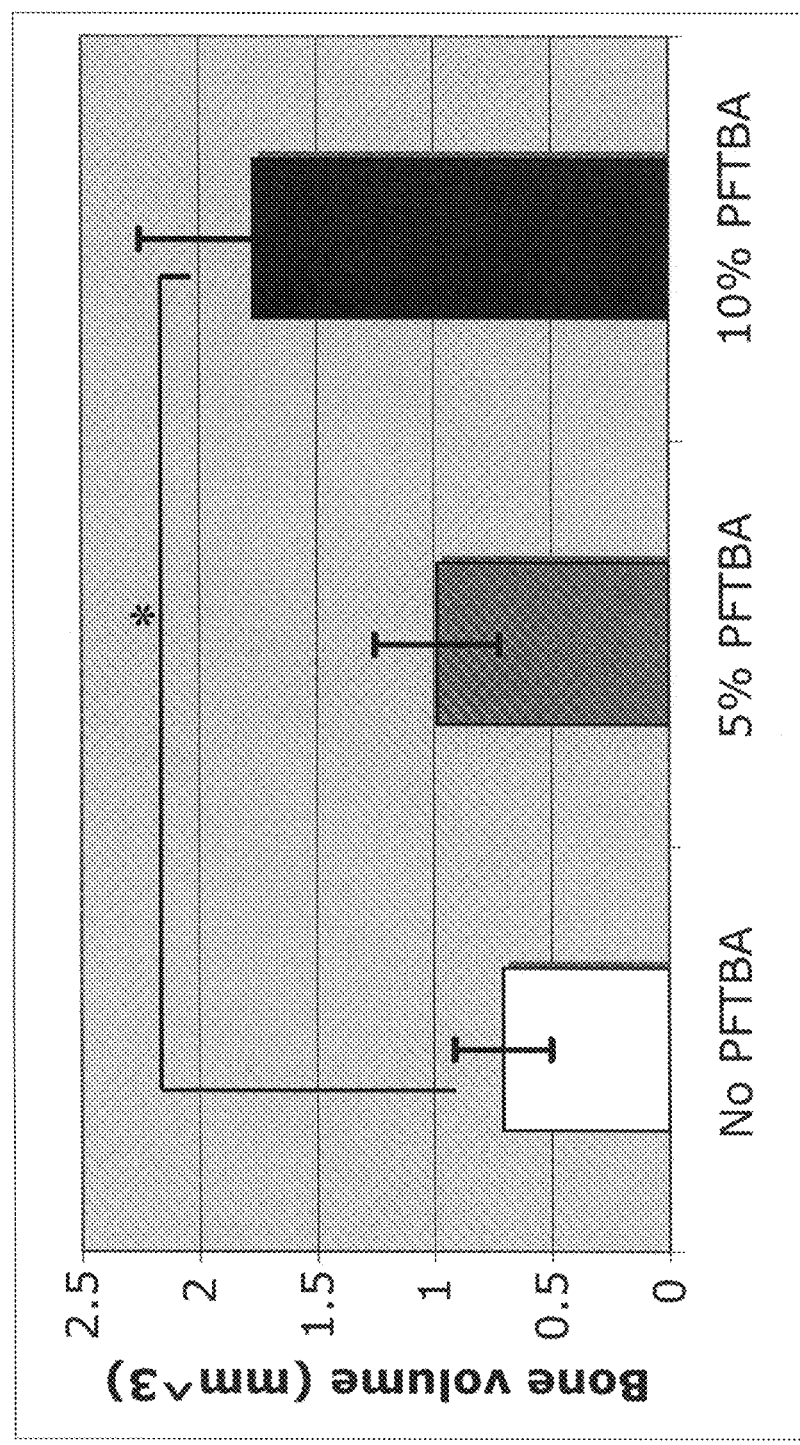
Figure 1B:
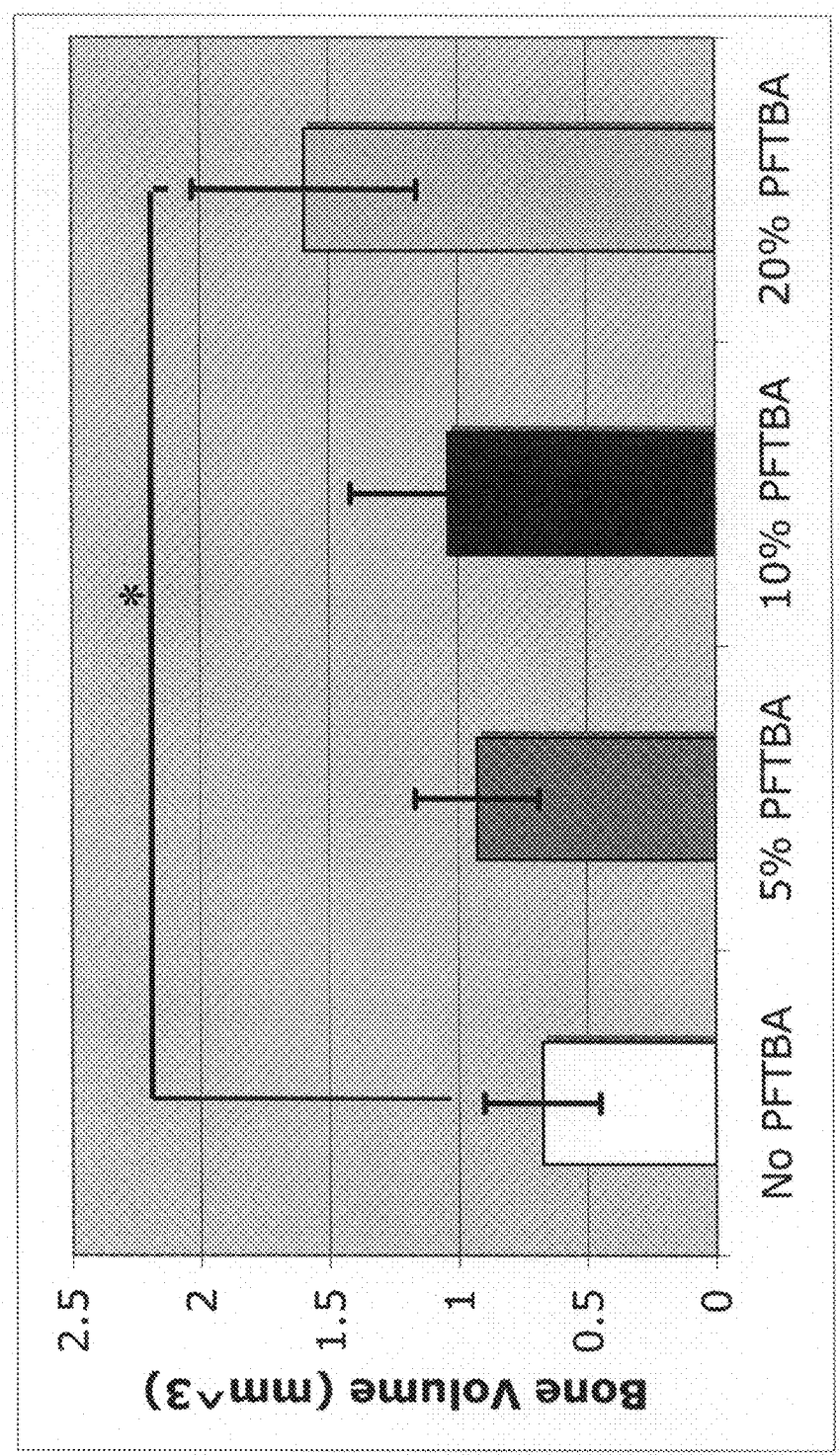
Figures 1C, 1D, 1E:
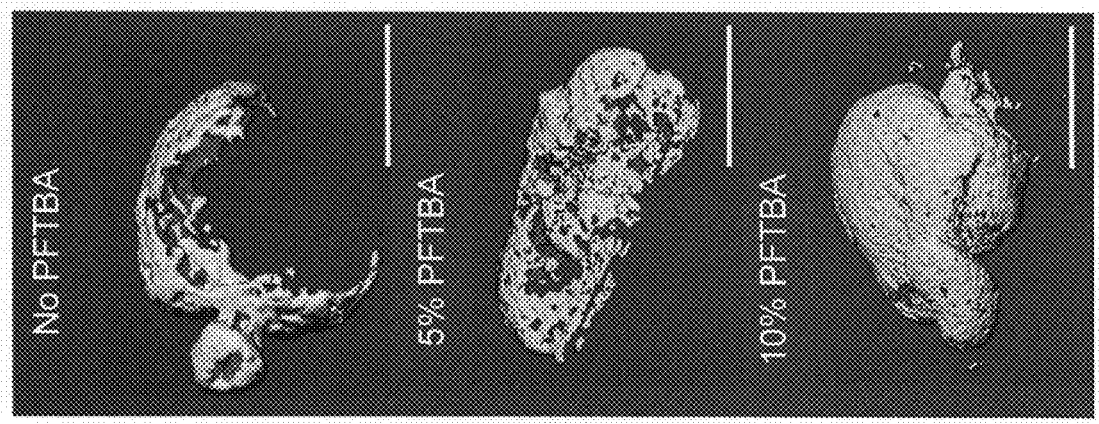
Figures 1F, 1G, 1H, 1I:
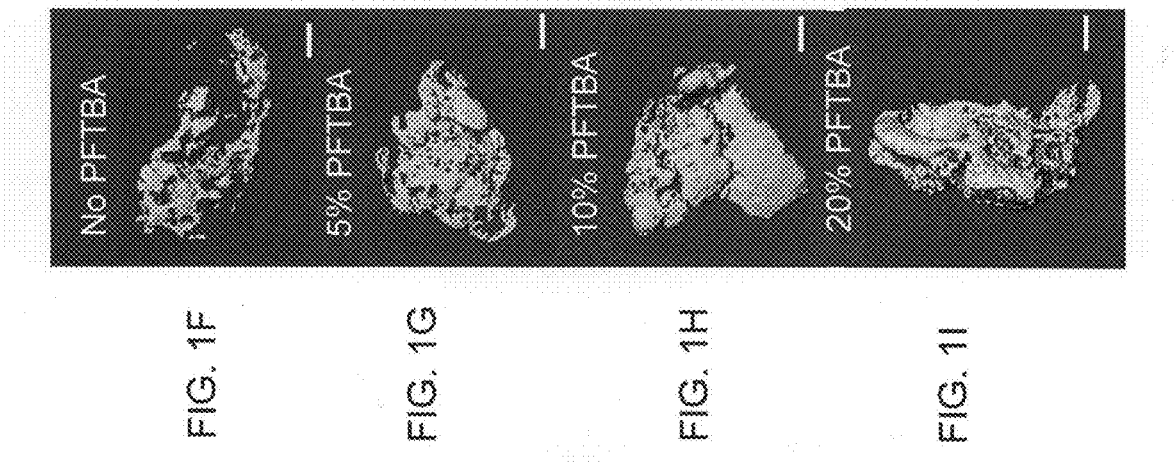
Figures 1J, 1K, 1L:
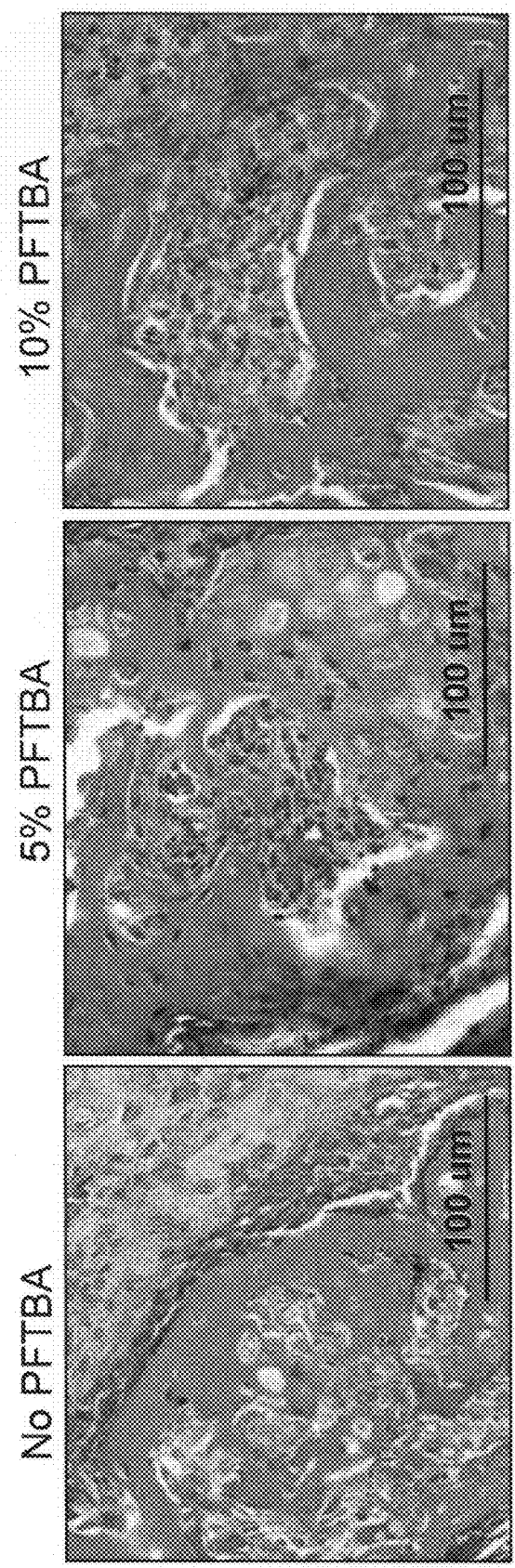

FIGS. 1A-L depict the effect of PFTBA on ectopic bone formation. One million Tet-off BMP2 MSCs [MSCs stably transfected with a BMP2 plasmid controlled by a tet-off expression system, as described in: Moutsatsos I K, Turgeman G, Zhou S, Kurkalli B G, Pelled G, Tzur L, Kelley P, Stumm N, Mi S, Müller R, Zilberman Y, Gazit D. Exogenously regulated stem cell-mediated gene therapy for bone regeneration. Mol Ther. 2001 April; 3(4):449-61] were suspended in fibrin or silk hydrogels supplemented with increasing concentrations of PFTBA [0, 5 or 10%, weight per volume (w/v) in fibrin hydrogels; and 0, 5, 10 and 20% (w/v) in silk hydrogels]. The gels were subcutaneously (SC) implanted in C3H/HeN mice and two weeks after SC implantation the implants were harvested and bone formation was analyzed using micro-computed tomography (micro CT). FIG. 1A-A histogram depicting analysis of bone volume ($mm^3$) in the ectopic bone formed by implantation of fibrin gels (which include MSCs) as a function of PFTBA content in the gel. White bar: no PFTBA (0% w/v PFTBA) in the fibrin gel; grey bar: 5% (w/v) PFTBA in the fibrin gel; black bar: 10% (w/v) PFTBA in the fibrin gel. Note that supplementation with PFTBA significantly enhances bone formation [P=0.045, 2-tailed T-test; n=16 implants in 5 mice for no-PFTBA (0% PFTBA) and 5% PFTBA groups, and 15 implants in 5 mice for the 10% PFTBA group]. FIG. 1B-A histogram depicting analysis of bone volume ($mm^3$) in the ectopic bone formed by implantation of silk gels (which include MSCs) as a function of PFTBA content in the gel. White bar: no PFTBA [0% (w/v) PFTBA) in the silk gel; grey bar: 5% PFTBA (w/v) in the silk gel; black bar: 10% PFTBA (w/v) in the silk gel; light grey bar: 20% PFTBA (w/v) in the silk gel. Note that supplementation with PFTBA significantly enhances bone formation [p=0.033, 1-tailed T-test. N=13 implants in 5 mice for no PFTBA (0% (w/v) PFTBA) group, 15 implants in 5 mice for the 5% (w/v) PFTBA group, 16 implants in 6 mice for the 10% (w/v) PFTBA group and 12 implants in 4 mice for the 20% (w/v) PFTBA group]. FIGS. 1C-E—Representative images of the ectopic bone generated by the fibrin gel implants. FIG. 1C—0% (w/v) PFTBA (no-PFTBA); FIG. 1D—5% (w/v) PFTBA; FIG. 1E—10% (w/v) PFTBA; Size bars=1 mm. FIGS. 1F-I—Representative images of the ectopic bone generated by the silk gel implants. FIG. 1F—0% (w/v) PFTBA (no-PFTBA); FIG. 1G—5% (w/v) PFTBA; FIG. 1H—10% (w/v) PFTBA; FIG. 1I—20% (w/v) PFTBA; Size bars=1 mm. FIGS. 1J-L—Representative images depicting histological sections stained with Masson's Trichrom stain of the ectopic bone formed in the site of fibrin gel implantation depicting bone morphology on day 14-post implantation. FIG. 1J—0% (w/v) PFTBA (no-PFTBA); FIG. 1K—5% (w/v) PFTBA; FIG. 1L—10% (w/v) PFTBA. Size bars=100 μm. Note that there are no differences in the morphological features of the bone tissue formed in all three groups.

Figure 2A:
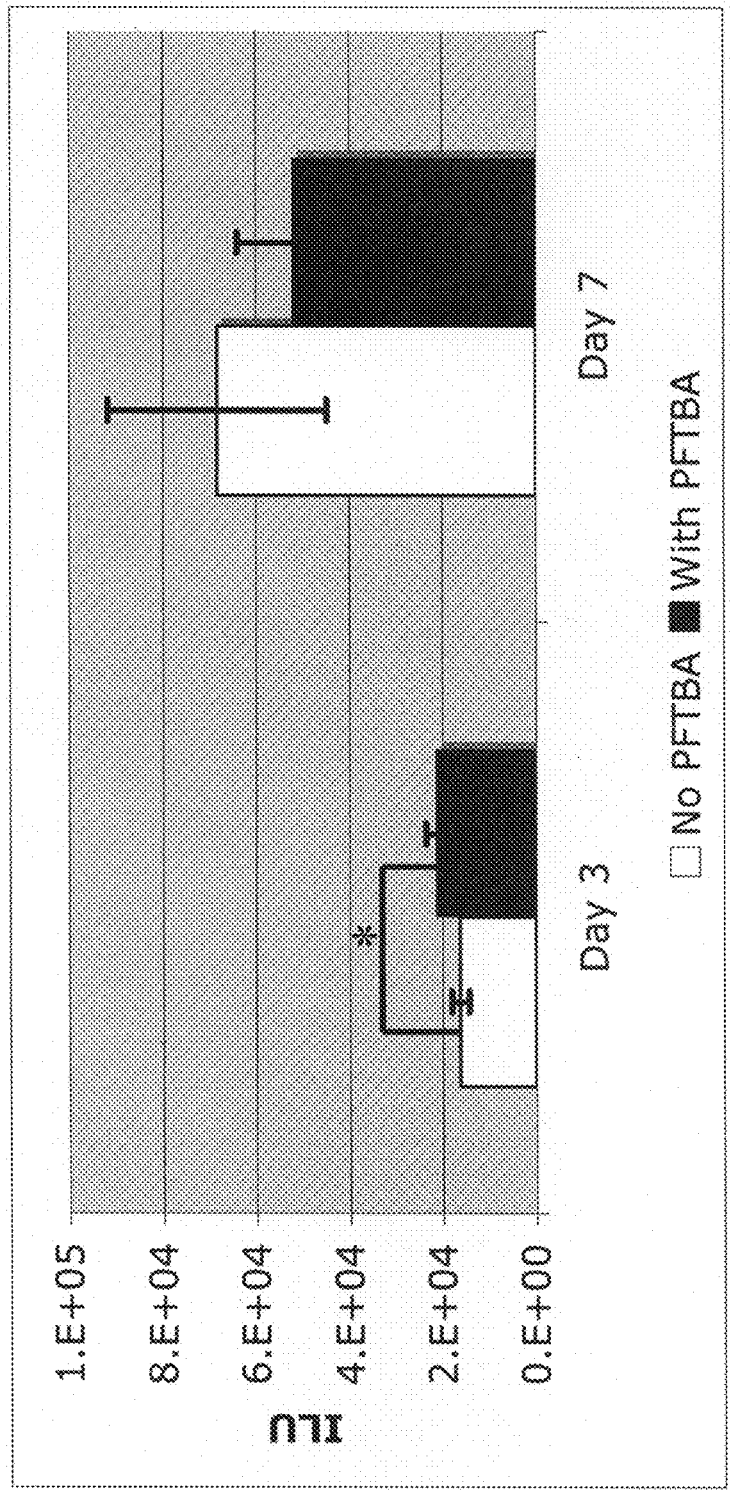

FIGS. 2A-D depict the effect of PFTBA on cell survival in ectopic implants. Three million Tet-off BMP2 MSCs, over-expressing the Luciferase (Luc) and GFP marker genes, were suspended in fibrin gels, which were supplemented with 0%, 5% or 10% (w/v) PFTBA. The gels were SC implanted in C3H/HeN mice and 3 and 7 days post SC implantation cell survival was monitored using the Bioluminescence Imaging (BLI) system. FIG. 2A—a histogram depicting Integrated Light Units (ILU) as a function of PFTBA content in the fibrin gels. White bars: 0% (w/v) PFTBA (no-PFTBA); black bars: 5% (w/v) and 10% (w/v) PFTBA (with PFTBA). Note that supplementation of the fibrin gel with PFTBA significantly enhances cell survival on day 3 post-implantation (P=0.044, 1-tailed T-test. N=15 implants in 5 mice for the no PFTBA group, 25-26 implants in 9 mice for the 5% (w/v) and 10% (w/v) PFTBA group). FIGS. 2B-D—Representative images depicting the bioluminescence signal emitted from ectopic implants of fibrin gel (on day 3 post implantation) containing Tet-off BMP2 MSCs, overexpressing the Luc and GFP marker genes. FIG. 2B—0% (w/v) PFTBA (no-PFTBA); FIG. 2C—5% (w/v) PFTBA; FIG. 2D—10% (w/v) PFTBA.

Figure 3A:
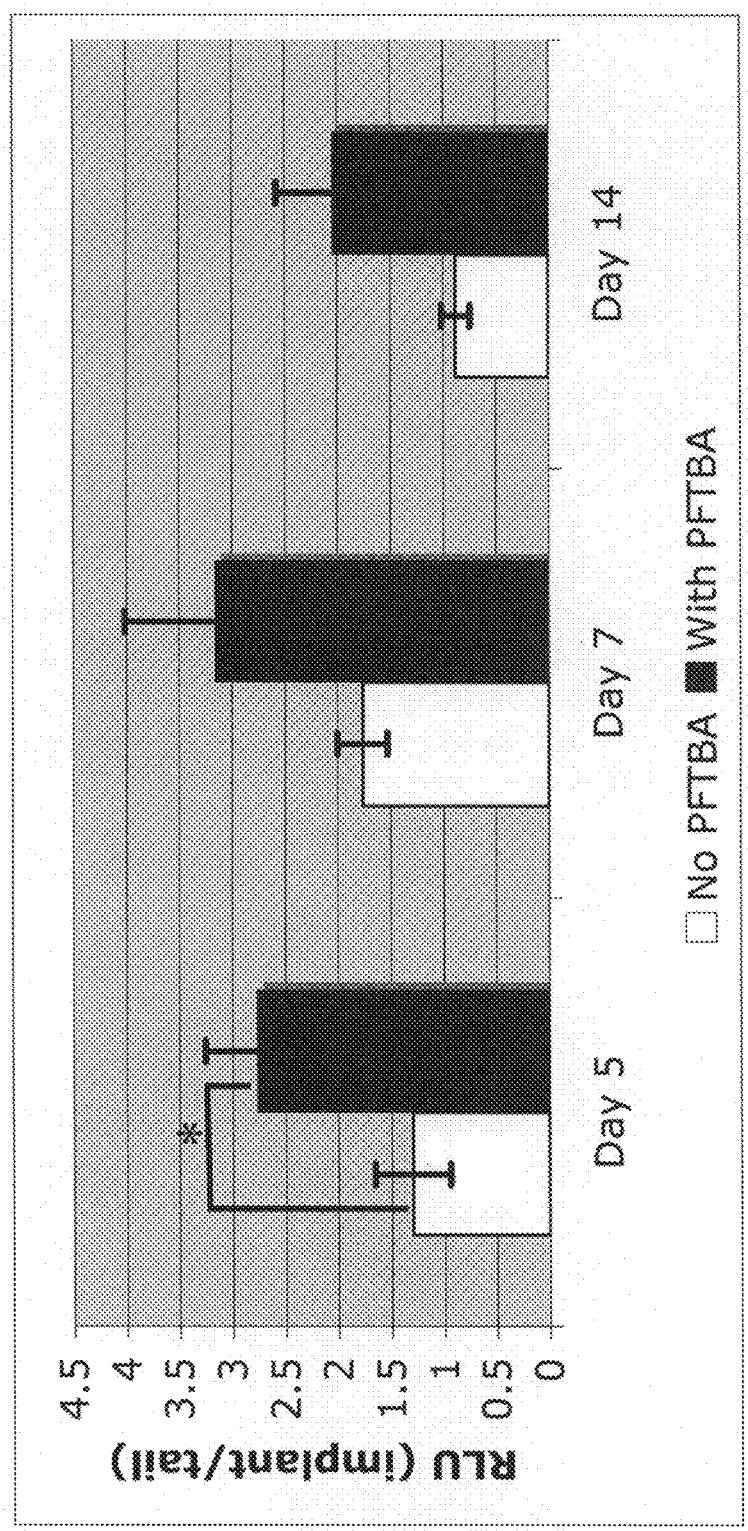

FIGS. 3A-D depict the effect of PFTBA on the paracrine expression of osteocalcin. One million Tet-off BMP2 MSCs were suspended in fibrin gels which were supplemented with 0%, 5%, or 10% PFTBA (w/v). The gels were implanted SC in Ostecalcin-Luciferase transgenic mice (OC/Luc Tg mice). At days 5, 7 and 14 post implantation bioluminescence was recorded using the BLI system. FIG. 3A-A histogram depicting bioluminescence intensity analysis [Relative Light Units (RLU)]. White bars: 0% PFTBA (no-PFTBA); black bars: 5% (w/v) and 10% (w/v) PFTBA (with PFTBA). Osteocalcin activity in the site of PFTBA supplemented implants is significantly enhanced at day 5 post implantation (p=0.046 one-tailed T-test; N=7-9 implants in 3 mice for the no PFTBA group, 19-25 implants in 7-9 mice for the 5% (w/v) and 10% (w/v) PFTBA group); FIGS. 3B-D are representative images of bioluminescence intensity, indicative of osteocalcin expression, taken at day 5 post implantation. FIG. 3B—0% (w/v) PFTBA (no-PFTBA); FIG. 3C—5% (w/v) PFTBA; FIG. 3D—10% (w/v) PFTBA.

Figure 4C:
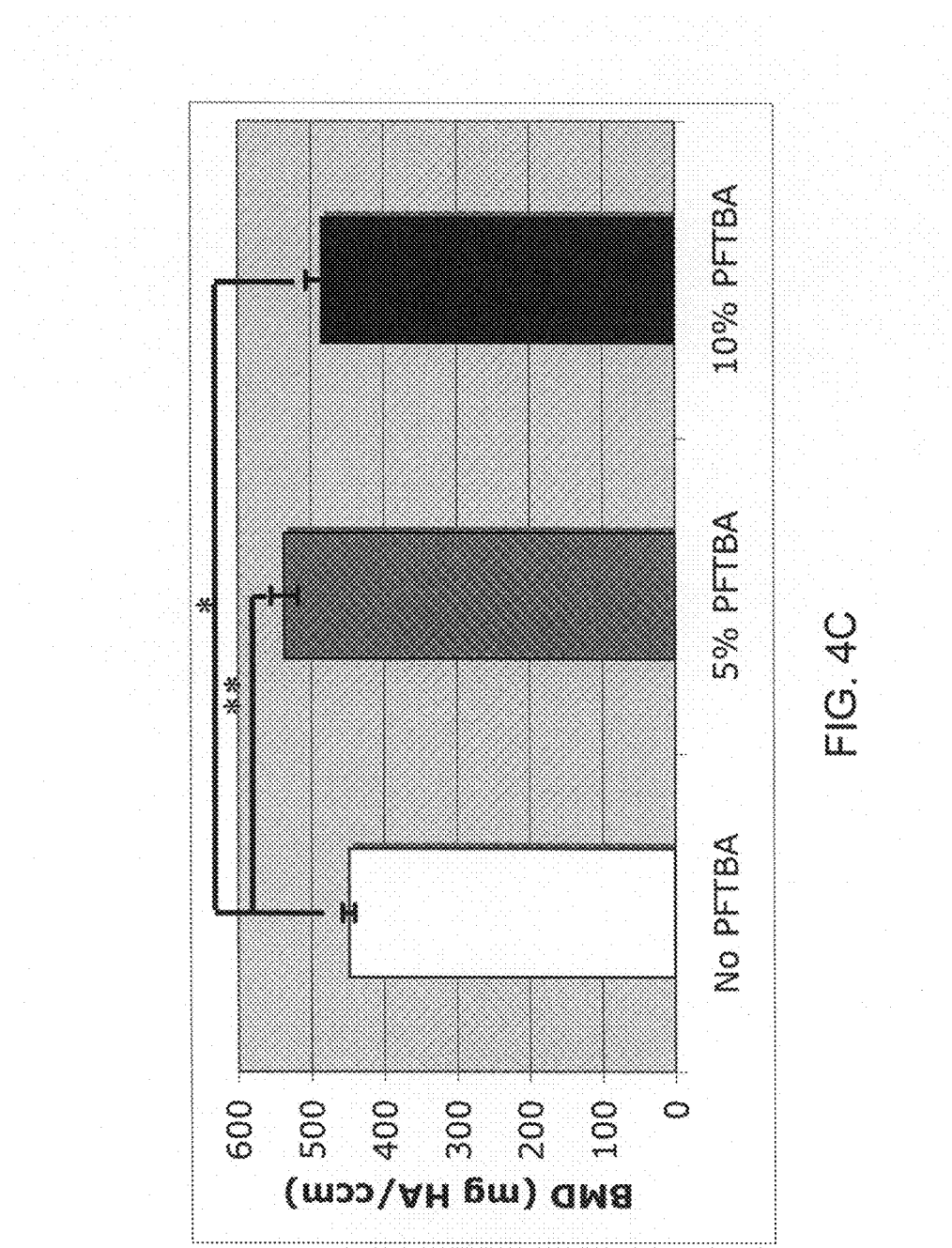
Figure 4D:
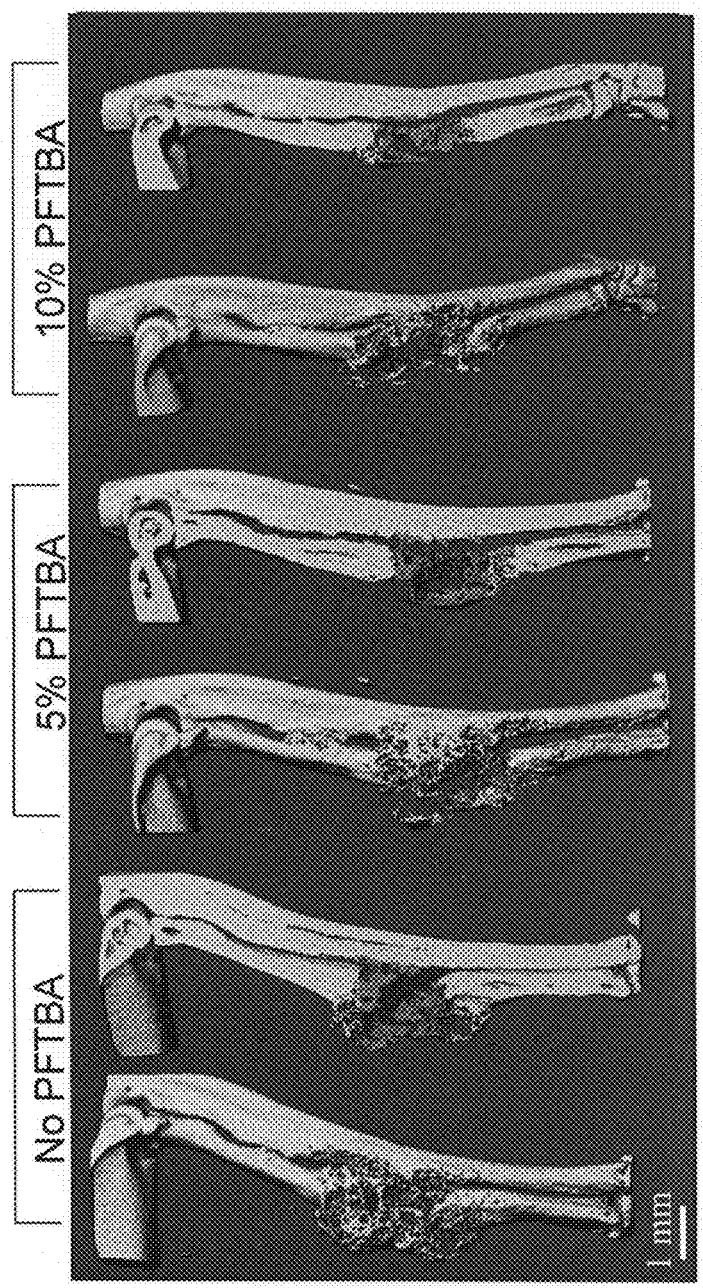

FIGS. 4A-D depict the effect of PFTBA on the healing of a segmental defect in the radius bone. Segmental bone defect of 2.5-mm long was made in the radius bone of C3H/HEN mice. One million Tet-off BMP2 MSCs were suspended in 15 µl fibrin gels, which were supplemented with 0%, 5% or 10% PFTBA (w/v). The gel-suspended cells were implanted into the defect site. At day 14 post implantation, mice were sacrificed, and defect regeneration was analyzed using micro-CT. FIG. 4A—a histogram depicting analysis of bone volume ($mm^3$) in implanted bone defects. White bars: 0% (w/v) PFTBA (no-PFTBA); Grey bars: 5% (w/v) PFTBA; black bars—10% (w/v) PFTBA. No difference is noted in the bone volume of the newly formed bone in the defect site. FIG. 4B—a histogram depicting analysis of trabecular thickness in implanted bone defects. Direct (DT) Trabecular (Tb)—Thickness (Th) mm. White bars: 0% (w/v) PFTBA (no-PFTBA); Grey bars: 5% (w/v) PFTBA; black bars—10% (w/v) PFTBA. A significant elevation in trabecular thickness is noted in the 5% (w/v) and 10% (w/v) PFTBA groups over the 0% (w/v) PFTBA group (*p=0.004, **p=0.013, 2-tailed T-test. N=6 for 0% (w/v) PFTBA; N=5 for 5% (w/v) PFTBA; and N=10% (w/v) PFTBA groups). FIG. 4C-A histogram depicting bone mineral density (BMD) (mg HA/ccm) in implanted bone defects. White bars: 0% (w/v) PFTBA (no-PFTBA); Grey bars: 5% (w/v) PFTBA; black bars—10% (w/v) PFTBA. A significant elevation in bone mineral density is noted in the 5% (w/v) and 10% (w/v) PFTBA groups over the 0% (w/v) PFTBA group (*p=0.055, **p=0.0008, 2-tailed T-test. N=6 for 0% (w/v) PFTBA group; N=5 for 5% (w/v) PFTBA group; and N=5 for the 10% (w/v) PFTBA group). FIG. 4D—Representative images of regenerated radii from all groups. In each group a 3D reconstruction and an axial view are presented. The site of bone defect regeneration is highlighted in orange.

Figures 5A, 5B, 5C, 5D:
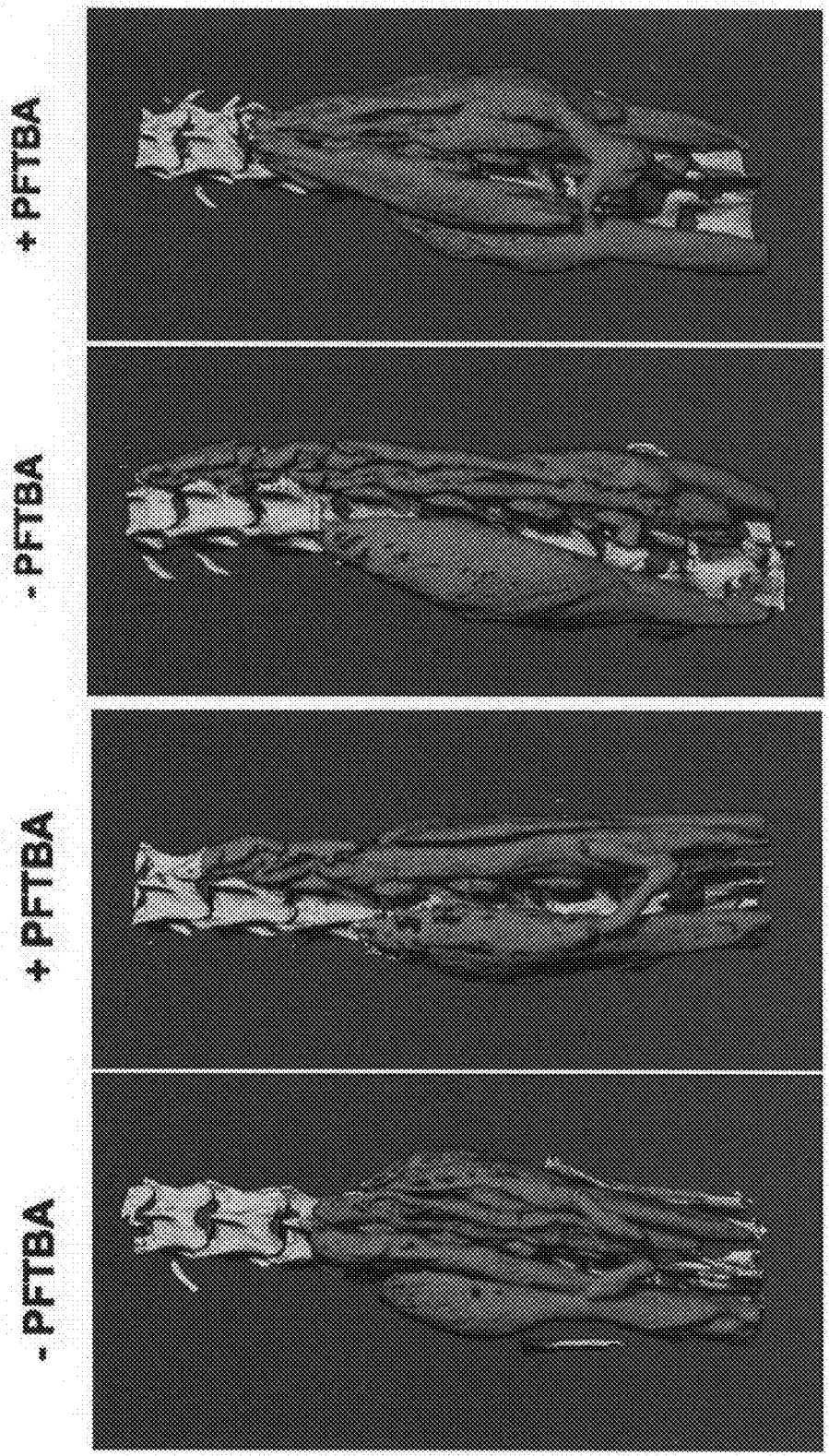
Figures 5E, 5F:
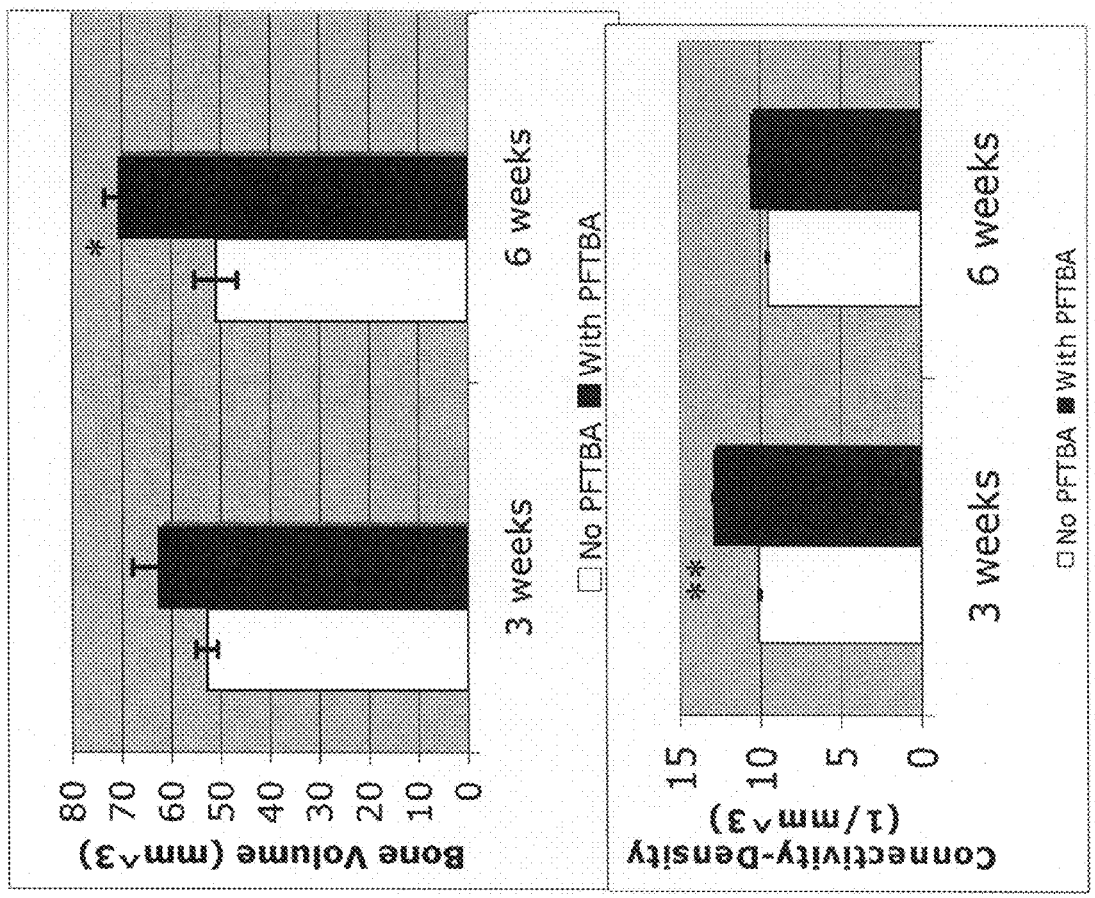
Figure 5G:
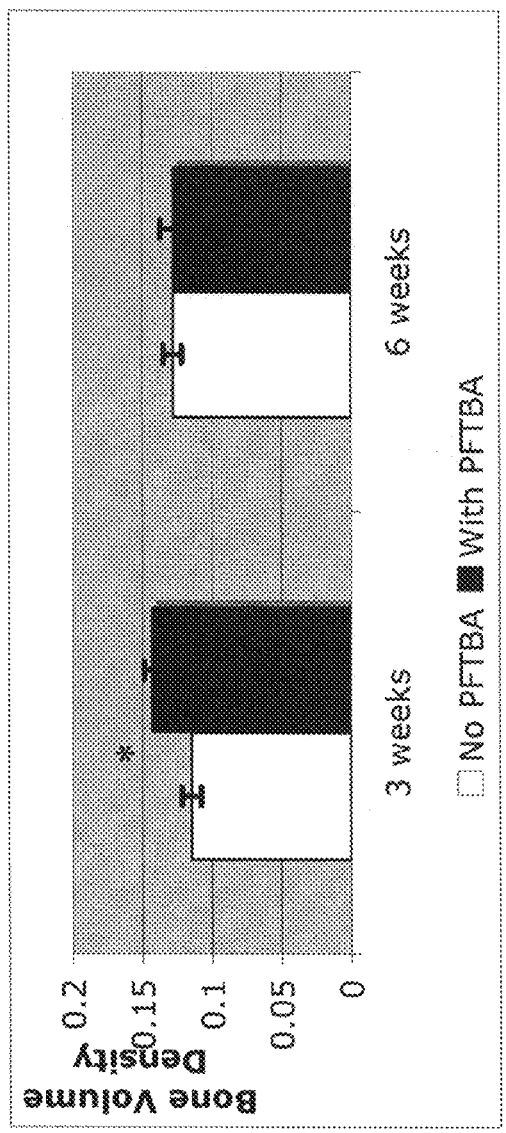
Figure 5H:
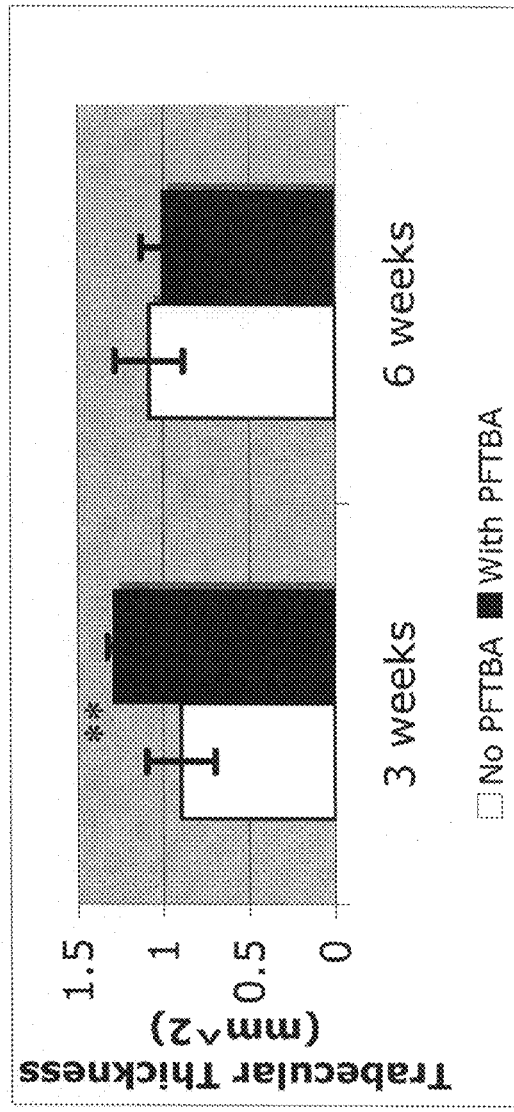

FIGS. 5A-H depict the effect of PFTBA on stem cell-mediated posterior spinal fusion. Tet-off BMP2 MSCs suspended in fibrin gel supplemented with 0% (w/v) or 10% (w/v) PFTBA were injected into the paraspinal muscle of C3H/HeN mice. Three or six weeks later the spins were harvested and scanned with micro-CT. FIGS. 5A-D—Three-dimensional (3D) images of the spines harvested after three (FIGS. 5A-B) or six (FIGS. 5C-D) weeks of injection of the fibrin gels (which include the MSCs) that were supplemented with 10% (w/v) PFTBA (FIGS. 5B and D) or 0% (w/v) PFTBA (FIGS. 5A and C). New bone formation is highlighted in orange. FIGS. 5E-H—Histograms depicting structural parameters obtained from the micro-CT (µCT) scans of spines harvested after injection of cells in gels supplemented with 10% (w/v) PFTBA (black bars) or 0% (w/v) PFTBA (white bars). FIG. 5E-A histogram depicting bone volume ($mm^3$) of the spinal fusion mass. *p=0.0008, 2-tailed T-test. N=at least 8 spines for each group at each time point; FIG. 5F-A histogram depicting connectivity-density ($1/mm^3$), **p=0.036, 2-tailed T-test. N=at least 8 spines for each group at each time point; FIG. 5G-A histogram depicting bone volume density ($mm^3/mm^3$), *p=0.001, 2-tailed T-test. n=at least 8 spines for each group at each time point; FIG. 5H-A histogram depicting the average trabecular thickness ($mm^2$). Bars indicate standard error (SE), **p=$2.65 \times 10^{-6}$) 2-tailed T-test. N=at least 8 spines for each group at each time point.

Figure 6A:
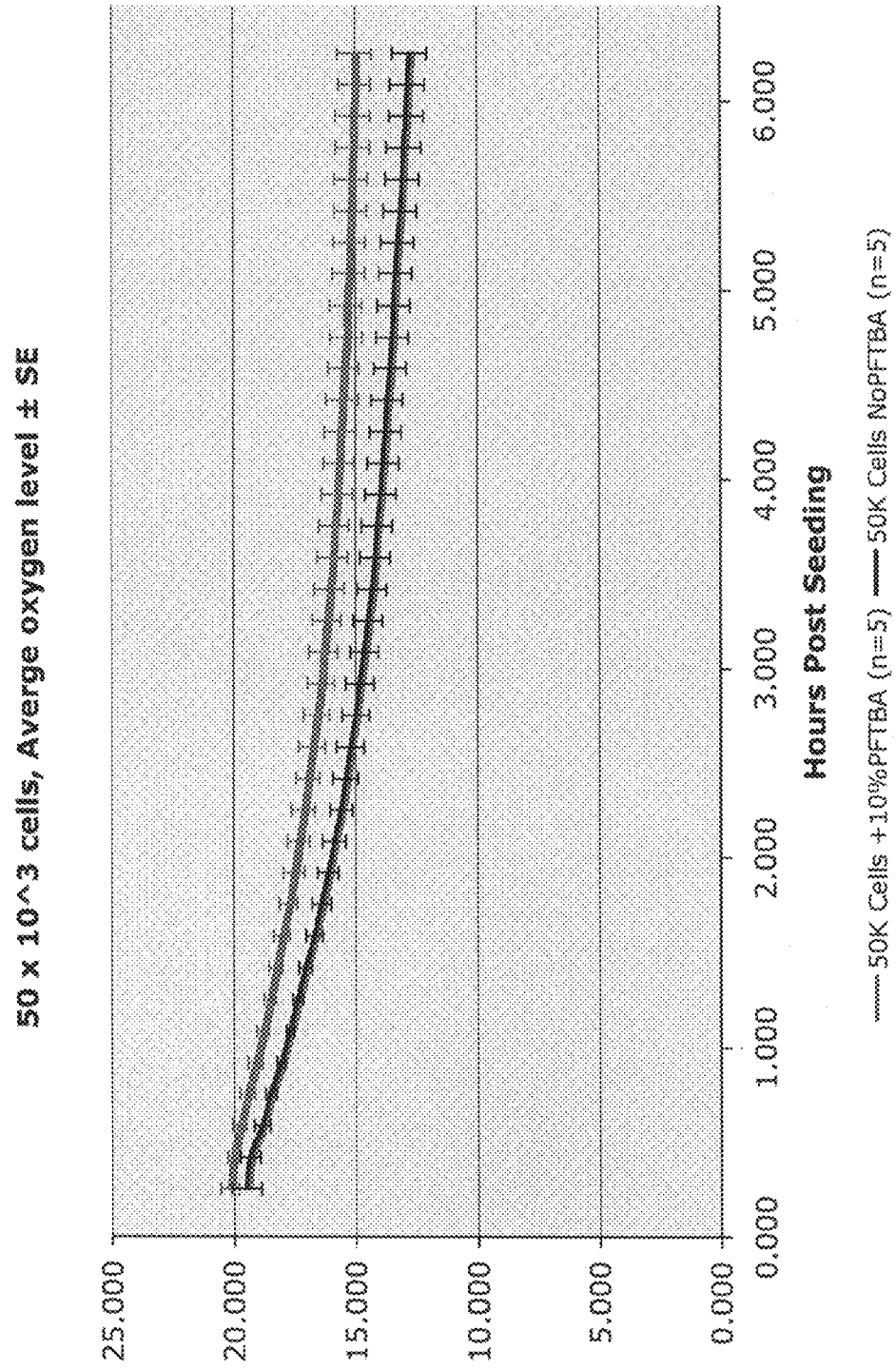
Figure 6B:
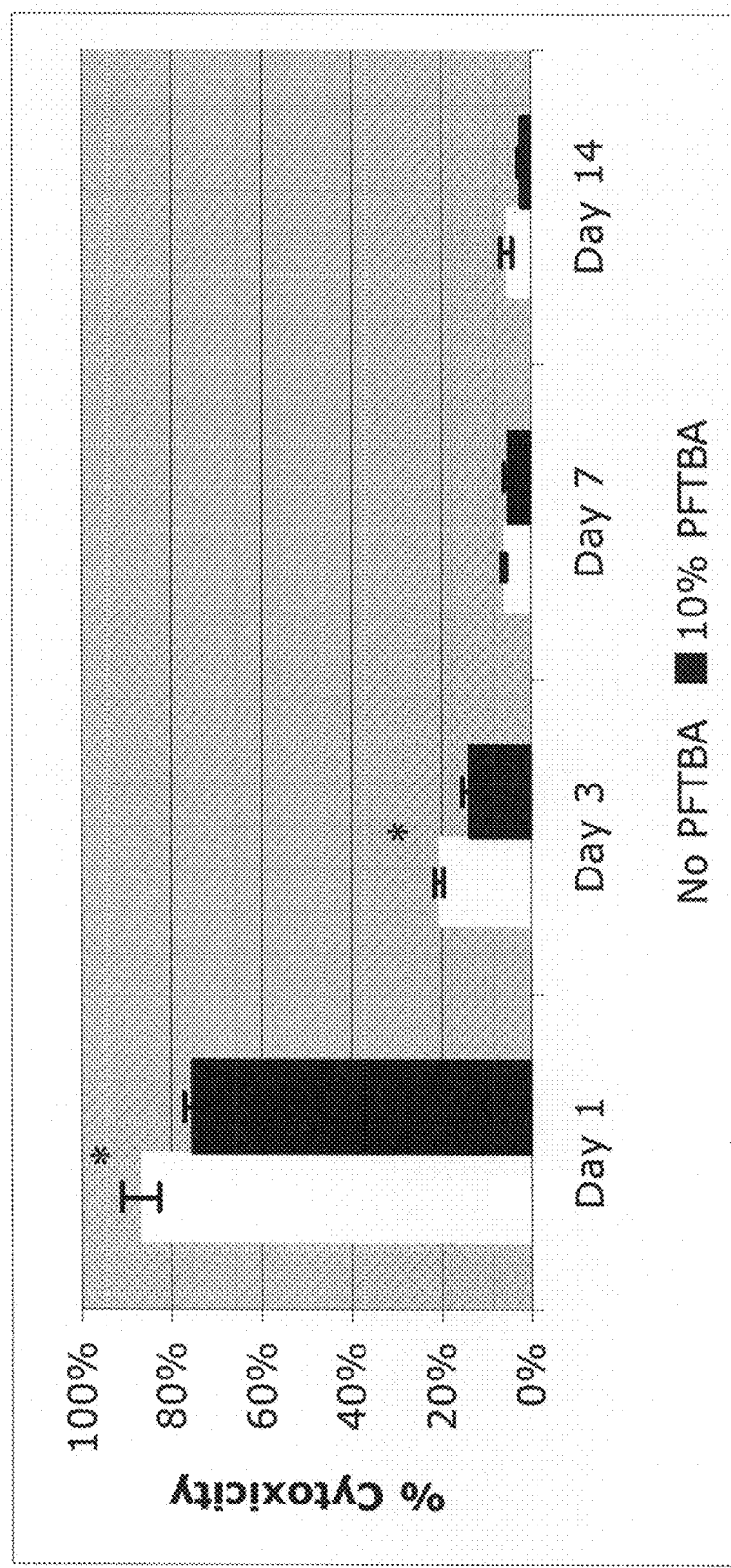

FIGS. 6A-B depict the effect of PFTBA on oxygen measurements and on MSCs cytotoxicity in fibrin gel in vitro. Tet-off BMP2 MSCs suspended in fibrin gel supplemented with 0% (w/v) or 10% (w/v) PFTBA were cultured as described. FIG. 6A-A graph depicting percent oxygen in fibrin gel in vitro. $50 \times 10^3$ MSCs were suspended in the fibrin gels supplemented with 10% (w/v) PFTBA (grey line) or 0% (w/v) PFTBA (black line) and the oxygen level was measured in the center of MSC-loaded gels using the Microx TX3 oxygen sensor. Shown is the average oxygen level±standard error (SE) over time post seeding (up to 6 hours post seeding). Note the significant difference in oxygen levels between the PFC-supplemented hydrogels to those with no PFTBA, p<0.05, 1-tailed t-test, n=5; FIG. 6B—A histogram depicting percent cytotoxicity in vitro. Cell death was measured using the LDH release cytotoxicity assay on Days 1, 3, 7 and 14 post seeding. Note that significantly fewer cells died in the PFTBA-supplemented hydrogels on days 1 and 3 after cell seeding when cultured in the hydrogel construct. *p<0.05, two-tail t-test.

DESCRIPTION OF SPECIFIC EMBODIMENTS OF THE INVENTION

The present invention, in some embodiments thereof, relates to scaffolds which comprise oxygen carriers such as perfluorocarbons and, more particularly, but not exclusively, to methods of using same for generating a tissue such as a connective tissue, and treating pathologies requiring tissue regeneration and/or repair.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the present invention to practice, the present inventors have uncovered that fibrin or silk scaffolds supplemented with perfluorocarbon (an oxygen carrier) such as perfluorotributylamine (PFTBA) can support and enhance proliferation and differentiation of adult tissue stem cells and thus can be used for tissue regeneration and/or repair.

Thus, as shown in the Examples section which follows, implantation of BMP-2 expressing mesenchymal stem cells (MSCs) which were suspended in PFTBA-containing fibrin or silk gels resulted in increased ectopic bone formation, increased bone volume (FIGS. 1A and B; Example 1), increased cell viability and survival (FIG. 2A; Example 2) and higher osteocalcin activity in host cells (FIG. 3A; Example 3) as compared to the ectopic bone formed by implantation of MSCs in fibrin or silk scaffolds devoid of PFTBA. In addition, implantation of MSCs in PFTBA-containing fibrin gels into a radius bone defect resulted in a significant elevation in bone structural parameters such as bone mineral density and trabecular thickness as compared to implantation of MSCs in fibrin gels devoid of PFTBA (FIGS. 4B and C; Example 4). Moreover, when MSCs in PFTBA-containing fibrin gels were used to promote spinal fusion by implantation into the lumbar paravertebral muscle, a significant elevation in bone volume, bone volume density, connectivity density and trabecules number was observed as compared to implantation of MSCs in fibrin gels devoid of PFTBA (FIGS. 5A-H; Example 5). In addition, PFTBA-supplemented hydrogels supported a higher oxygen tension in the center of the gels as compared to hydrogels devoid of PFTBA (FIG. 6A) and prevented cell death of the implanted MSCs (FIG. 6B). These results demonstrate that matrices supplemented with an oxygen carrier such as PFTBA enhance MSCs proliferation and differentiation and can be used for tissue formation, regeneration and/or repair.

Thus, according to an aspect of some embodiments of the present invention there is provided a matrix comprising a backbone and an oxygen carrier.

As used herein the terms "matrix" or "scaffold" which are interchangeably used herein, refer to a three-dimensional supporting framework, which enables growth of cells therethrough. The matrix backbone can be composed of units, which are directly, or indirectly (e.g., via linker) attached.

According to some embodiments of the invention, the matrix comprises a continuous matrix backbone.

According to some embodiments of the invention, the continuous matrix has a volume of at least a cubic centimeter (cm) range, e.g., at least about 1 cm$^3$, at least about 2 cm$^3$, at least about 3 cm$^3$, at least about 5 cm$^3$, at least about 10 cm$^3$, at least about 20 cm$^3$, at least about 30 cm$^3$, at least about 40 cm$^3$, at least about 50 cm$^3$, at least about 60 cm$^3$, at least about 70 cm$^3$, at least about 80 cm$^3$, at least about 90 cm$^3$, at least about 100 cm$^3$, at least about 200 cm$^3$, at least about 300 cm$^3$, at least about 400 cm$^3$, e.g., about 500 cm$^3$.

According to some embodiments of the invention, the matrix comprises a plurality of pores. The pores can be in the range from about 200 nanometers (nm) to about 2 millimeters (mm). The pores in the supporting framework of the matrix enable the growth, migration, proliferation and/or differentiation of cells therethrough and allow supply of nutrients to the cells.

According to some embodiments of the invention, the matrix exhibits a porosity [i.e., the ratio of the volume of the pores to the volume of the backbone] of at least about 20%, at least about 30%, at least about 40%, at least about 50%, e.g., in the range of about 50-90

Methods of preparing the matrix backbone are known in the art and include for example mixing the matrix units [e.g., dissolving the molecules/polymer(s) in a solvent to form a solution] and solidifying the solution using for example, evaporation of the solvent (e.g., chloroform; see e.g., Yang D. T., et al., Proc. Natl. Acad. Sci. U.S.A. 2002, 99: 3024-3029; Kang B C, et al., Exp Anim. 2005, 54:37-52) or coagulation in an ethanol bath (see e.g., Lepidi S., et al., FASEB J. 2006, 20: 103-5). Additionally or alternatively, the matrix can be generated by electro-spinning of the polymeric solutions [see for example, Wan Y, et al., 2008, Acta Biomater. 4:876-86, "Fibrous poly(chitosan-g-DL-lactic acid) scaffolds prepared via electro-wet-spinning"], three-dimensional (3D) printing [Park Y. J., Nam K. H., Ha S. J., et al., 1997. Porous poly (L-lactide) membranes for guided tissue regeneration and controlled drug delivery: membrane fabrication and characterization. J. Controlled Release 43:151-160] and phase separation techniques [Mooney D. J. Baldwin, D. F., Suh, N. P., et al., 1996. Novel approach to fabricate porous sponges of poly (D,L-lactic-co-glycolic acid) without the use of organic solvents. Biomaterials 17:1417-1422].

The matrix pores can be generated by various methods known in the art, such as by casting the matrix over a mold, which includes salt particles (such as sodium chloride at a predetermined size such as a diameter range of 250-500 μm), or by mixing the matrix solution with the salt particles, and following solidification, removing the salt particles by washes in distilled water [see e.g., Kim S S, et al., Ann Surg. 1998, 228:8-13]. Additionally or alternatively, the pores can be generated using a gas-forming agent like $CO_2$, which generates gas bubbles that shape the developing pores in the scaffold [Tai H, Mather M L, Howard D, Wang W, White L J, Crowe J A, Morgan S P, Chandra A, Williams D J, Howdle S M, Shakesheff KM. 2007. Control of pore size and structure of tissue engineering scaffolds produced by supercritical fluid processing. Eur. Cell Mater. 14:64-77].

According to some embodiments of the invention, the matrix backbone is made of a biocompatible and/or biodegradable molecule/polymer.

The term "biocompatible" as used herein refers to any molecule/polymer (synthetic or natural) which when in contact with cells, tissues or body fluid of an organism does not induce adverse effects such as immunological reactions and/or rejections, cellular death, toxicity and the like. A biocompatible polymer can also be a biodegradable polymer.

The term "biodegradable" refers to a synthetic or natural molecule/polymer, which can be degraded (i.e., broken down) in a physiological environment such as by proteases or other enzymes produced by living organisms such as bacteria, fungi, plants and animals, hydrolysis, and dissolution. Biodegradability depends on the availability of degradation substrates (i.e., biological materials or portion thereof which are part of the molecule/polymer), the presence of biodegrading materials (e.g., microorganisms, enzymes, proteins) and the availability (e.g., for aerobic organisms, microorganisms or portions thereof) or lack (e.g., for anaerobic organisms, microorganisms or portions thereof) of oxygen and/or other nutrients.

Various molecules such as synthetic or natural polymers can be used to form the matrix backbone of the invention. These include, but are not limited to, polyethylene glycol (PEG), fibrinogen, silk, PEGylated fibrinogen, collagen, PEGylated collagen, fibronectin, PEGylated fibronectin, agarose, alginate, chitosan, fibrin, gelatin, cellulose, albumin, gluten, elastin, starch, sclerolutan, elsinan, pectin, galactan, curdlan, gellan, levan, emulsan, dextran, pullulan, heparin, chondroitin-6-sulfate, hyaluronic acid (HA) Hydroxyapatite/polycaprolactone (HA/PLC), polyglycolic acid (PGA), Poly-L-lactic acid (PLLA), Polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and nonbiodegradable polytetrafluoroethylene (PTFE), ceramic-polymer composite, poly(ethylene oxide) (PEO), poly(vinyl alcohol) (PVA), poly(acrylic acid) (PAA), poly(propylene fumarate-co-ethylene glycol) (P(PF-coEG)), poly(chitosan-g-DL-lactic acid) (PCLA), nucleic acids (DNA, RNA), polypeptides, and any combinations thereof.

According to specific embodiments of the invention, the matrix is composed of a fibrin backbone. The term "fibrin" as used herein refers to the fibrous polypeptide formed by the conversion of fibrinogen by thrombin. Non-limiting examples of fibrinogen polypeptides which can be used to form the fibrin matrix of the invention include fibrinogen alpha, beta and/or gamma chains which can be derived from various species such as *homo sapiens* [e.g., GenBank Accession numbers: NP_000499.1 (SEQ ID NO:1); NP_068657.1 (SEQ ID NO:2); NP_005132.2 (SEQ ID NO:3); NP_000500.2 (SEQ ID NO:4); NP_068656.2 (SEQ ID NO:5)], rat (e.g., GenBank Accession numbers: NP_001008724.1; NP_064456.1; NP_036691.2), cow (e.g., GenBank Accession numbers: NP_001028798.1, XP_587666.3, NP_776336.1), chicken, *Canis lupus familiaris*, *Xenopus*, zebra fish, mouse, mosquito, monkey, and opossum (*Monodelphis domestica*).

The matrix according to some embodiments of the invention the matrix further comprises thrombin, which converts fibrinogen to fibrin.

Methods of generating fibrin scaffolds are known in the art, see e.g., Almany L, Seliktar D. Biosynthetic hydrogel scaffolds made from fibrinogen and polyethylene glycol for 3D cell cultures. Biomaterials. 2005 May; 26(15):2467-77; Gonen-Wadmany M, Oss-Ronen L, Seliktar D. Protein-polymer conjugates for forming photopolymerizable biomimetic hydrogels for tissue engineering. Biomaterials. 2007 September; 28(26):3876-86.

According to specific embodiments of the invention, the matrix is composed of a silk backbone.

The term "silk" as used herein refers to a silk fibroin purified from silk cocoons or produced by recombinant DNA techniques.

Non-limiting examples of silk proteins which can be used to generate of the matrix of the invention include those extracted from *Bombyx mori* cocoons [(Linne, 1758); see e.g., Kim U J, Park J, Li C, Jin H J, Valluzzi R, Kaplan D L. 2004. "Structure and properties of silk hydrogels". Biomacromolecules. 5:786-92] or Sericin-hope silkworm cocoons (see e.g., Teramoto H, Nakajima K, Takabayashi C. 2005, "Preparation of elastic silk sericin hydrogel". Biosci. Biotechnol. Biochem. 69:845-7).

As mentioned, silk can be also prepared by recombinant DNA techniques using for example, nucleic acid constructs encoding the silk fibroin light chain [GenBank Accession No. NM_001044023.1 (SEQ ID NO:27) for the polynucleotide; GenBank Accession No. NP_001037488.1 (SEQ ID NO:28) for the polypeptide] and/or heavy chain [GenBank Accession No. NM_001113262.1 (SEQ ID NO:29) for the polynucleotide; GenBank Accession No. NP_001106733.1 (SEQ ID NO:30) for the polypeptide].

It should be noted the silk protein may be also mixed with or covalently conjugated to additional molecules (e.g., proteins) which change the physical characteristics of the silk (e.g., increase the strength and/or elasticity of the silk). Non-limiting examples of such proteins include elastin, fibrin and collagen [see e.g., Hwang D., Moolchandani V, et al., "Influence of polymer structure and biodegradation on DNA release from silk-elastin like protein polymer hydrogels". International Journal of Pharmaceutics, 2008 Nov. 5 (Epub ahead of print)]. Silk can be also provided by various Biotechnology companies such as ProteinPolymerTechnologies, Inc. (SanDiego, Calif.).

Methods of generating silk matrices are known in the art. See e.g., Kim U J, Park J, Li C, Jin H J, Valluzzi R, Kaplan D L. 2004. "Structure and properties of silk hydrogels". Biomacromolecules. 5:786-92; and Matsumoto, A., Chen, J., Collette, A. L., Kim, U. J., Altman, G. H., Cebe, P., and Kaplan, D. L. 2006. Mechanisms of silk fibroin sol-gel transitions. J Phys Chem B Condens Matter Mater Surf Interfaces Biophys. 110:21630-21638.

It should be noted that the molecules forming the matrix backbone can be further subject to cross-linking in order to covalently bind the matrix units and/or to increase the strength of the backbone. Cross-linking can be performed using a cross linking agent (which activates covalent binding between the matrix units) and/or by subjecting the matrix units to an energy source such as an ultra violet light, which connects between at least two units of the matrix backbone. Suitable cross-linking molecules, which can be used to generate the matrix backbone of the invention, include, but are not limited to, a reactive molecule such as a free radical, polyethylene glycol (PEG), thrombin, glutaraldehyde and microbial transglutaminase (TGase).

As used herein the phrase "oxygen carrier" refers to a molecule capable of transporting, delivering and/or supplying oxygen to cells, thus supporting viability, proliferation, differentiation and/or migration of cells.

The oxygen carrier may be embedded within or covalently attached to the matrix backbone. According to some embodiments of the invention, the embedded oxygen carrier is unable to flow through, in or on the matrix backbone. Covalent attachment of the oxygen carrier to the matrix backbone may be via, for example a tethering molecule such as Poly [Ethylene Glycol]).

The oxygen carrier can be incorporated into the matrix by various ways. For example, the oxygen carrier may be mixed with the matrix units (e.g., the polymeric solution) and be subjected to the solidification process forming the matrix backbone such that it is embedded within the matrix backbone. For example, if the matrix is formed by a gel suspension, the oxygen carrier can be mixed with the gel's solution and be subjected to the solidification process casting the gel. Additionally or alternatively, if electro-spinning is employed in order to form the matrix, the oxygen carrier may be mixed with the polymeric solutions prior to the electro-spinning process. Still additionally or alternatively, the oxygen carrier may be covalently bound to the matrix backbone using for example, a cross linking agent or an energy source as described above.

According to some embodiments of the invention the oxygen carrier comprised in the matrix of the invention is a hemoglobin-based molecule or a perfluorocarbon molecule or a derivative thereof.

Non-limiting examples of suitable hemoglobin-based molecules include crosslinked haemoglobin, polymerized haemoglobin, recombinant haemoglobin, encapsulated haemoglobin, HEMOPURE® (Biopure Corporation, Cambridge Mass.), POLYHEME® (Northfield Laboratories, Evanston, Ill.), and HEMOSPAN® (Sangart, Corp., San Diego, Calif.)].

Perfluorocarbons are compounds derived from hydrocarbons by replacement of hydrogen atoms by fluorine atoms. Non-limiting examples of suitable perfluorocarbons include perfluorotributylamine [PFTBA; $(C_4F_9)_3N$], perfluorooctylbromide [PFOB; $C_8F_{17}Br$), octafluoropropane, perfluorohexane, perfluorodecalin, perfluorodichlorooctane, perfluorodecane, perfluorotripropylamine, perfluorotrimethylcyclohexane, perfluoroperhydrophenanthrene, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, or mixtures thereof. Perfluorocarbon derivatives are perfluorocarbons with some functional groups attached thereto.

According to some embodiments of the invention the concentration of the oxygen carrier in the matrix is at least about 1% weight per volume (w/v), e.g., at least about 5% (w/v), e.g., at least about 7.5% (w/v), e.g., at least about 10% (w/v), e.g., at least about 12.5% (w/v), e.g., at least about 15% (w/v), e.g., at least about 17.5% (w/v), e.g., at least about 20% (w/v), e.g., at least about 30% (w/v), e.g., at least about 40% (w/v).

According to some embodiments of the invention the concentration of the oxygen carrier in the matrix is in the range of about 1-50% (w/v), e.g., about 1-30% (w/v), e.g., about 5-30% (w/v), e.g., about 5-25% (w/v), e.g., about 5-10% (w/v), e.g., about 5-20% (w/v).

Thus, the teachings of the invention can be used to generate a matrix comprising a fibrin or silk backbone and an oxygen carrier (see for example, the matrices comprising perfluorocarbon such as PFTBA embedded within the fibrin or silk backbone, which are described in the Examples section which follows).

The matrix of the invention may also contain additional agents such as growth factors, anti inflammatory agents and/or antibiotics, which promote viability, proliferation, differentiation and/or migration of cells therethrough.

According to some embodiments of the invention, the matrix of the invention is a hydrogel matrix.

As used herein, the term "hydrogel matrix" refers to a three dimensional (3D) network of macromolecules typically covalently or ionically linked in which water is the dispersion medium.

According to some embodiments of the invention, the hydrogel comprises at least about 30% water [volume per volume (v/v)], at least about 40% (v/v) water, at least about 50% (v/v) water, at least about 60% (v/v) water, at least about 70% (v/v) water, at least about 80% (v/v) water, at least about 90% (v/v) water, at least about 95% (v/v) water, at least about 99% (v/v) water.

Methods of preparing hydrogels are known in the art and include for example those described in Pratt A B, et al. [Synthetic extracellular matrices for in situ tissue engineering. Biotechnol Bioeng. 2004 Apr. 5; 86(1):27-36]. Briefly, the matrix precursor molecules can be mixed with water and optionally a cross-linking agent (e.g., glutaraldehyde) to thereby obtain a semi-solid hydrogel. It should be noted that before the hydrogel solution sets-in permanently as a gel, it can be processed by extrusion, casting, molding or coating as required for the fabrication of a specific scaffold.

The matrix of the invention can be available as a dry matrix, a wetted matrix, a hydrogel, a sponge or a fiber, depending on the intended use. For example, the matrix can be prepared as a dry matrix and be wetted prior to use. Additionally or alternatively, the matrix can be prepared as a hydrogel, which can be directly used for tissue generation and/or repair, or can be lyophilized and be kept under dry conditions until use (e.g., at −80° C.). Lyophilized matrices can then be re-hydrated in an aqueous solution (e.g., water, phosphate buffer saline) before use.

It should be noted that incorporation of the oxygen carrier to the matrix is advantageous over prior art methods in which the oxygen carrier was provided to cells cultured on or in the matrix via the culture medium (e.g., by perfusion of the oxygen carrier through matrix channels or pores, or by culturing cells over a matrix which does not enable penetration of cells therethrough such as a silicone membrane) and not as part of the matrix. Thus, as the matrix of the invention comprises the oxygen carrier (e.g., by embedding or covalent attachment) it is suitable for in vivo tissue engineering since it enables proliferation, differentiation and/or migration of cells therethrough and formation of a tissue without the need for a continuous infusion or perfusion of the oxygen carrier to the matrix.

According to some embodiments of the invention, the matrix further comprising cells.

As used herein the term "cells" encompasses isolated cells (i.e., cells which are isolated from a biological sample) as well as cells which are comprised within a biological sample [e.g., a crude tissue sample such as a tissue biopsy, a cell aspirate (e.g., bone marrow aspirate)] in which the cells are present in their natural environment as present in the body. The cells may be genetically manipulated, freshly isolated and non-expanded, or cultured with specific growth factors before introduction into the body.

According to some embodiments of the invention, the cells can be embedded within, absorbed to, or immobilized within or on the matrix. For example, the cells can be mixed with the matrix components during matrix preparation (see for example, the "General Material and Methods" in the Examples section which follows), or be loaded on or absorbed to the matrix after the matrix is formed. Additionally or alternatively, when used for in vivo applications, the cells can also migrate throughout or on the matrix after implantation in a subject.

The cells of the invention can be any cells, including stem cells and differentiated cells.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells).

Non-limiting examples of stem cells which can be used with the matrix of the invention include embryonic stem cells (ESCs), induced pluripotent stem cells (iPS), adult stem cells (including hematopoietic stem cells) and progenitor cells.

The phrase "adult stem cells" (also called "tissue stem cells" or a stem cell from a somatic tissue) refers to any stem cell derived from a somatic tissue [of either a postnatal or prenatal animal (especially the human); see e.g., Park I H et al., Reprogramming of human somatic cells to pluripotency with defined factors. Nature. 2008 Jan. 10; 451(7175):141-6]. The adult stem cell is generally thought to be a multipotent stem cell, capable of differentiation into multiple cell types. Adult stem cells can be derived from any adult, neonatal or fetal tissue such as adipose tissue, intervertebral disc, skin, kidney, liver, prostate, pancreas, intestine, bone marrow (BM), amniotic fluid and placenta. Placental and cord blood stem cells may be also referred to as "young stem cells". Hematopoietic stem cells include stem cells obtained from blood or bone marrow tissue of an individual at any age or from cord blood of a newborn individual.

Bone marrow—derived stem cells include hematopoietic, stromal, mesenchymal stem cells (Dominici, M et al., 2001. Bone marrow mesenchymal cells: biological properties and clinical applications. J. Biol. Regul. Homeost. Agents. 15: 28-37) or CD105 positive cells (Asian H, et al., 2006, Osteogenic differentiation of noncultured immunoisolated bone marrow-derived CD105+ cells. Stem Cells. 24: 1728-37) and can be obtained from iliac crest, femora, tibiae, spine, rib or other medullar spaces.

Mesenchymal stem cells (MSCs) are formative pluripotent blast cells, which give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. MSCs can be isolated from the bone marrow, adipose tissue, embryonic yolk sac, placenta, umbilical cord, fetal and adolescent skin, blood, intervertebral disc and other tissues.

According to some embodiments of the invention, the cells, which are comprised in the matrix of the invention, are mesenchymal stem cells.

Methods of isolating, purifying and expanding mesenchymal stem cells (MSCs) are known in the arts and include, for example, those disclosed by Caplan and Haynesworth in U.S. Pat. No. 5,486,359; Jones E. A. et al., 2002, Isolation and characterization of bone marrow multipotential mesenchymal progenitor cells, Arthritis Rheum. 46(12): 3349-60; and Asian H, et al., 2006, Osteogenic differentiation of noncultured immunoisolated bone marrow-derived CD105+ cells. Stem Cells. 24: 1728-37.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions.

As mentioned, the cells, which are comprised in the matrix of the invention, can be genetically modified (e.g., transformed by an exogenous polynucleotide/nucleic acid construct) to express a polynucleotide or polypeptide-of-interest. The polypeptide-of-interest can be, for example, a protein which induces connective tissue formation such as bone morphogenetic protein [e.g., GenBank Accession number NP_001191.1 (SEQ ID NO:6) for the polypeptide and GenBank Accession number NM_001200.2 (SEQ ID NO:7) for the polynucleotide]; a SMAD protein such as SMAD-8 [SEQ ID NO:8 for the polypeptide including the MH1, linker and MH2 domains; and SEQ ID NO:9 for polypeptide including the linker and MH2 domains of the protein; SEQ ID NO:10 for the polynucleotide encoding the MH1, linker and MH2 domains of SMAD-8; and SEQ ID NO:11 for the polynucleotide encoding the linker+MH2 domains of SMAD-8], SMAD-9 [e.g., GenBank Accession number NP_620227.1 (SEQ ID NO:12) for the polypeptide and GenBank Accession number NM_138872.1 (SEQ ID NO:13) for the polynucleotide; and GenBank Accession number NM_001127217.1 (SEQ ID NO: 14) for the polynucleotide and NP_001120689.1 (SEQ ID NO:15) for the polypeptide], SMAD-5 [e.g., GenBank Accession number NP_001001419.1 (SEQ ID NO:16) for the polypeptide and GenBank Accession number NM_001001419.1 (SEQ ID NO:17) for the polynucleotide], or SMAD-1 [e.g., GenBank Accession number NP_001003688.1 (SEQ ID NO:18) for the polypeptide and GenBank Accession number NM_001003688 (SEQ ID NO:19) for the polynucleotide]; and/or Brachyury [T-Box 1; e.g., GenBank Accession numbers NP_005983.1 (SEQ ID NO:20), NP_542377.1 (SEQ ID NO:21), and NP_542378.1 (SEQ ID NO:22) for the polypeptide; and GenBank Accession numbers NM_005992.1 (SEQ ID NO:23), NM_080646.1 (SEQ ID NO:24), and NM_080647.1 (SEQ ID NO:25) for the polynucleotide].

According to some embodiments of the invention, the cells are genetically modified to express two or more polynucleotides-of-interest. Non-limiting examples include co-expression of BMP and SMAD polynucleotides; co-expression of BMP and Brachyury polynucleotides; co-expression of SMAD and Brachyury polynucleotides; or co-expression of BMP, Brachyury and SMAD polynucleotides;

Additionally or alternatively, the cells can be genetically modified to express genes conferring resistance to various drugs, pathogens and the like.

To express the polypeptide-of-interest in a cell (e.g., a eukaryotic cell such as a mammalian cell), a polynucleotide-of-interest (e.g., a polynucleotide encoding a polypeptide-of-interest) is preferably ligated into a nucleic acid construct suitable for mammalian cell expression. Such a nucleic acid construct may include a promoter sequence for directing transcription of the polynucleotide sequence in the cell in a constitutive, tissue specific or inducible manner; sequences which render this vector suitable for replication and integration in prokaryotes, eukaryotes, or preferably both (e.g., shuttle vectors); a transcription and translation initiation sequence, transcription and translation terminator and a polyadenylation signal; a signal sequence for secretion of the polypeptide from a host cell in which it is placed; and specialized elements intended to increase the level of expression of cloned nucleic acids or to facilitate the identification of cells that carry the recombinant DNA.

Thus, the teachings of the invention can be used to generate a matrix, which comprises an oxygen carrier and mesenchymal stem cells (see, e.g., the fibrin or silk matrices described in the Examples section which follows, which comprise mesenchymal stem cells).

As mentioned above and described in the Examples section which follows, matrices generated according to the present teachings, which include stem cells such as MSCs, can be used to generate a tissue.

Thus, according to some embodiments of the invention there is provided a method of generating a tissue. The method is effected by (a) providing the matrix of the invention; and (b) seeding the matrix with cells, thereby generating the tissue.

The phrase "tissue" as used herein refers to a group of cells that perform a similar function. Examples include, but are not limited to, a connective tissue, brain tissue, neuronal tissue, retina, skin tissue, hepatic tissue, pancreatic tissue, blood tissue, muscle tissue, cardiac tissue, vascular tissue, renal tissue, pulmonary tissue, gonadal tissue, hematopoietic tissue.

According to some embodiments of the invention, the tissue is a connective tissue, including, but not limited to, a bone tissue (e.g., osseous tissue), a loose connective tissue, an extracellular matrix (ECM), a tendon tissue, a ligament tissue, cartilage tissue, annulus fibrosus and nucleus pulposus.

The term "seeding" as used herein refers to plating, placing and/or dropping the cells of the invention (e.g., MSCs) within, under or on the matrix or the hydrogel of the invention.

The concentration of the seeded cells depends on the type of cells, the concentration of the matrix or hydrogel's components and the intended use. For example, seeding can be effected at a concentration range of $1 \times 10^5$-$1 \times 10^7$ cells per 50 µl-100 µl of hydrogel solution, e.g., $1$-$10 \times 10^6$ cells per 50 µl of hydrogel volume.

According to some embodiments of the invention, the tissue is generated ex vivo. As used herein, the phrase "ex vivo" refers to living cells which are derived from an organism and which are growing (or cultured) outside of the living organism, preferably, outside the body of a vertebrate, a mammal, or human being.

The method according to some embodiments of the invention, further comprising culturing the cells comprised in the matrix (e.g., following seeding the cells) under conditions, which allow tissue formation (e.g., connective tissue formation). Such conditions may include tissue culture medium, temperatures, gas concentration (e.g., $CO_2$, $O_2$), humidity, static or dynamic culturing conditions, which enable or induce proliferation, differentiation and/or migration of the cells (e.g., stem cells) and formation of a tissue.

The culture medium may be supplemented with minerals, amino acids and/or nutrients, or further with serum and/or growth factors.

Following seeding, the matrices or the hydrogels are routinely examined using a microscope (e.g., an inverted microscope, an axioplan light microscope or an electronic microscope) for evaluation of cell growth, spreading and tissue formation.

It should be noted that the ex vivo formed tissue (e.g., connective tissue) can be further implanted in a subject in need of tissue regeneration and/or repair (e.g., tissue grafting). In such cases the cells seeded within the matrix or the hydrogel can be derived from the treated individual (autologous source, e.g., autologous adult stem cells, obtained from the body of the subject such as from bone marrow or adipose tissue) or from allogeneic sources such as embryonic stem cells which are not expected to induce an immunogenic reaction in the implanted subject. Xenographic cells are also contemplated by the invention.

Thus, according to an aspect of some embodiments of the invention there is provided a method of treating a subject having a pathology characterized by diseased, damaged or loss of tissue. The method is effected by implanting in the subject the tissue generated according to the method of the invention, thereby treating the subject having the diseased, damaged or loss of tissue.

The phrase "treating" refers to inhibiting or arresting the development of a disease, disorder or condition and/or causing the reduction, remission, or regression of a disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the term "subject" refers to an animal, preferably a mammal such as a human being at any age. According to some embodiments of the invention, the term encompasses an individual who is in need for tissue regeneration and/or repair, as described below.

As used herein the phrase "pathology characterized by diseased, damaged or loss of tissue" refers to any disorder, disease or condition exhibiting a tissue damage (i.e., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration.

For example, pathologies characterized by diseased, damaged or loss of tissue which can be treated by the method of the invention include, but are not limited to, a critical size bone defect (Patel Z. S. et al., Bone. 2008 43:931-40. Epub 2008 Jul. 14); bone cancer; non-union fracture(s); osteoporosis; periodontal disease or defect; osteolytic bone disease; post-plastic surgery; post-orthopedic implantation; post neurosurgical surgery that involves calvaria bone removal; alveolar bone augmentation procedures; pathology or condition requiring spine fusion; vertebral fractures; tendon/ligament tissue tear due to trauma or inflammatory conditions; diseased, loss or injured cartilage due to rheumatoid arthritis, osteoarthritis, trauma, cancer surgery or for cosmetic surgery; diseased, loss or injured intervertebral disc tissues including nucleus pulposus and annulus fibrosus (nucleus pulposus degeneration, annulus fibrosus tears, or following nucleotomy or discectomy); articular cartilage defects (Zaslav K, et al., Am J Sports Med. 2009, 37:42-55. Epub 2008 Oct. 16); ligament injury (e.g., an anterior cruciate ligament injury; Fan H, et al., Biomaterials. 2008 August; 29:3324-37. Epub 2008 May 6); tendon injury (e.g., a major tendon rupture); injured muscle (Winkler T, et al., Tissue Eng Part A. 2008 July; 14(7):1149-60), skeletal muscle trauma, burn, wound (for wound repair), and the like.

As used herein the term "implanting" refers to placing (administering) the matrix or matrix with cells comprised therein (e.g., the ex vivo formed tissue, the hydrogel matrix) in the desired location within the body (e.g., in site). Methods of implanting grafts such as the matrix of the invention into a subject are known in the art. For example, the matrix can be implanted subcutaneously, intradermally, or into any body cavity (e.g., abdomen). The graft can be implanted in situ in the damaged tissue area. The matrix hydrogel (with or without cells) can be implanted in the subject by injection (e.g., using needle), using a suitable delivery mean such as by a catheter or a cannula; the cells may be independently implanted by injection, infusion, catheter or cannula, subcutaneously, intradermally, intramuscularly, into a body cavity and the like.

Those of skills in the art are capable of determining when and how to implant the matrix or the hydrogel to thereby induce tissue formation within the subject. See for example, Artzi Z, et al., 2005, J. Clin. Periodontol. 32: 193-9; Butler C E and Prieto V G, 2004, Plast. Reconstr. Surg. 114: 464-73.

According to some embodiments of the invention, the implantation site is where the tissue should be generated from the stem cells (e.g., adult stem cells, MSCs) such as a ligament, tendon, cartilage, intervertebral disc or bone tissue.

It should be noted, that the matrix of the invention can be implanted directly in the subject to thereby induce in vivo (i.e., within the living organism, e.g., a living human being) tissue regeneration and/or repair. Implantation of the matrix can be performed near, at, on or underneath the diseased, damaged, ischemic or loss of tissue of the subject. In addition, the matrix can be implanted at hypoxic sites (e.g., a tissue or an organ which suffers from low oxygen availability and/or ischemia).

According to this aspect of the invention, the matrix (e.g., in a dry, wetted, hydrogel, fiber or sponge form) can be implanted into the subject as is, or can be seeded with cells prior to implantation in the subject so as to enable proliferation, differentiation and/or migration of the cells (e.g., MSCs) within the matrix. Additionally or alternatively, the matrix can be implanted in the subject concomitantly with implantation of the cells into the subject. Still additionally or alternatively the matrix can be first implanted in the subject and then be supplemented with cells, administered at the site of implantation. Still additionally or alternatively, the matrix can be implanted into the subject as is so as to enable the proliferation, differentiation and/or migration of the subject's endogenous cells (e.g., cells from an adjacent tissue, such as stem cells, bone marrow cells or blood cells) in or on the matrix.

For example, in order to induce bone formation, regeneration and/or repair, the matrix of the invention can be embedded with MSCs of an autologous source (e.g., by suspending the matrix hydrogel with the cells or with a bone marrow aspirate comprising same) and then implanted directly at the target site (e.g., in the injured or diseased bone).

The compositions, the matrix and/or the hydrogel of the invention may, if desired, be presented in a pack or dispenser device, such as an FDA approved kit, or an article-of-manufacturing (with packaging material), which may contain one or more unit dosage forms containing the active ingredient. The pack may, for example, comprise metal or plastic foil, such as a blister pack. The pack or dispenser device may be accompanied by instructions for administration, implantation and/or for ex vivo or in vivo forming, regenerating and/or repairing a tissue and/or treating a subject. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. The compositions, matrix or hydrogel of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Cell Culture—Tet-off BMP-2 mesenchymal stem cells (MSCs), C3H10T1/2 derived cell line that was genetically engineered to express the recombinant human bone morphogenetic protein (rhBMP-2) gene (GenBank Accession No. P12643; SEQ ID NO:26) under a tet-off regulation, were generated as described (Moutsatsos, Turgeman et al. 2001). Briefly, cells from the C3H10T1/2 MSC line were transfected with a ptTATop-BMP-2 plasmid vector encoding for both a tetracycline transactivator and rhBMP-2. The inducible human BMP-2 expression vector, ptTATop-BMP-2, has a bidirectional promoter (TATA sequence) and consists of six tetracycline operators flanked by two transcriptional units with opposite orientations. In this vector, the level of the transactivator, which activates the bidirectional promoter, as well as the expression of hBMP-2 can be regulated by doxycycline, yielding higher levels of gene expression as well as a greater frequency of inducible clones. Cells were cultured in Dulbecco's Modified Eagle Medium with 4.5 gm/L D-glucose (DMEM) (Biological industries, Israel) containing 10% fetal calf serum (FCS) (Biological Industries, Israel), 100 units/ml penicillin-streptomycin (Biological Industries), 2 mM L-glutamine (Biological industries) and 1 µg/ml Doxycycline (Sigma) in order to prevent hBMP-2 expression during the culture period. Tet-off BMP2 MSCs that were genetically engineered to constantly express both luciferase and GFP reporter genes were prepared (designated as Tet-off BMP2 Luc/GFP cells) using retrovirus based vectors (Honigman, A., et al., 2001, Mol Ther 4, 239-249; Mostoslavsky, G., et al., 2005, Mol Ther 11, 932-940). Those cells were cultured in the same conditions as the Tet-off BMP2 cells.

Hydrogel Formulations:

Fibrin gel was prepared according to manufacturer's protocol (Tisseel, Baxter, Austria). Fibrin was diluted in sterile saline to reach a 46 mg/ml concentration. In order to reach coagulation, fibrin solution was mixed with thrombin (5 IU (international units)/ml) and cells just before implantation.

Silk gel was formed from *Bombyx mori* (Linne, 1758) cocoons boiled for 30 minutes in an aqueous solution of 0.02 M $Na_2CO_3$ and then rinsed thoroughly with water to extract glue-like sericin proteins. The extracted silk was dissolved in 9.3 M LiBr (Lithium bromide) solution. The silk fibroin aqueous solution was dialyzed against a 10 weight % polyethylene glycol (PEG) (10,000 g/mol) solution at room temperature in order to achieve 20% (w/w) concentration. Prior to use, silk gel was autoclaved for 15 minutes in 121° C. and mixed with sodium bicarbonate (1 M) in a 6/4 ratio (v/v) in order to achieve a pH of 7.4.

Ectopic implantations—At near confluency, Tet-off BMP2 cells or Tet-off BMP2 Luc/GFP cells were trypsinized and counted using the trypan blue exclusion method. Aliquots of cells (one million Tet-off BMP2 cells or 3 million Tet-off BMP2 Luc/GFP cells) were resuspended in 50111 of fibrin or silk gel. Five, 10 or 20% [weight per volume (w/v)] Heptacosafluorotributylamine (Perfluorotributylamine, PFTBA, Sigma catalogue number H5262; Sigma-Aldrich, St Louis, Mo., USA) was added to the hydrogel just before implantations.

The Institutional Animal Care and Use Committee approved all procedures consistent with the guide for the care and use of laboratory animals. All animals were provided with water and food ad libitum through out the duration of the study. The cell-hydrogel mixture was injected subcutaneously in 8 weeks old female C3H/HeN mice, as follows: mice were anesthetized with a mixture of xylazine and ketamine (0.15% xylazine and 0.85% ketamine), which was injected intraperitoneally (i.p.) at 1 µl/g body weight. The area of injection was shaved and cleaned using 70% ethanol. Using 27G tuberculin syringe the cells-gel mixture was injected subcutaneously. Each mouse received 3 or 4 implants, consistent of 50 µl hydrogel in which cells and PFTBA were mixed. Mice where sacrificed after two weeks, and implants were harvested and fixed in 4% formalin.

Analysis of bone formation using micro CT imaging—In order to quantify bone formation in the ectopic implants, a high-resolution µCT system, Desktop µCT 40 (Scanco Medical A G, Bassersdorf, Switzerland) was used. Micro-tomographic slices were acquired at 1000 projections and reconstructed at a spatial nominal resolution of 12 µm. A constrained 3-D Gaussian filter ($\sigma=0.8$ and support=1) was used to partly suppress the noise in the volumes. The mineralized tissue was segmented from the hydrogel using a global thresholding procedure (Muller, R., and Ruegsegger, P. 1997, *Stud Health Technol Inform* 40, 61-79). In addition to the visual assessment of structural images, morphometric indices were determined from the microtomographic datasets using direct 3D morphometry (Hildebrand, T., 1999, *J Bone Miner Res* 14, 1167-1174). Structural metrics measured using microCT are closely correlated with those measured using standard histomorphometry (Muller, R., et al., 1998, *Bone* 23, 59-66). The following morphometric indices were determined for the newly formed bone: (i) volume of bone tissue; (ii) bone mineral density; (iii) trabecular thickness; (iv) anisotropy; (v) bone volume density and (vi) trabecular separation.

Imaging of cell viability in vivo—Tet-off BMP2 Luc/GFP Cell viability in the ectopic implants was quantified using the BLI system as was described (Bar, Zilberman et al. 2003). This CCCD tracking system (Roper Chemiluminescence Imaging System) consists of a CCCD camera (model LN/CCD-1300EB; Roper Scientific Inc.) equipped with an ST-133 controller and a 50-mm Nikon lens (Nikon Inc.). In this system, a pseudocolor image represents light intensity (blue signifies least intense and red most intense). The integrated light is the result of 2-minute exposure and acquisition. This CCCD camera converts photons to electrons with an efficiency of approximately 90% in the wavelength emission range of luciferin and converts approximately 1.8 electrons per count. Thus, every count represents 2 photons. The measurement is a total integrated signal of a constant exposure interval. Whenever the exposure conditions (including time, F-stop, position of stage, binding ratio, and time after injection with luciferin) are kept identical, the measurements are comparable. The measurement can be verified by using a progressively larger region of interest (ROI) and by subtracting background readings. An increase in the ROI has no appreciable effect on the total intensity that is measured. Before light detection, the mice were anesthetized with a ketamine-xylazine mixture, which is injected intraperitoneally at 1 µl/g body weight. Ten minutes before monitoring the light emission, the animals were given intraperitoneal injections of beetle luciferin (Promega Madison, Wis., USA) in phosphate buffer-saline (PBS; 126 mg/kg body weight) in order to allow for luciferase activity to reach its peak (Bar, I., et al., 2003, *Journal of Bone and Mineral Research* 18, 570-578). It usually takes 10 minutes for luciferase activity to reach its peak. After the image is superimposed in real time over the grayscale image of the animal, it was placed in a dark box, which is supplemented with a controlled light so that pictures of the background image could be obtained. The animal was then exposed to the CCCD system and the composite image was transferred to a personal computer by using a plug-in module for further analysis.

In addition, cell viability was monitored in real time via GFP expression using a novel in vivo fibered confocal microscopy imaging system, the Cell-Vizio® S-Series endoscopic micro imaging system (Mauna Kea Technologies, USA). This system is equipped with 650 μm objective lens at the tip of the endoscope and 5 micron lateral resolution (Snedeker, Pelled et al. 2006). For this purpose the Cell-Vizio® probe was inserted into the ectopic implants and the fluorescence signal was recorded.

Cell survival assessment using quantitative PCR (qPCR)—In order to assess cell survival implants of tet-off BMP2 Luc/GFP were harvested at day 7. The implants were snap frozen in liquid nitrogen and homogenized using pestle and mortar. Total DNA was isolated from the implants using the Wizard Genomic DNA Purification Kit (Promega, Madison, Wis., USA) according to manufacturer's protocol. Luc copy number in the different samples was determined using the polymerase chain reaction (PCR) with the aid of the ABI Prism®D 7300 Sequence Detection System (Applied Biosystems, CA, USA).

Osteocalcin gene expression in vivo—In order to analyze the effect of PFTBA supplementation on osteocalcin gene expression in vivo, transgenic mice (Oc-Luc), which harbor the Luc gene under the control of the osteogenic tissue-specific promoter, osteocalcin (Bar, Zilberman et al. 2003) were utilized. In order to monitor Luc activity in real-time a quantitative, the BLI system with the non-invasive cooled charge-coupled device (CCCD) camera was used. In this model, osteogenic activity in the transgenic mice was reported by Luc expression, which is activated by the osteocalcin promoter. This activity is detected by the CCCD as an emitted light following an injection of luciferin. The result values were normalized to constitutive tail expression of Luc, as previously described (Bar, Zilberman et al. 2003), so that the different mice that express the transgene with different intensities could be compared. In this experiment, $1 \times 10^6$ tet-off BMP2 cells in fibrin gel supplemented with 5 or 10% PFTBA, or not supplemented at all were implanted. Osteocalcin expression was monitored at days 5, 7 and 14 post implantation, since preliminary studies suggest no Luc signal at day 2.

Radial defect regeneration—Radial nonunion fracture was created as previously described (Moutsatsos, I. K., et al., 2001, *Mol Ther* 3, 449-461). Briefly, C3H/HeN female mice aged 6-8 weeks (n=16) were anesthetized using ketamine-xylazine mixture injected intraperitoneal. The skin of the forelimb was swabbed with isopropyl alcohol (70%). The skin was cut and 2.5 mm-long defect was created in the radius bone. Approximately one million Tet-off BMP2 cells were suspended in fibrin gel (Baxter) and supplemented with 5 or 10% PFTBA (Sigma, n=5 for each group) or not supplemented at all (n=6). The cell-gel mixture was incubated for 5 minutes in room temperature (RT) under sterile conditions to allow the fibrin to gel, and was subsequently implanted into the defect site. The mice were sacrificed 2 weeks post-transplantation; limbs were harvested and scanned using the μCT in order to analyze bone formation.

A quantitative morphometric analysis of the bone formation in nonunion fractures, was undertaken using μCT as previously described (Tai, K., et al., 2008, *Tissue Eng Part A* 14, 1709-1720). Mouse forelimbs, including ulna and radius, as well as native muscle and soft tissue were scanned using a Desktop Cone-Beam Micro-CT Scanner (μCT 40; Scanco Medical AG, Bruttisellen, Switzerland) at a spatial nominal resolution of 20 mm. A constrained 3D Gaussian filter (sigma=0.8 and support=1) was used to partly suppress the noise in the volumes. The bone tissue was segmented from marrow and soft tissue using a global thresholding procedure. In the nonunion fracture site, the evaluation was done only in the central 2-mm of the bone defect, including only newly formed bone. Morphometric indices were determined as described earlier.

Posterior spinal fusion—C3H/HeN mice were anesthetized by administration of an intraperitoneal injection of a xylazine-ketamine mixture (ketamine 100 mg/kg and xylazine 3.3 mg/kg). Aliquots of $5 \times 10^6$ tet-off BMP2 cells were suspended in 50 μl of fibrin gel (Tisseel kit; Baxter, Vienna, Austria) supplemented with 10% of PFTBA or not supplemented at all. The cells were then injected bilaterally into the lumbar paravertebral muscle of each C3H10T1/2 mouse as previously described (Hasharoni, A., et al., 2005, *J Neurosurg Spine* 3, 47-52; Sheyn, D., et al., 2008, *Stem Cells* 26, 1056-1064). Hence, each mouse received two injections, one on each side. After three or six weeks, the mice were sacrificed and spines were harvested. Spines were scanned using a μCT Scanner (μCT 40; Scanco Medical AG, Bassersdorf, Switzerland). Microtomographic slices were acquired at 1000 projections and reconstructed at a spatial nominal resolution of 16 μm. Newly formed bone was separated from the native bone using manual contouring method. As bone reference the posterior portions of lumbar vertebrae that were contour in the same method were used. The following morphometric indices were determined using direct 3D morphometry for the newly formed bone and the control tissue: volume of mineralized bone tissue in mm3 (BV); connectivity density; bone volume density—determined by BV/TV ratio; average trabecular thickness in mm [Direct (DT) Trabecular (Tb)–Thickness (Th) mm].

Histological analysis of bone formation—Harvested ectopic implants and regenerated limbs were processed for histology and stained as described (Sheyn, Kimelman-Bleich et al. 2007). In short, samples were fixed in 70% ethanol, passed through a graded series of ethanols, and embedded in paraffin. Sections 5-8 μm thick were cut from each paraffin block using a motorized microtome (Leica Microsystems, Wetzlar, Germany). Masson trichrom staining was performed in order to evaluate the histomorphology of the mineralized tissue.

Statistical analysis—Two-tails student's T-test was used in order to determine significant difference between experimental and control groups, which was set at P<0.05. Results are presented as mean±standard error.

Example 1

MSCs Contained in Gels Supplemented with the Oxygen Carrier PFTBA Induce Increased Bone Formation Experimental Results Effect of PFTBA on ectopic bone formation—One million Tet-off BMP2 cells were suspended in fibrin or silk gel which were supplemented with 0%, 5% or 10% PFTBA (w/v). The silk gel implants included also a group supplemented with 20% PFTBA (w/v). Two weeks after subcutaneous implantation the implants were harvested and bone formation was analyzed using the micro CT. The volume of the ectopic bone generated by the fibrin gel implants (which include MSCs) that were supplemented with 10% PFTBA was significantly higher than that of the ectopic bone generated by fibrin gels implants (which include MSCs) that were not supplemented with PFTBA (2-tailed T-test, P<0.05, n=15-16 implants). While the average bone volume in the no PFTBA group (0% PFTBA) was 0.7±0.2 mm$^3$ (mean±standard error), the bone volume of the 5% PFTBA group was 0.98±0.26 mm$^3$, and the bone volume of the 10% PFTBA group was 1.77±0.47 mm$^3$, yielding a 2.5-fold increase in bone volume, compared with the 0% PFTBA group (FIG. 1A). When using the silk implants (with MSCs) significant differences were found in the volume of the ectopic bone between the no PFTBA (0% PFTBA) and the 20% PFTBA groups 1-tailed T-test, p=0.033. n=13 implants in 5 mice for the no PFTBA group, 15 implants in 5 mice for the 5% PFTBA group, 16 implants in 6 mice for the 10% PFTBA group and 12 implants in 4 mice for the 20% group; FIG. 1B]. FIGS. 1C-E display representative μCT images of the ectopic bone formed in the different fibrin groups. FIGS. 1F-I display representative μCT images of the ectopic bone formed in the different silk groups. All other morphometric indices (bone mineral density and bone volume density) were similar between all groups. No histological difference was found between implants in each of the three groups, including bone, hypertrophic cartilage and born marrow (FIGS. 1J-L).

Example 2

Gels Supplemented with the Oxygen Carrier PFTBA Induce Increased Cell Survival

Experimental Results

Effect of PFTBA on cell survival in ectopic implants—Three and 7 days post subcutaneous (S.C.) implantation of tet-off BMP2 Luc/GFP cells-seeded hydrogels, cell survival was monitored using the BLI system. On day 3 post implantation, luciferase activity was significantly higher in the group of PFTBA-containing hydrogels [including both the 10% and 5% PFTBA groups; 21,519±2,047 integrated light units (ILU)], over the group of no-PFTBA containing hydrogels (16,273±1,803 ILU; 1-tailed T-test, P<0.05, n=15 implants for the no-PFTBA group, and 25-26 implants for the PFTBA-containing group). On day 7 post-implantation, no significant difference between the groups was found (FIG. 2A). FIGS. 2B-D depict representative images of ectopic implants of fibrin gel containing Tet-off BMP2 Luc/GFP cells at day 3 after implantation.

Example 3

MSCs Contained in Gels Supplemented with the Oxygen Carrier PFTBA Exhibit a Paracrine Effect on Host Osteocalcin Gene Expression Experimental Results Paracrine effect of PFTBA on host osteocalcin gene expression—In order to further analyze the effect of PFTBA addition on osteocalcin expression in vivo during Tet-off BMP2 MSC induced osteogenesis, one million Tet-off BMP2 cells were suspended in fibrin gel supplemented with 5 or 10% PFTBA (v/v) or not supplemented with PFTBA at all. The cells were implanted S.C. in OC/Luc Tg mice. In this transgenic mice system, the Luciferase gene is expressed through the osteocalcin promoter, so that host osteogenic activity can be monitored non-invasively (Iris, B., et al., 2003, J Bone Miner Res 18, 570-578). Preliminary experiments showed that no Luc expression was noted at day 2 post-implantation (data not shown), accordingly, Luc expression was monitored at days 5, 7 and 14 post implantation. Bioluminescence was recorded using the BLI system. In accordance with the bone volume analysis results that noted enhanced bone formation in PFTBA supplemented implants, osteocalcin activity in PFTBA supplemented implants was significantly enhanced on day 5 post-implantation with 2.76±0.48 relative light units (RLU; implant/tail) in the PFTBA-containing group as compared to 1.29±0.35 RLU (1-tailed T-test, P<0.05, n=7-9 implants for the no PFTBA group, and 19-25 implants for the PFTBA-containing group). On day 7 and 14, no significant difference was noted between the experimental groups. It is noteworthy that albeit not significant, reported osteocalcin expression was higher in the with PFTBA-containing group as compared with the no PFTBA group, throughout the experiment length (FIG. 3A). FIGS. 3B-D display representative images from the three groups at day 5.

Example 4

MSCs Contained in Gels Supplemented with the Oxygen Carrier PFTBA Induce Increased Radius Bone Defect Regeneration Experimental Results Effect of PFTBA on radius bone defect regeneration—Tet-off BMP2 MSC were implanted into a 2.5-mm defect created in the radius bone of C3H mice (n=16). Implants were supplemented with 5 or 10% PFTBA (w/v) or no PFTBA (n=6 for no PFTBA, n=5 for 10 and 5% group each). Radii were harvested after 14 days, and μCT was utilized in order to analyze new bone formation. Three-dimensional reconstruction of the mice limbs revealed bridging of the bone defect in all groups (FIG. 4D). While no significant difference in the volume of bone formed was found between the different groups (FIG. 4A), a significant elevation in bone mineral density and in trabecular thickness was evident in PFTBA enriched radii versus unsupplemented implants (FIGS. 4B and C). Trabecular thickness was elevated by 1.3-fold when compared between the no-PFTBA group and the 5 or 10% PFTBA-containing groups (FIG. 4B). A similar 1.1-1.2 elevation was noted in BMD of the formed bone when supplemented and non-supplemented groups were compared (FIG. 4C).

Example 5

MSCs Contained in Gels Supplemented with the Oxygen Carrier PFTBA Induce Increased Posterior Spinal Fusion Experimental Results Effect of PFTBA on cell—mediated posterior spinal fusion—Tet-off BMP2 cells in PFTBA supplemented (10%) or not supplemented fibrin gel were injected into the lumbar paravertebral muscle of C3H mice. The spines were sacrificed after three (n=11 for the 10% PFTBA group, 8 for the no PFTBA group) or six weeks (n=10 for both groups) and bone formation was analyzed using the μCT. The analysis revealed a significant elevation in bone volume in the 10% PFTBA group at 6 weeks post implantation, compared with the no PFTBA group with 50.86±4.27 mm$^3$ bone created in the no PFTBA group, and 70.71±2.7 mm$^3$ formed in the 10% PFTBA group (FIGS. 5A-E). Interestingly, this difference was not noted at week 3 post-implantation. At that time, however, a significant difference was noted in several structural parameters. Connectivity density, bone volume density and trabecules number ware elevated in the 10% PFTBA-containing group compared with the no PFTBA group. Average connectivity density was elevated by 1.29-fold, bone volume density was elevated by 1.25-fold and trabecular number by 1.44-fold increase (FIGS. 5F-H).

Example 6

MSCs Contained in Gels Supplemented with the Oxygen Carrier PFTBA are Exposed to Higher Oxygen Level and Display Less Cell Death Experimental Results Effect of PFTBA on cell survival and oxygen levels—$10^6$ tet-off BMP-2 MSCs were suspended in 100 µl fibrin gel and cultured in 35-mm plates. In these conditions, the inner region of the hydrogel is hypoxic (data not shown). The experimental groups included hydrogels which included 0% or 10% PFTBA (w/v). Cell death was measured using the LDH release cytotoxicity assay on Days 1, 3, 7 and 14. The results indicate that significantly fewer cells died in the PFTBA-supplemented hydrogels on days 1 and 3 after cell seeding (FIG. 6A). Note that cytotoxicity was reduced over time, probably since nutrients and oxygen supply were more available to the remaining surviving cells. In a separate experiment, oxygen levels were measured in the center of MSC-loaded gels ($5^4$ cells in 300 µl fibrin gel) using the Microx TX3 oxygen sensor (Presens, Precision Sensing GmbH, Regensburg, Germany). The results show that although MSCs consumed the oxygen in the center of the gel quite rapidly, significantly higher oxygen tension was evident in PFTBA-supplemented hydrogels (till six hours post seeding, $P<0.05$, $n=5$, FIG. 6B), which could explain the increased cell survival seen in FIG. 6A.

Analysis and Discussion

The present study showed that perfluorocarbons synthetic oxygen carriers can significantly increase bone formation in ectopic transplantation. When ectopic bone volume was analyzed, a significant elevation in the amount of ectopic bone in the PFTBA supplemented groups was observed in comparison with the un-supplemented control. These results clearly indicate that supplementation of the hydrogel scaffold with the perfluorocarbons synthetic oxygen carrier on which tet-off BMP2 cells were seeded resulted in robust bone formation. Other morphometric indices such as bone mineral density etc. were not significantly different between the groups, indicating that only bone quantity was affected from the PFTBA supplementation.

Analysis of the cell viability in the ectopic implants, using the reporter genes Luciferase and GFP, revealed that cell viability was significantly higher in the PFTBA supplemented groups at day 3 compared with the un-supplemented control. Those results suggest that one of the main factors on which PFTBA effects is cell viability and survival in the implant.

The effect of PFTBA supplementation on osteocalcin expression was studied using a transgenic mice strain that allows for non-invasive monitoring of the osteocalcin gene expression during implant maturation. Osteocalcin is a bone tissue-specific protein expressed by osteoblasts, odontoblasts, and hypertrophic chondrocytes at the onset of tissue mineralization. The results presented here show that luciferase activity, which indicates osteocalcin expression, was elevated significantly in the PFTBA supplemented groups in comparison with the non-supplemented control at the beginning of bone formation (e.g., day 5 post implantation). Not only that more bone formed, osteocalcin expression, one of the main genes involved with bone formation was elevated as well.

Implantation of the tet-off BMP2 cells in a radius non-union bone defect revealed significantly higher trabecular thickness and bone mineral density in the 5% and 10% PFTBA-supplemented groups compared with the no PFTBA group. When tested in a cell mediated posterior spinal fusion model, in which tet-off BMP2 cells were implanted into the lumbar paravertebral muscle of C3H mice, PFTBA supplementation (10%) generated a significant elevation in trabecular thickness, bone volume density and connectivity density 3 weeks after implantation. Bone volume was significantly higher in the PFTBA supplemented implants 6 weeks after implantation. These data suggests that the effect of PFTBA addition to the cell scaffold could be observed long after the initial effect on cell survival.

This study shows, for the first time, that scaffolds which comprise oxygen carriers and MSC enhance ectopic bone formation, by elevating cell survival and avoiding cell death and loss of osteogenic potential. Furthermore, this study demonstrates the potential benefit of using PFTBA supplementation in bone regeneration model and in posterior spinal fusion. These results could pave the way for novel therapeutic strategies that can be used in order to achieve bone regeneration or bone formation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Grayson, W. L., Zhao, F., Izadpanah, R., Bunnell, B., and Ma, T. (2006) Effects of hypoxia on human mesenchymal stem cell expansion and plasticity in 3D constructs. J Cell Physiol 207, 331-339;
2. Martin-Rendon, E., Hale, S. J., Ryan, D., Baban, D., Forde, S. P., Roubelakis, M., Sweeney, D., Moukayed, M., Harris, A. L., Davies, K., and Watt, S. M. (2006) Transcriptional profiling of human cord blood CD133+ and cultured bone marrow mesenchymal stem cells in response to hypoxia. Stem Cells;
3. D'Ippolito, G., Diabira, S., Howard, G. A., Roos, B. A., and Schiller, P. C. (2006) Low oxygen tension inhibits osteogenic differentiation and enhances stemness of human MIAMI cells. Bone 39, 513-522;
4. Muhonen, A., Haaparanta, M., Gronroos, T., Bergman, J., Knuuti, J., Hinkka, S., and Happonen, R. P. (2004) Osteoblastic activity and neoangiogenesis in distracted bone of irradiated rabbit mandible with or without hyperbaric oxygen treatment. Int J Oral Maxillofac Surg 33, 173-178;

5. Huang, Y. C., Kaigler, D., Rice, K. G., Krebsbach, P. H., and Mooney, D. J. (2005) Combined angiogenic and osteogenic factor delivery enhances bone marrow stromal cell-driven bone regeneration. J Bone Miner Res 20, 848-857;
6. Klopper, J., Lindenmaier, W., Fiedler, U., Mehlhom, A., Stark, G. B., and Finkenzeller, G. (2008) High efficient adenoviral-mediated VEGF and Ang-1 gene delivery into osteogenically differentiated human mesenchymal stem cells. Microvasc Res 75, 83-90;
7. Khattak, S. F., Chin, K. S., Bhatia, S. R., and Roberts, S.C. (2007) Enhancing oxygen tension and cellular function in alginate cell encapsulation devices through the use of perfluorocarbons. Biotechnol Bioeng 96, 156-166;
8. Moutsatsos, I. K., Turgeman, G., Zhou, S., Kurkalli, B. G., Pelled, G., Tzur, L., Kelley, P., Stumm, N., Mi, S., Muller, R., Zilberman, Y., and Gazit, D. (2001) Exogenously regulated stem cell-mediated gene therapy for bone regeneration. Mol Ther 3, 449-461;
9. Radisic et al. 2008, Nat Protoc 3, 719;
10. Radisic et al. 2006, Tissue Eng 12, 2077;
11. Radisic et al. 2005, Am J Physiol Heart Circ Physiol 288, H1278;
12. Fraker et al. 2007, Stem cells 25: 3155-3164;
13. Chin K, et al., 2008, Biotechnol. Prog. 24(2):358-66. Epub 2008 Feb. 23.
14. WO 01/76507;

What is claimed is:

1. A method of inducing in vivo cartilage tissue regeneration and/or repair, comprising implanting a matrix in cartilage of a subject in need thereof, said matrix comprising a protein backbone, mesenchymal stem cells and an oxygen carrier, wherein said oxygen carrier is selected from the group consisting of a hemoglobin molecule, a hemoglobin molecule derivative and a perfluorocarbon molecule and wherein the subject suffers from or is diagnosed with a pathology selected from the group consisting of loss of cartilage, injured cartilage, osteoarthritis, diseased intervertabral disc tissue, loss of intervertebral disc tissue, injured intervertebral disc tissue, articular cartilage defect, thereby inducing the cartilage tissue regeneration and/or repair in said subject.

2. The method of claim 1, wherein said cells are embedded within said matrix.

3. The method of claim 1, wherein said backbone is made of a biodegradable or a biocompatible molecule.

4. The method of claim 1, wherein said protein backbone comprises a fibrin backbone or a silk backbone.

5. The method of claim 1, wherein said oxygen carrier is embedded within said backbone so that said oxygen carrier is unable to flow through, in or on said backbone.

6. The method of claim 1, wherein said perfluorocarbon molecule comprises perfluorotributylamine (PFTBA) molecule.

7. The method of claim 1, wherein a concentration of said perfluorocarbon molecule in the matrix is at least about 1% weight per volume (w/v).

8. The method of claim 4, wherein the matrix further comprises thrombin.

9. The method of claim 1, wherein said protein backbone is selected from the group consisting of fibrinogen, silk, PEGylated fibrinogen, collagen, PEGylated collagen, fibronectin, PEGylated fibronectin, fibrin, gelatin, albumin, elastin, and chondroitin-6-sulfate.

10. The method of claim 1, wherein said hemoglobin molecule derivative is selected from the group consisting of a crosslinked haemoglobin, polymerized haemoglobin and encapsulated haemoglobin.

11. The method of claim 1, wherein said hemoglobin comprises a recombinant hemoglobin.

12. The method of claim 1, wherein said cells are absorbed to said matrix.

13. The method of claim 1, wherein said cells are immobilized within or on said matrix.

14. The method of claim 1, wherein said matrix comprises a gel matrix.

15. The method of claim 1, wherein said tissue is under hypoxia.

16. The method of claim 1, wherein said perfluorocarbon molecule is selected from the group consisting of perfluorooctylbromide molecule, octafluoropropane molecule, perfluorohexane molecule, perfluorodecalin molecule, perfluorodichlorooctane molecule, perfluorodecane molecule, perfluorotripropylamine molecule, perfluorotrimethylcyclohexane molecule, perfluoroperhydrophenanthrene molecule, perfluoromethyladamantane molecule, perfluorodimethyladamantane molecule, perfluoromethyldecaline molecule, perfluorofluorene molecule, diphenyldimethylsiloxane molecule, hydrogen-rich monohydroperfluorooctane molecule, and alumina-treated perfluorooctane molecule.

17. The method of claim 1, wherein said perfluorocarbon molecule comprises perfluorodecalin molecule.

18. The method of claim 1, wherein said cells are genetically modified.

19. The method of claim 18, wherein said cells exogenously express morphogenetic proteins (BMP).

* * * * *

SEQUENCE LISTING

<160> NUMBER OF SEQ ID NOS: 30

<210> SEQ ID NO 1
<211> LENGTH: 866
<212> TYPE: PRT
<213> ORGANISM: Homo sapiens

<400> SEQUENCE: 1

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
```

```
            275                 280                 285
Pro Ser Ser Ala Gly Ser Trp Asn Ser Gly Ser Ser Pro Gly Ser
290                 295                 300
Thr Gly Asn Arg Asn Pro Gly Ser Ser Gly Thr Gly Thr Ala Thr
305                 310                 315                 320
Trp Lys Pro Gly Ser Ser Pro Gly Ser Thr Gly Ser Trp Asn Ser
                325                 330                 335
Gly Ser Ser Gly Thr Gly Ser Thr Gly Asn Gln Asn Pro Gly Ser Pro
                340                 345                 350
Arg Pro Gly Ser Thr Gly Thr Trp Asn Pro Gly Ser Ser Glu Arg Gly
                355                 360                 365
Ser Ala Gly His Trp Thr Ser Glu Ser Ser Val Ser Gly Ser Thr Gly
    370                 375                 380
Gln Trp His Ser Glu Ser Gly Ser Phe Arg Pro Asp Ser Pro Gly Ser
385                 390                 395                 400
Gly Asn Ala Arg Pro Asn Asn Pro Asp Trp Gly Thr Phe Glu Glu Val
                405                 410                 415
Ser Gly Asn Val Ser Pro Gly Thr Arg Arg Glu Tyr His Thr Glu Lys
                420                 425                 430
Leu Val Thr Ser Lys Gly Asp Lys Glu Leu Arg Thr Gly Lys Glu Lys
                435                 440                 445
Val Thr Ser Gly Ser Thr Thr Thr Thr Arg Arg Ser Cys Ser Lys Thr
450                 455                 460
Val Thr Lys Thr Val Ile Gly Pro Asp Gly His Lys Glu Val Thr Lys
465                 470                 475                 480
Glu Val Val Thr Ser Glu Asp Gly Ser Asp Cys Pro Glu Ala Met Asp
                485                 490                 495
Leu Gly Thr Leu Ser Gly Ile Gly Thr Leu Asp Gly Phe Arg His Arg
                500                 505                 510
His Pro Asp Glu Ala Ala Phe Phe Asp Thr Ala Ser Thr Gly Lys Thr
                515                 520                 525
Phe Pro Gly Phe Phe Ser Pro Met Leu Gly Glu Phe Val Ser Glu Thr
                530                 535                 540
Glu Ser Arg Gly Ser Glu Ser Gly Ile Phe Thr Asn Thr Lys Glu Ser
545                 550                 555                 560
Ser Ser His His Pro Gly Ile Ala Glu Phe Pro Ser Arg Gly Lys Ser
                565                 570                 575
Ser Ser Tyr Ser Lys Gln Phe Thr Ser Ser Thr Ser Tyr Asn Arg Gly
                580                 585                 590
Asp Ser Thr Phe Glu Ser Lys Ser Tyr Lys Met Ala Asp Glu Ala Gly
                595                 600                 605
Ser Glu Ala Asp His Glu Gly Thr His Ser Thr Lys Arg Gly His Ala
    610                 615                 620
Lys Ser Arg Pro Val Arg Asp Cys Asp Val Leu Gln Thr His Pro
625                 630                 635                 640
Ser Gly Thr Gln Ser Gly Ile Phe Asn Ile Lys Leu Pro Gly Ser Ser
                645                 650                 655
Lys Ile Phe Ser Val Tyr Cys Asp Gln Glu Thr Ser Leu Gly Gly Trp
                660                 665                 670
Leu Leu Ile Gln Gln Arg Met Asp Gly Ser Leu Asn Phe Asn Arg Thr
                675                 680                 685
Trp Gln Asp Tyr Lys Arg Gly Phe Gly Ser Leu Asn Asp Glu Gly Glu
    690                 695                 700
```

```
Gly Glu Phe Trp Leu Gly Asn Asp Tyr Leu His Leu Leu Thr Gln Arg
705                 710                 715                 720

Gly Ser Val Leu Arg Val Glu Leu Glu Asp Trp Ala Gly Asn Glu Ala
                725                 730                 735

Tyr Ala Glu Tyr His Phe Arg Val Gly Ser Glu Ala Gly Gly Tyr Ala
            740                 745                 750

Leu Gln Val Ser Ser Tyr Glu Gly Thr Ala Gly Asp Ala Leu Ile Glu
        755                 760                 765

Gly Ser Val Glu Glu Gly Ala Glu Tyr Thr Ser His Asn Asn Met Gln
770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
        835                 840                 845

Ala Asp Tyr Ser Leu Arg Ala Val Arg Met Lys Ile Arg Pro Leu Val
850                 855                 860

Thr Gln
865

<210> SEQ ID NO 2
<211> LENGTH: 644
<212> TYPE: PRT
<213> ORGANISM: Homo sapiens

<400> SEQUENCE: 2

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
            85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
            165                 170                 175

Ile Arg Ser Cys Arg Gly Ser Cys Ser Arg Ala Leu Ala Arg Glu Val
        180                 185                 190

Asp Leu Lys Asp Tyr Glu Asp Gln Gln Lys Gln Leu Glu Gln Val Ile
```

```
            195                 200                 205
Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
                260                 265                 270

Gly Ser Thr Ser Tyr Gly Thr Gly Ser Glu Thr Glu Ser Pro Arg Asn
                275                 280                 285

Pro Ser Ser Ala Gly Ser Trp Asn Ser Gly Ser Ser Gly Pro Gly Ser
290                 295                 300

Thr Gly Asn Arg Asn Pro Gly Ser Ser Gly Thr Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
                355                 360                 365

Ser Ala Gly His Trp Thr Ser Glu Ser Ser Val Ser Gly Ser Thr Gly
370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
                420                 425                 430

Leu Val Thr Ser Lys Gly Asp Lys Glu Leu Arg Thr Gly Lys Glu Lys
                435                 440                 445

Val Thr Ser Gly Ser Thr Thr Thr Arg Arg Ser Cys Ser Lys Thr
450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
                500                 505                 510

His Pro Asp Glu Ala Ala Phe Phe Asp Thr Ala Ser Thr Gly Lys Thr
                515                 520                 525

Phe Pro Gly Phe Phe Ser Pro Met Leu Gly Glu Phe Val Ser Glu Thr
                530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Ser Ser Thr Ser Tyr Asn Arg Gly
                580                 585                 590

Asp Ser Thr Phe Glu Ser Lys Ser Tyr Lys Met Ala Asp Glu Ala Gly
                595                 600                 605

Ser Glu Ala Asp His Glu Gly Thr His Ser Thr Lys Arg Gly His Ala
610                 615                 620
```

```
Lys Ser Arg Pro Val Arg Gly Ile His Thr Ser Pro Leu Gly Lys Pro
625                 630                 635                 640

Ser Leu Ser Pro

<210> SEQ ID NO 3
<211> LENGTH: 491
<212> TYPE: PRT
<213> ORGANISM: Homo sapiens

<400> SEQUENCE: 3

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
                20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350
```

```
Lys Ala His Tyr Gly Gly Phe Thr Val Gln Asn Glu Ala Asn Lys Tyr
            355                 360                 365

Gln Ile Ser Val Asn Lys Tyr Arg Gly Thr Ala Gly Asn Ala Leu Met
            370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
                420                 425                 430

Trp Tyr Asn Arg Cys His Ala Ala Asn Pro Asn Gly Arg Tyr Tyr Trp
                435                 440                 445

Gly Gly Gln Tyr Thr Trp Asp Met Ala Lys His Gly Thr Asp Asp Gly
            450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 4
<211> LENGTH: 437
<212> TYPE: PRT
<213> ORGANISM: Homo sapiens

<400> SEQUENCE: 4

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
                20                  25                  30

Asn Cys Cys Ile Leu Asp Glu Arg Phe Gly Ser Tyr Cys Pro Thr Thr
            35                  40                  45

Cys Gly Ile Ala Asp Phe Leu Ser Thr Tyr Gln Thr Lys Val Asp Lys
        50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
                100                 105                 110

Arg Lys Met Leu Glu Glu Ile Met Lys Tyr Glu Ala Ser Ile Leu Thr
            115                 120                 125

His Asp Ser Ser Ile Arg Tyr Leu Gln Glu Ile Tyr Asn Ser Asn Asn
        130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
```

```
                225                 230                 235                 240
        Phe Gly His Leu Ser Pro Thr Gly Thr Thr Glu Phe Trp Leu Gly Asn
                        245                 250                 255

Glu Lys Ile His Leu Ile Ser Thr Gln Ser Ala Ile Pro Tyr Ala Leu
                        260                 265                 270

Arg Val Glu Leu Glu Asp Trp Asn Gly Arg Thr Ser Thr Ala Asp Tyr
                        275                 280                 285

Ala Met Phe Lys Val Gly Pro Glu Ala Asp Lys Tyr Arg Leu Thr Tyr
                        290                 295                 300

Ala Tyr Phe Ala Gly Gly Asp Ala Gly Asp Ala Phe Asp Gly Phe Asp
        305                 310                 315                 320

Phe Gly Asp Asp Pro Ser Asp Lys Phe Phe Thr Ser His Asn Gly Met
                        325                 330                 335

Gln Phe Ser Thr Trp Asp Asn Asp Lys Phe Glu Gly Asn Cys
                        340                 345                 350

Ala Glu Gln Asp Gly Ser Gly Trp Trp Met Asn Lys Cys His Ala Gly
                        355                 360                 365

His Leu Asn Gly Val Tyr Tyr Gln Gly Gly Thr Tyr Ser Lys Ala Ser
                        370                 375                 380

Thr Pro Asn Gly Tyr Asp Asn Gly Ile Ile Trp Ala Thr Trp Lys Thr
        385                 390                 395                 400

Arg Trp Tyr Ser Met Lys Lys Thr Thr Met Lys Ile Ile Pro Phe Asn
                        405                 410                 415

Arg Leu Thr Ile Gly Glu Gly Gln Gln His Leu Gly Gly Ala Lys
                        420                 425                 430

Gln Ala Gly Asp Val
                        435

<210> SEQ ID NO 5
<211> LENGTH: 453
<212> TYPE: PRT
<213> ORGANISM: Homo sapiens

<400> SEQUENCE: 5

Met Ser Trp Ser Leu His Pro Arg Asn Leu Ile Leu Tyr Phe Tyr Ala
        1               5                   10                  15

Leu Leu Phe Leu Ser Ser Thr Cys Val Ala Tyr Val Ala Thr Arg Asp
                        20                  25                  30

Asn Cys Cys Ile Leu Asp Glu Arg Phe Gly Ser Tyr Cys Pro Thr Thr
                        35                  40                  45

Cys Gly Ile Ala Asp Phe Leu Ser Thr Tyr Gln Thr Lys Val Asp Lys
                50                  55                  60

Asp Leu Gln Ser Leu Glu Asp Ile Leu His Gln Val Glu Asn Lys Thr
        65                  70                  75                  80

Ser Glu Val Lys Gln Leu Ile Lys Ala Ile Gln Leu Thr Tyr Asn Pro
                        85                  90                  95

Asp Glu Ser Ser Lys Pro Asn Met Ile Asp Ala Ala Thr Leu Lys Ser
                        100                 105                 110

Arg Lys Met Leu Glu Glu Ile Met Lys Tyr Glu Ala Ser Ile Leu Thr
                        115                 120                 125

His Asp Ser Ser Ile Arg Tyr Leu Gln Glu Ile Tyr Asn Ser Asn Asn
                        130                 135                 140

Gln Lys Ile Val Asn Leu Lys Glu Lys Val Ala Gln Leu Glu Ala Gln
        145                 150                 155                 160
```

-continued

```
Cys Gln Glu Pro Cys Lys Asp Thr Val Gln Ile His Asp Ile Thr Gly
                165                 170                 175
Lys Asp Cys Gln Asp Ile Ala Asn Lys Gly Ala Lys Gln Ser Gly Leu
            180                 185                 190
Tyr Phe Ile Lys Pro Leu Lys Ala Asn Gln Gln Phe Leu Val Tyr Cys
        195                 200                 205
Glu Ile Asp Gly Ser Gly Asn Gly Trp Thr Val Phe Gln Lys Arg Leu
    210                 215                 220
Asp Gly Ser Val Asp Phe Lys Lys Asn Trp Ile Gln Tyr Lys Glu Gly
225                 230                 235                 240
Phe Gly His Leu Ser Pro Thr Gly Thr Thr Glu Phe Trp Leu Gly Asn
                245                 250                 255
Glu Lys Ile His Leu Ile Ser Thr Gln Ser Ala Ile Pro Tyr Ala Leu
            260                 265                 270
Arg Val Glu Leu Glu Asp Trp Asn Gly Arg Thr Ser Thr Ala Asp Tyr
        275                 280                 285
Ala Met Phe Lys Val Gly Pro Glu Ala Asp Lys Tyr Arg Leu Thr Tyr
    290                 295                 300
Ala Tyr Phe Ala Gly Gly Asp Ala Gly Asp Ala Phe Asp Gly Phe Asp
305                 310                 315                 320
Phe Gly Asp Asp Pro Ser Asp Lys Phe Phe Thr Ser His Asn Gly Met
                325                 330                 335
Gln Phe Ser Thr Trp Asp Asn Asp Asn Asp Lys Phe Glu Gly Asn Cys
            340                 345                 350
Ala Glu Gln Asp Gly Ser Gly Trp Trp Met Asn Lys Cys His Ala Gly
        355                 360                 365
His Leu Asn Gly Val Tyr Tyr Gln Gly Gly Thr Tyr Ser Lys Ala Ser
    370                 375                 380
Thr Pro Asn Gly Tyr Asp Asn Gly Ile Ile Trp Ala Thr Trp Lys Thr
385                 390                 395                 400
Arg Trp Tyr Ser Met Lys Lys Thr Thr Met Lys Ile Ile Pro Phe Asn
                405                 410                 415
Arg Leu Thr Ile Gly Glu Gly Gln Gln His His Leu Gly Gly Ala Lys
            420                 425                 430
Gln Val Arg Pro Glu His Pro Ala Glu Thr Glu Tyr Asp Ser Leu Tyr
        435                 440                 445
Pro Glu Asp Asp Leu
    450

<210> SEQ ID NO 6
<211> LENGTH: 396
<212> TYPE: PRT
<213> ORGANISM: Homo sapiens

<400> SEQUENCE: 6

Met Val Ala Gly Thr Arg Cys Leu Leu Ala Leu Leu Leu Pro Gln Val
1               5                   10                  15
Leu Leu Gly Gly Ala Ala Gly Leu Val Pro Glu Leu Gly Arg Arg Lys
            20                  25                  30
Phe Ala Ala Ala Ser Ser Gly Arg Pro Ser Ser Gln Pro Ser Asp Glu
        35                  40                  45
Val Leu Ser Glu Phe Glu Leu Arg Leu Leu Ser Met Phe Gly Leu Lys
    50                  55                  60
Gln Arg Pro Thr Pro Ser Arg Asp Ala Val Val Pro Pro Tyr Met Leu
65                  70                  75                  80
```

```
Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 7
<211> LENGTH: 3150
<212> TYPE: DNA
<213> ORGANISM: Homo sapiens

<400> SEQUENCE: 7
ccacaaaggg cacttggccc cagggctagg agagcgaggg gagagcacag ccacccgcct      60
cggcggcccg ggactcggct cgactcgccg gagaatgcgc ccgaggacga cggggcgcca     120
gagccgcggt gctttcaact ggcgagcgcg aatgggggtg cactggagta aggcagagtg     180
atgcgggggg gcaactcgcc tgcaccgag atcgccgccg tgcccttccc tggacccggc      240
gtcgcccagg atggctgccc cgagccatgg gccgcggcgg agctagcgcg gagcgcccga     300
```

```
ccctcgaccc ccgagtcccg gagccggccc cgcgcggggc cacgcgtccc tcgggcgctg    360
gttcctaagg aggacgacag caccagcttc tcctttctcc cttcccttcc ctgccccgca    420
ctcctccccc tgctcgctgt tgttgtgtgt cagcacttgg ctggggactt cttgaacttg    480
cagggagaat aacttgcgca ccccactttg cgccggtgcc tttgcccccag cggagcctgc    540 ttcgccatct ccgagcccca ccgcccctcc actcctcggc cttgcccgac actgagacgc    600
tgttcccagc gtgaaaagag agactgcgcg gccggcaccc gggagaagga ggaggcaaag    660
aaaaggaacg gacattcggt ccttgcgcca ggtcctttga ccagagtttt tccatgtgga    720
cgctctttca atggacgtgt ccccgcgtgc ttcttagacg gactgcggtc tcctaaaggt    780
cgaccatggt ggccgggacc cgctgtcttc tagcgttgct gcttccccag gtcctcctgg    840
gcggcgcggc tggcctcgtt ccggagctgg gccgcaggaa gttcgcggcg cgtcgtcgg    900 gccgcccctc atcccagccc tctgacgagg tcctgagcga gttcgagttg cggctgctca    960
gcatgttcgg cctgaaacag agacccaccc ccagcaggga cgccgtggtg cccccctaca   1020
tgctagacct gtatcgcagg cactcaggtc agccgggctc acccgcccca gaccaccggt   1080
tggagagggc agccagccga gccaacactg tgcgcagctt ccaccatgaa gaatctttgg   1140
aagaactacc agaaacgagt gggaaaacaa cccggagatt cttctttaat ttaagttcta   1200
tccccacgga ggagtttatc acctcagcag agcttcaggt tttccgagaa cagatgcaag   1260
atgctttagg aaacaatagc agtttccatc accgaattaa tatttatgaa atcataaaac   1320
ctgcaacagc caactcgaaa ttccccgtga ccagacttttt ggacaccagg ttggtgaatc   1380
agaatgcaag caggtgggaa agttttgatg tcaccccgc tgtgatgcgg tggactgcac   1440
agggacacgc caaccatgga ttcgtggtgg aagtggccca cttggaggag aaacaaggtg   1500
tctccaagag acatgttagg ataagcaggt ctttgcacca agatgaacac agctggtcac   1560
agataaggcc attgctagta acttttggcc atgatggaaa agggcatcct ctccacaaaa   1620
gagaaaaacg tcaagccaaa cacaaacagc ggaaacgcct taagtccagc tgtaagagac   1680 acccttgta cgtggacttc agtgacgtgg ggtggaatga ctggattgtg ctcccccgg   1740 ggtatcacgc cttttactgc cacggagaat gcccttttcc tctggctgat catctgaact   1800
ccactaatca tgccattgtt cagacgttgg tcaactctgt taactctaag attcctaagg   1860
catgctgtgt cccgacagaa ctcagtgcta tctcgatgct gtaccttgac gagaatgaaa   1920
aggttgtatt aaagaactat caggacatgg ttgtggaggg ttgtgggtgt cgctagtaca   1980
gcaaaattaa atacataaat atatatatat atatatattt tagaaaaaag aaaaaaacaa   2040
acaaacaaaa aaacccccacc ccagttgaca ctttaatatt tcccaatgaa gactttatt   2100 atggaatgga atgaaaaaa aaacagctat tttgaaaata tatttatatc tacgaaaaga   2160
agttgggaaa acaaatattt taatcagaga attattcctt aaagatttaa aatgtattta   2220
gttgtacatt ttatatgggt tcaaccccag cacatgaagt ataatggtca gatttatttt   2280
gtatttattt actattataa ccactttta ggaaaaaaat agctaatttg tatttatatg   2340
taatcaaaag aagtatcggg tttgtacata attttccaaa aattgtagtt gttttcagtt   2400
gtgtgtattt aagatgaaaa gtctacatgg aaggttactc tggcaaagtg cttagcacgt   2460
ttgctttttt gcagtgctac tgttgagttc acaagttcaa gtccagaaaa aaaaagtgga   2520
taatccactc tgctgacttt caagattatt atattattca attctcagga atgttgcaga   2580
gtgattgtcc aatccatgag aatttacatc cttattaggt ggaatatttg gataagaacc   2640
agacattgct gatctattat agaaactctc ctcctgcccc ttaatttaca gaaagaataa   2700
```

-continued

```
agcaggatcc atagaaataa ttaggaaaac gatgaacctg caggaaagtg aatgatggtt    2760
tgttgttctt ctttcctaaa ttagtgatcc cttcaagggg ctgatctgg ccaaagtatt     2820 caataaaacg taagatttct tcattattga tattgtggtc atatatattt aaaattgata    2880
tctcgtggcc ctcatcaagg gttggaaatt tatttgtgtt ttacctttac ctcatctgag    2940
agctctttat tctccaaaga acccagtttt ctaactttt gcccaacacg cagcaaaatt      3000
atgcacatcg tgttttctgc ccaccctctg ttctctgacc tatcagcttg cttttctttc    3060
caaggttgtg tgtttgaaca catttctcca atgttaaac ctatttcaga taataaatat      3120
caaatctctg gcatttcatt ctataaagtc                                     3150
```

<210> SEQ ID NO 8
<211> LENGTH: 438
<212> TYPE: PRT
<213> ORGANISM: Artificial sequence
<220> FEATURE:
<223> OTHER INFORMATION: FLAG tagged Rat SMAD8

<400> SEQUENCE: 8

```
Met Asp Tyr Lys Asp Asp Asp Lys His Pro Ser Thr Pro Ile Ser
1               5                   10                  15

Ser Leu Phe Ser Phe Thr Ser Pro Ala Val Lys Arg Leu Leu Gly Trp
            20                  25                  30

Lys Gln Gly Asp Glu Glu Lys Trp Ala Glu Lys Ala Val Asp Ser
        35                  40                  45

Leu Val Lys Lys Leu Lys Lys Lys Gly Ala Met Asp Glu Leu Glu
    50                  55                  60

Arg Ala Leu Ser Cys Pro Gly Gln Pro Ser Lys Cys Val Thr Ile Pro
65                  70                  75                  80

Arg Ser Leu Asp Gly Arg Leu Gln Val Ser His Arg Lys Gly Leu Pro
                85                  90                  95

His Val Ile Tyr Cys Arg Val Trp Arg Trp Pro Asp Leu Gln Ser His
            100                 105                 110

His Glu Leu Lys Pro Leu Glu Cys Cys Glu Phe Pro Phe Gly Ser Lys
        115                 120                 125

Gln Lys Glu Val Cys Ile Asn Pro Tyr His Tyr Arg Arg Val Glu Thr
    130                 135                 140

Pro Val Leu Pro Pro Val Leu Val Pro Arg His Ser Glu Tyr Asn Pro
145                 150                 155                 160

Gln Leu Ser Leu Leu Ala Lys Phe Arg Ser Ala Ser Leu His Ser Glu
                165                 170                 175

Pro Leu Met Pro His Asn Ala Thr Tyr Pro Asp Ser Phe Gln Gln Ser
            180                 185                 190

Leu Gly Pro Ala Pro Ser Ser Pro Gly His Val Phe Pro Gln Ser
        195                 200                 205

Pro Cys Pro Thr Ser Tyr Pro Gln Ser Pro Gly Ser Pro Ser Glu Ser
    210                 215                 220

Asp Ser Pro Tyr Gln His Ser Asp Phe Arg Pro Val Cys Tyr Glu Glu
225                 230                 235                 240

Pro Leu His Trp Cys Ser Val Ala Tyr Tyr Glu Leu Asn Asn Arg Val
                245                 250                 255

Gly Glu Thr Phe Gln Ala Ser Ser Arg Ser Val Leu Ile Asp Gly Phe
            260                 265                 270

Thr Asp Pro Ser Asn Asn Arg Asn Arg Phe Cys Leu Gly Leu Leu Ser
```

```
                275                 280                 285
Asn Val Asn Arg Asn Ser Thr Ile Glu Asn Thr Arg Arg His Ile Gly
    290                 295                 300

Lys Gly Val His Leu Tyr Tyr Val Gly Gly Glu Val Tyr Ala Glu Cys
305                 310                 315                 320

Val Ser Asp Ser Ser Ile Phe Val Gln Ser Arg Asn Cys Asn Tyr Gln
                    325                 330                 335

His Gly Phe His Pro Ala Thr Val Cys Lys Ile Pro Ser Gly Cys Ser
                340                 345                 350

Leu Lys Val Phe Asn Asn Gln Leu Phe Ala Gln Leu Leu Ala Gln Ser
                    355                 360                 365

Val His His Gly Phe Glu Val Val Tyr Glu Leu Thr Lys Met Cys Thr
                370                 375                 380

Ile Arg Met Ser Phe Val Lys Gly Trp Gly Ala Glu Tyr His Arg Gln
385                 390                 395                 400

Asp Val Thr Ser Thr Pro Cys Trp Ile Glu Ile His Leu His Gly Pro
                    405                 410                 415

Leu Gln Trp Leu Asp Lys Val Leu Thr Gln Met Gly Ser Pro His Asn
                420                 425                 430

Pro Ile Ser Ser Val Ser
                435

<210> SEQ ID NO 9
<211> LENGTH: 291
<212> TYPE: PRT
<213> ORGANISM: Artificial sequence
<220> FEATURE:
<223> OTHER INFORMATION: FLAG tagged Rat SMAD8 L+MH2

<400> SEQUENCE: 9

Met Asp Tyr Lys Asp Asp Asp Asp Lys Glu Tyr Asn Pro Gln Leu Ser
1               5                   10                  15

Leu Leu Ala Lys Phe Arg Ser Ala Ser Leu His Ser Glu Pro Leu Met
                20                  25                  30

Pro His Asn Ala Thr Tyr Pro Asp Ser Phe Gln Gln Ser Leu Gly Pro
            35                  40                  45

Ala Pro Pro Ser Ser Pro Gly His Val Phe Pro Gln Ser Pro Cys Pro
50                  55                  60

Thr Ser Tyr Pro Gln Ser Pro Gly Ser Pro Ser Glu Ser Asp Ser Pro
65                  70                  75                  80

Tyr Gln His Ser Asp Phe Arg Pro Val Cys Tyr Glu Glu Pro Leu His
                85                  90                  95

Trp Cys Ser Val Ala Tyr Tyr Glu Leu Asn Asn Arg Val Gly Glu Thr
                100                 105                 110

Phe Gln Ala Ser Ser Arg Ser Val Leu Ile Asp Gly Phe Thr Asp Pro
            115                 120                 125

Ser Asn Asn Arg Asn Arg Phe Cys Leu Gly Leu Leu Ser Asn Val Asn
            130                 135                 140

Arg Asn Ser Thr Ile Glu Asn Thr Arg Arg His Ile Gly Lys Gly Val
145                 150                 155                 160

His Leu Tyr Tyr Val Gly Gly Glu Val Tyr Ala Glu Cys Val Ser Asp
                165                 170                 175

Ser Ser Ile Phe Val Gln Ser Arg Asn Cys Asn Tyr Gln His Gly Phe
            180                 185                 190

His Pro Ala Thr Val Cys Lys Ile Pro Ser Gly Cys Ser Ile Lys Val
```

```
                195                 200                 205
Phe Asn Asn Gln Leu Phe Ala Gln Leu Leu Ala Gln Ser Val His His
210                 215                 220

Gly Phe Glu Val Val Tyr Glu Leu Thr Lys Met Cys Thr Ile Arg Met
225                 230                 235                 240

Ser Phe Val Lys Gly Trp Gly Ala Glu Tyr His Arg Gln Asp Val Thr
                245                 250                 255

Ser Thr Pro Cys Trp Ile Glu Ile His Leu His Gly Pro Leu Gln Trp
            260                 265                 270

Leu Asp Lys Val Leu Thr Gln Met Gly Ser Pro His Asn Pro Ile Ser
        275                 280                 285

Ser Val Ser
290

<210> SEQ ID NO 10
<211> LENGTH: 1356
<212> TYPE: DNA
<213> ORGANISM: Artificial sequence
<220> FEATURE:
<223> OTHER INFORMATION: FLAG tagged Rat SMAD8 polynucleotide

<400> SEQUENCE: 10
ggatccccac catggactac aaggatgacg atgacaagca ccccagcacc cccatcagct      60
ccctcttctc cttcaccagc cccgcagtga agaggctgct gggctggaag cagggagatg     120
aagaggagaa gtgggcagag aaggcagtgg actctttggt gaagaagtta agaaaaaga     180 aaggcgccat ggatgaactg agagggcgc tgagctgccc gggccagcct agcaagtgcg     240
ttaccattcc acgctccctg gatggacgcc tccaggtgtc ccaccggaag gggctgcccc     300
atgtcatcta ctgccgcgtg tggcgctggc cagatctgca atcccatcat gagctgaagc     360
ccttggaatg ctgcgagttc cgtttggct ctaagcagaa ggaggtctgc atcaacccat     420
accattaccg cagagtggag acccccagttc tgcctccagt gctggtacca agacacagcg     480
agtacaaccc tcagctcagc ctcctggcca gttccgaag tgcctcgctg cacagcgaac     540
cgctcatgcc gcacaacgcc acctaccctg actctttcca gcagtctctc ggtcccgcac     600
cgccctcctc gccaggacac gtgtttccgc agtctccatg ccccaccagc tacccgcagt     660 ccccccggaag tccttccgag tcagacagtc cttatcaaca ctcagacttc cggccagttt     720
gctacgagga gcccctgcac tggtgctctg ttgcctacta cgaactgaac aaccgggtcg     780
gagagacttt ccaggcatcc tcccggagtg tgctcataga tggcttcaca gacccctcca     840
ataacaggaa taggttctgt cttgggcttc tttcaaatgt aaacagaaat tcgacgatag     900
aaaacaccag aaggcacatt ggaaagggtg tgcatttgta ctacgttggg ggcgaggtgt     960
acgcggagtg cgtgagcgac agcagcatct tgtccagag ccggaactgc aactaccagc    1020
acggcttcca cccggccact gtctgcaaga tccccagtgg ctgcagcctc aaggtcttca    1080
acaaccagct cttcgcccag ctgctcgccc agtcagtgca ccacggcttt gaagttgtct    1140
atgaactgac gaagatgtgc acgattcgga tgagctttgt gaagggctgg ggagccgagt    1200
atcatcgcca ggatgtcaca agcacccct gctggattga gattcatctt catggaccac    1260
tgcagtggtt ggacaaggtg ctaactcaga tgggctcccc acacaaccct atttcttcag    1320
tgtcttaagt catgtgctca gctgcatttc cagtcg                                1356

<210> SEQ ID NO 11
<211> LENGTH: 917
```

```
<212> TYPE: DNA
<213> ORGANISM: Artificial sequence
<220> FEATURE:
<223> OTHER INFORMATION: FLAG tagged Rat SMAD8 L+MH2 polynucleotide

<400> SEQUENCE: 11
ggatccgcca ccatggacta caaggatgac gatgacaagg agtacaaccc tcagctcagc      60
ctcctggcca agttccgaag tgcctcgctg cacagcgaac cgctcatgcc gcacaacgcc     120
acctaccctg actctttcca gcagtctctc ggtcccgcac cgcctcctc gccaggacac      180
gtgtttccgc agtctccatg ccccaccagc tacccgcagt cccccggaag tccttccgag     240
tcagacagtc cttatcaaca ctcagacttc cggccagttt gctacgagga gcccctgcac     300
tggtgctctg ttgcctacta cgaactgaac aaccgggtcg agagactttt ccaggcatcc     360
tcccggagtg tgctcataga tggcttcaca gaccccctcca ataacaggaa taggttctgt    420
cttgggcttc tttcaaatgt aaacagaaat tcgacgatag aaaacaccag aaggcacatt     480
ggaaagggtg tgcatttgta ctacgttggg ggcgaggtgt acgcggagtg cgtgagcgac     540
agcagcatct ttgtccagag ccggaactgc aactaccagc acggcttcca cccggccact     600
gtctgcaaga tccccagtgg ctgcagcatc aaggtcttca caaccagct cttcgcccag      660
ctgctcgccc agtcagtgca ccacggcttt gaagttgtct atgaactgac gaagatgtgc     720
acgattcgga tgagctttgt gaagggctgg ggagccgagt atcatcgcca ggatgtcaca     780
agcaccccct gctggattga gattcatctt catggaccac tgcagtggtt ggacaaggtg     840
ctaactcaga tgggctcccc acacaaccct atttcttcag tgtcttaagt catgtgctca     900
gctgcatttc cagtcga                                                    917

<210> SEQ ID NO 12
<211> LENGTH: 434
<212> TYPE: PRT
<213> ORGANISM: Rattus norvegicus

<400> SEQUENCE: 12

Met His Pro Ser Thr Pro Ile Ser Ser Leu Phe Ser Phe Thr Ser Pro
1               5                   10                  15

Ala Val Lys Arg Leu Leu Gly Trp Lys Gln Gly Asp Glu Glu Glu Lys
            20                  25                  30

Trp Ala Glu Lys Ala Val Asp Ser Leu Val Lys Lys Leu Lys Lys Lys
        35                  40                  45

Lys Gly Ala Met Asp Glu Leu Glu Arg Ala Leu Ser Cys Pro Gly Gln
    50                  55                  60

Pro Ser Lys Cys Val Thr Ile Pro Arg Ser Leu Asp Gly Arg Leu Gln
65                  70                  75                  80

Val Ser His Arg Lys Gly Leu Pro His Val Ile Tyr Cys Arg Val Trp
                85                  90                  95

Arg Trp Pro Asp Leu Gln Ser His His Glu Leu Lys Pro Leu Glu Cys
            100                 105                 110

Cys Glu Phe Pro Phe Gly Ser Lys Gln Lys Glu Val Cys Ile Asn Pro
        115                 120                 125

Tyr His Tyr Arg Arg Val Glu Thr Pro Val Leu Pro Pro Val Leu Val
    130                 135                 140

Pro Arg His Ser Glu Tyr Asn Pro Gln Leu Ser Leu Leu Ala Lys Phe
145                 150                 155                 160

Arg Ser Ala Ser Leu His Ser Glu Pro Leu Met Pro His Asn Ala Thr
                165                 170                 175
```

```
Tyr Pro Asp Ser Phe Gln Gln Ser Leu Gly Pro Ala Pro Pro Ser Ser
                180                 185                 190

Pro Gly His Val Phe Pro Gln Ser Pro Cys Pro Thr Ser Tyr Pro Gln
            195                 200                 205

Ser Pro Gly Ser Pro Ser Glu Ser Asp Ser Pro Tyr Gln His Ser Asp
        210                 215                 220

Phe Arg Pro Val Cys Tyr Glu Glu Pro Leu His Trp Cys Ser Val Ala
225                 230                 235                 240

Tyr Tyr Glu Leu Asn Asn Arg Val Gly Glu Thr Phe Gln Ala Ser Ser
                245                 250                 255

Arg Ser Val Leu Ile Asp Gly Phe Thr Asp Pro Ser Asn Asn Arg Asn
            260                 265                 270

Arg Phe Cys Leu Gly Leu Leu Ser Asn Val Asn Arg Asn Ser Thr Ile
        275                 280                 285

Glu Asn Thr Arg Arg His Ile Gly Lys Gly Val His Leu Tyr Tyr Val
290                 295                 300

Gly Gly Glu Val Tyr Ala Glu Cys Val Ser Asp Ser Ser Ile Phe Val
305                 310                 315                 320

Gln Ser Arg Asn Cys Asn Tyr Gln His Gly Phe His Pro Ala Thr Val
                325                 330                 335

Cys Lys Ile Pro Ser Gly Cys Ser Leu Lys Val Phe Asn Asn Gln Leu
            340                 345                 350

Phe Ala Gln Leu Leu Ala Gln Leu Leu Ala Gln Ser Val His His Gly
        355                 360                 365

Phe Glu Val Val Tyr Glu Leu Thr Lys Met Cys Thr Ile Arg Met Ser
        370                 375                 380

Phe Val Lys Gly Trp Gly Ala Glu Tyr His Arg Gln Asp Val Thr Ser
385                 390                 395                 400

Thr Pro Cys Trp Ile Glu Ile His Leu His Gly Pro Leu Gln Trp Leu
                405                 410                 415

Asp Lys Val Leu Thr Gln Met Gly Ser Pro His Asn Pro Ile Ser Ser
            420                 425                 430

Val Ser

<210> SEQ ID NO 13
<211> LENGTH: 1611
<212> TYPE: DNA
<213> ORGANISM: Rattus norvegicus

<400> SEQUENCE: 13
tttgaattgg tccccactgc ttccagaagg aaaggcaagt tgttcctat gacatccccg      60 gacagatact tgccgctgac ctgcccaggg ccctgcaagc cttgaaaggt ctcatcttct    120
tttcccgagc aggagcctga ggtctgcctc ctatgcaccc cagcaccccc atcagctccc    180
tcttctcctt caccagcccc gcagtgaaga ggctgctggg ctggaagcag ggagatgaag    240
aggagaagtg ggcagagaag gcagtggact ctttggtgaa gaagttaaag aaaaagaaag    300
gcgccatgga tgaactggag agggcgctga gctgccgggg ccagcctagc aagtgcgtta    360
ccattccacg ctccctggat ggacgcctcc aggtgtccca ccggaagggg ctgccccatg    420
tcatctactg ccgcgtgtgg cgctggccag atctgcaatc ccatcatgag ctgaagccct    480
tggaatgctg cgagttcccg tttggctcta agcagaagga ggtctgcatc aacccatacc    540
attaccgcag agtggagacc ccagttctgc ctccagtgct ggtaccaaga cacagcgagt    600
```

| | |
|---|---|
| acaaccctca gctcagcctc ctggccaagt tccgaagtgc ctcgctgcac agcgaaccgc | 660 |
| tcatgccgca caacgccacc taccctgact cttttccagca gtctctcggt cccgcaccgc | 720 |
| cctcctcgcc aggacacgtg tttccgcagt ctccatgccc caccagctac ccgcagtccc | 780 |
| ccggaagtcc ttccgagtca gacagtcctt atcaacactc agacttccgg ccagtttgct | 840 |
| acgaggagcc cctgcactgg tgctctgttg cctactacga actgaacaac cgggtcggag | 900 |
| agactttcca ggcatcctcc cggagtgtgc tcatagatgg cttcacagac ccctccaata | 960 |
| acaggaatag gttctgtctt gggcttcttt caaatgtaaa cagaaattcg acgatagaaa | 1020 |
| acaccagaag gcacattgga aagggtgtgc atttgtacta cgttggggc gaggtgtacg | 1080 |
| cggagtgcgt gagcgacagc agcatctttg tccagagccg gaactgcaac taccagcacg | 1140 |
| gcttccaccc ggccactgtc tgcaagatcc ccagtggctg cagcctcaag gtcttcaaca | 1200 |
| accagctctt cgcccagctg ctcgcccagc tgctcgccca gtcagtgcac cacggctttg | 1260 |
| aagttgtcta tgaactgacg aagatgtgca cgattcggat gagctttgtg aagggctggg | 1320 |
| gagccgagta tcatcgccag gatgtcacaa gcacccctg ctggattgag attcatcttc | 1380 |
| atggaccact gcagtggttg gacaaggtgc taactcagat gggctcccca cacaacccta | 1440 |
| tttcttcagt gtcttaagtc atgtgctcag ctgcatttcc acagaataga cgaaggcagg | 1500 |
| ggcttctacc actgcaactc gcagctagta aaagaccctg gacgcagatg taaacacgta | 1560 |
| cgatgcacac gattcccatt tctatcccca ttggttctgt gctacctact t | 1611 |

<210> SEQ ID NO 14
<211> LENGTH: 2365
<212> TYPE: DNA
<213> ORGANISM: Homo sapiens

<400> SEQUENCE: 14

| | |
|---|---|
| cgcactaata cgggcgatga ggcttcgcgg ctccagtctg actgacgccg gctggggccg | 60 |
| ccgccgccgc cgccgccgcc gccgctgctg cagccgctgt ctcggtcccc gccgccgccg | 120 |
| ccgggccctg caggcgctgg gcgcgcgcag ccaggcaagt tggccaccct gttcaagggc | 180 |
| ttaggagaaa gtcaacacac ttcgcaactt gaattggtcc cagctgctcc cagaagaacg | 240 |
| ggcgggttgg tccctatgcc acccctggag agctactcgc cgcccacttt gccgtgaagg | 300 |
| gctgtgcggt tccgtgcgc gccggagcct gctgtggcct cttatgcact ccaccacccc | 360 |
| catcagctcc ctcttctcct tcaccagccc cgcagtgaag agactgctag gctggaagca | 420 |
| aggagatgaa gaggaaaagt gggcagagaa ggcagtggac tctctagtga agaagttaaa | 480 |
| gaagaagaag ggagccatgg acgagctgga gagggctctc agctgcccgg ggcagcccag | 540 |
| caaatgcgtc acgattcccc gctccctgga cgggcggctg caggtgtccc accgcaaggg | 600 |
| cctgccccat gtgatttact gtcgcgtgtg gcgctggccg gatctgcagt cccaccacga | 660 |
| gctgaagccg ctggagtgct gtgagttccc atttggctcc aagcagaaag aagtgtgcat | 720 |
| taacccttac cactaccgcc gggtggagac tccagtactg cctcctgtgc tcgtgccaag | 780 |
| acacagtgaa tataaccccc agctcagcct cctggccaag ttccgcagcg cctccctgca | 840 |
| cagtgagcca ctcatgccac acaacgccac ctatcctgac tctttccagc agcctccgtg | 900 |
| ctctgcactc cctccctcac ccagccacgc gttctcccag tccccgtgca cggccagcta | 960 |
| ccctcactcc ccaggaagtc cttctgagcc agagagtccc tatcaacact cagttgacac | 1020 |
| accaccctg cctatcatg ccacagaagc ctctgagacc cagagtggcc aacctgtaga | 1080 |
| tgccacagct gatagacatg tagtgctatc gataccaaat ggagactttc gaccagtttg | 1140 |

-continued

```
ttacgaggag ccccagcact ggtgctcggt cgcctactat gaactgaaca accgagttgg    1200
ggagacattc caggcttcct cccgaagtgt gctcatagat gggttcaccg acccttcaaa    1260
taacaggaac agattctgtc ttggacttct ttctaatgta aacagaaact caacgataga    1320
aaataccagg agacatatag aaagggtgt gcacttgtac tacgtcgggg gagaggtgta    1380
tgccgagtgc gtgagtgaca gcagcatctt tgtgcagagc cggaactgca actatcaaca    1440
cggcttccac ccagctaccg tctgcaagat ccccagcggc tgcagcctca aggtcttcaa    1500
caaccagctc ttcgctcagc tcctggccca gtcagttcac cacggctttg aagtcgtgta    1560
tgaactgacc aagatgtgta ctatccggat gagttttgtt aagggttggg gtgctgagta    1620
tcatcgccag gatgtcacca gcaccccctg ctggattgag attcatcttc atgggccact    1680
gcagtggctg gacaaagttc tgactcagat gggctctcca cataacccca tttcttcagt    1740
gtcttaacag tcatgtctta agctgcattt ccataggata gaggctattg cagggagtgg    1800
cttgtatcat ttcagatttg caactgaagt ttctaaaaac atgtgtaaat acatagaatg    1860
tatactgttc ttatttttt taatcaccgt ttgttttgtg ctttctagtt aacctgatgc    1920
cagtacagtg caattggaaa agcaggactt tggtgcctgt gctataagca gcagattttg    1980
tgggaggaaa cacttgagag gcgatattgt caacagtatt tgaagggtgt tagcagaata    2040
aaagacagct ttagtcagcc gtgtcattat aaagcatgtt gtgtggcctc acagaaacat    2100
tgaaactgtt tatacagcaa aagtcaggta ttagcagcac taaagcaaat atcactcaga    2160
tgaaacaaag cagtgaaacc cctacagttt aaatgatgtc acttttagtg ctgttggcaa    2220
gaaaaaaaaa acaacaaact tgtacaatga attaatgaga taggccatag aaactttatt    2280
tctaaggttg acatacctat agctgggctc ctgtgctcat attcagtggt acattttaaa    2340
caaactgtga tcgaaaaaaa aaaaa                                          2365
```

<210> SEQ ID NO 15
<211> LENGTH: 467
<212> TYPE: PRT
<213> ORGANISM: Homo sapiens

<400> SEQUENCE: 15

```
Met His Ser Thr Thr Pro Ile Ser Ser Leu Phe Ser Phe Thr Ser Pro
1               5                   10                  15

Ala Val Lys Arg Leu Leu Gly Trp Lys Gln Gly Asp Glu Glu Glu Lys
                20                  25                  30

Trp Ala Glu Lys Ala Val Asp Ser Leu Val Lys Leu Lys Lys Lys
            35                  40                  45

Lys Gly Ala Met Asp Glu Leu Glu Arg Ala Leu Ser Cys Pro Gly Gln
        50                  55                  60

Pro Ser Lys Cys Val Thr Ile Pro Arg Ser Leu Asp Gly Arg Leu Gln
65                  70                  75                  80

Val Ser His Arg Lys Gly Leu Pro His Val Ile Tyr Cys Arg Val Trp
                85                  90                  95

Arg Trp Pro Asp Leu Gln Ser His His Glu Leu Lys Pro Leu Glu Cys
                100                 105                 110

Cys Glu Phe Pro Phe Gly Ser Lys Gln Lys Glu Val Cys Ile Asn Pro
            115                 120                 125

Tyr His Tyr Arg Arg Val Glu Thr Pro Val Leu Pro Pro Val Leu Val
        130                 135                 140

Pro Arg His Ser Glu Tyr Asn Pro Gln Leu Ser Leu Leu Ala Lys Phe
```

```
                145                 150                 155                 160
Arg Ser Ala Ser Leu His Ser Glu Pro Leu Met Pro His Asn Ala Thr
                    165                 170                 175

Tyr Pro Asp Ser Phe Gln Gln Pro Pro Cys Ser Ala Leu Pro Pro Ser
                    180                 185                 190

Pro Ser His Ala Phe Ser Gln Ser Pro Cys Thr Ala Ser Tyr Pro His
                    195                 200                 205

Ser Pro Gly Ser Pro Ser Glu Pro Ser Pro Tyr Gln His Ser Val
                210                 215                 220

Asp Thr Pro Pro Leu Pro Tyr His Ala Thr Glu Ala Ser Glu Thr Gln
225                 230                 235                 240

Ser Gly Gln Pro Val Asp Ala Thr Ala Asp Arg His Val Val Leu Ser
                    245                 250                 255

Ile Pro Asn Gly Asp Phe Arg Pro Val Cys Tyr Glu Glu Pro Gln His
                    260                 265                 270

Trp Cys Ser Val Ala Tyr Tyr Glu Leu Asn Asn Arg Val Gly Glu Thr
                    275                 280                 285

Phe Gln Ala Ser Ser Arg Ser Val Leu Ile Asp Gly Phe Thr Asp Pro
                290                 295                 300

Ser Asn Asn Arg Asn Arg Phe Cys Leu Gly Leu Leu Ser Asn Val Asn
305                 310                 315                 320

Arg Asn Ser Thr Ile Glu Asn Thr Arg Arg His Ile Gly Lys Gly Val
                    325                 330                 335

His Leu Tyr Tyr Val Gly Gly Glu Val Tyr Ala Glu Cys Val Ser Asp
                    340                 345                 350

Ser Ser Ile Phe Val Gln Ser Arg Asn Cys Asn Tyr Gln His Gly Phe
                355                 360                 365

His Pro Ala Thr Val Cys Lys Ile Pro Ser Gly Cys Ser Leu Lys Val
                    370                 375                 380

Phe Asn Asn Gln Leu Phe Ala Gln Leu Leu Ala Gln Ser Val His His
385                 390                 395                 400

Gly Phe Glu Val Val Tyr Glu Leu Thr Lys Met Cys Thr Ile Arg Met
                    405                 410                 415

Ser Phe Val Lys Gly Trp Gly Ala Glu Tyr His Arg Gln Asp Val Thr
                    420                 425                 430

Ser Thr Pro Cys Trp Ile Glu Ile His Leu His Gly Pro Leu Gln Trp
                    435                 440                 445

Leu Asp Lys Val Leu Thr Gln Met Gly Ser Pro His Asn Pro Ile Ser
450                 455                 460

Ser Val Ser
465

<210> SEQ ID NO 16
<211> LENGTH: 465
<212> TYPE: PRT
<213> ORGANISM: Homo sapiens

<400> SEQUENCE: 16

Met Thr Ser Met Ala Ser Leu Phe Ser Phe Thr Ser Pro Ala Val Lys
1               5                   10                  15

Arg Leu Leu Gly Trp Lys Gln Gly Asp Glu Glu Lys Trp Ala Glu
                20                  25                  30

Lys Ala Val Asp Ala Leu Val Lys Lys Leu Lys Lys Lys Gly Ala
                35                  40                  45
```

```
Met Glu Glu Leu Glu Lys Ala Leu Ser Ser Pro Gly Gln Pro Ser Lys
    50                  55                  60
Cys Val Thr Ile Pro Arg Ser Leu Asp Gly Arg Leu Gln Val Ser His
 65                  70                  75                  80
Arg Lys Gly Leu Pro His Val Ile Tyr Cys Arg Val Trp Arg Trp Pro
                 85                  90                  95
Asp Leu Gln Ser His His Glu Leu Lys Pro Leu Asp Ile Cys Glu Phe
                100                 105                 110
Pro Phe Gly Ser Lys Gln Lys Glu Val Cys Ile Asn Pro Tyr His Tyr
            115                 120                 125
Lys Arg Val Glu Ser Pro Val Leu Pro Pro Val Leu Val Pro Arg His
130                 135                 140
Asn Glu Phe Asn Pro Gln His Ser Leu Leu Val Gln Phe Arg Asn Leu
145                 150                 155                 160
Ser His Asn Glu Pro His Met Pro Gln Asn Ala Thr Phe Pro Asp Ser
                165                 170                 175
Phe His Gln Pro Asn Asn Thr Pro Phe Pro Leu Ser Pro Asn Ser Pro
            180                 185                 190
Tyr Pro Pro Ser Pro Ala Ser Ser Thr Tyr Pro Asn Ser Pro Ala Ser
            195                 200                 205
Ser Gly Pro Gly Ser Pro Phe Gln Leu Pro Ala Asp Thr Pro Pro Pro
210                 215                 220
Ala Tyr Met Pro Pro Asp Asp Gln Met Gly Gln Asp Asn Ser Gln Pro
225                 230                 235                 240
Met Asp Thr Ser Asn Asn Met Ile Pro Gln Ile Met Pro Ser Ile Ser
                245                 250                 255
Ser Arg Asp Val Gln Pro Val Ala Tyr Glu Glu Pro Lys His Trp Cys
            260                 265                 270
Ser Ile Val Tyr Tyr Glu Leu Asn Asn Arg Val Gly Glu Ala Phe His
            275                 280                 285
Ala Ser Ser Thr Ser Val Leu Val Asp Gly Phe Thr Asp Pro Ser Asn
290                 295                 300
Asn Lys Ser Arg Phe Cys Leu Gly Leu Leu Ser Asn Val Asn Arg Asn
305                 310                 315                 320
Ser Thr Ile Glu Asn Thr Arg Arg His Ile Gly Lys Gly Val His Leu
                325                 330                 335
Tyr Tyr Val Gly Gly Glu Val Tyr Ala Glu Cys Leu Ser Asp Ser Ser
            340                 345                 350
Ile Phe Val Gln Ser Arg Asn Cys Asn Phe His His Gly Phe His Pro
            355                 360                 365
Thr Thr Val Cys Lys Ile Pro Ser Ser Cys Ser Leu Lys Ile Phe Asn
370                 375                 380
Asn Gln Glu Phe Ala Gln Leu Leu Ala Gln Ser Val Asn His Gly Phe
385                 390                 395                 400
Glu Ala Val Tyr Glu Leu Thr Lys Met Cys Thr Ile Arg Met Ser Phe
                405                 410                 415
Val Lys Gly Trp Gly Ala Glu Tyr His Arg Gln Asp Val Thr Ser Thr
            420                 425                 430
Pro Cys Trp Ile Glu Ile His Leu His Gly Pro Leu Gln Trp Leu Asp
            435                 440                 445
Lys Val Leu Thr Gln Met Gly Ser Pro Leu Asn Pro Ile Ser Ser Val
450                 455                 460

Ser
```

<210> SEQ ID NO 17
<211> LENGTH: 7096
<212> TYPE: DNA
<213> ORGANISM: Homo sapiens

<400> SEQUENCE: 17

```
ccgggtcctg ggcgagcggg cgccgtgcgc gtgtcccgcg gccgagctgc taataaagtt     60
gcagcgagga gaagcgcagc gacggcgtcg ggagagcgcg cctagccggc tcgcgaaaag    120
gaagctgttg aagttattga agtacctgtt gctatattct aagaaattaa aatgtccaga    180
aatctgcctc taaatgggat ctcactatgt tgctcagact ggacgtgatt gaactcctgg    240
gctcaagtga gtctcccgaa taactgggat tacaggactt gacccaatga agaagcata    300
tggcacttgt gaagataaat gttactcctc ccttttaat tggaacttct gcttaggacc    360
tgtgtatgac gtttcacctg tgatctgttc tttcggtagc cactgacttt gagttacagg    420
aaggtctccg aagatttgtg tcaaatgacg tcaatggcca gcttgttttc ttttactagt    480
ccagcagtaa agcgattgtt gggctggaaa caaggtgatg aggaggagaa atgggcagaa    540
aaggcagttg atgctttggt gaagaaacta aaaagaaaa agggtgccat ggaggaactg    600
gagaaagcct tgagcagtcc aggacagccg agtaaatgtg tcactattcc cagatcttta    660
gatggacgcc tgcaggtttc tcacagaaaa ggcttacccc atgttatata ttgtcgtgtt    720
tggcgctggc cggatttgca gagtcatcat gagctaaagc cgttggatat ttgtgaattt    780
cctttggat ctaagcaaaa agaagtttgt atcaacccat accactataa gagagtggag    840
agtccagtct tacctccagt attagtgcct cgtcataatg aattcaatcc acaacacagc    900
cttctggttc agtttaggaa cctgagccac aatgaaccac acatgccaca aaatgccacg    960
tttccagatt cttttccacca gcccaacaac actccttttc ccttatctcc aaacagccct   1020
tatcccccctt ctcctgctag cagcacatat cccaactccc cagcaagttc tggaccagga   1080
agtccatttc agctcccagc tgatacgcct cctcctgcct atatgccacc tgatgatcag   1140
atgggtcaag ataattccca gcctatggat acaagcaata atatgattcc tcagattatg   1200
cccagtatat ccagcaggga tgttcagcct gttgcctatg aagagcctaa acattggtgt   1260
tcaatagtct actatgaatt aaacaatcgt gttggagaag cttttcatgc atcttctact   1320
agtgtgttag tagatggatt cacagatcct tcaaataaca aaagtagatt ctgcttgggt   1380
ttgttgtcaa atgttaatcg taattcgaca attgaaaaca ctaggcgaca tattggaaaa   1440
ggtgttcatc tgtactatgt tggtggagag gtgtatgcgg aatgcctcag tgacagcagc   1500
atatttgtac agagtaggaa ctgcaacttt catcatggct tcatcccac cactgtctgt   1560
aagattccca gcagctgcag cctcaaaatt tttaacaatc aggagtttgc tcagcttctg   1620
gctcaatctg tcaaccatgg gtttgaggca gtatatgagc tcaccaaaat gtgtaccatt   1680
cggatgagtt ttgtcaaggg ttggggagca gaatatcacc ggcaggatgt aaccagcacc   1740
ccatgttgga ttgagattca tcttcatggg cctcttcagt ggctggataa agtccttact   1800
cagatgggct cccctctgaa ccccatatct tctgtttcat aatgcagaag tattcttttc   1860
aattatattg ttagtggact tgttttaatt ttagagaaac tttgagtaca gatactgtga   1920
gcttacattg aaaacagata ttacagctta ttttttttcta cataattgtg accaatacat   1980
ttgtattttg tgatgaatct acatttgttt gtattcatgt tcatgtgatt aactcttaga   2040
agtgttgtaa aagatgcaga gtaagtatta tgccccagtt cagaaatttg gcattgatct   2100
```

```
taaactggaa catgctttta ctttattgcc ctaacaattt tttattaaat ttatttgaaa    2160
atgcatcaca tgatgaaaaa ttatagtagc ttataagagg gcatatacag tgaagagtaa    2220
gttttccctc ctactctcga tcttccagaa gctgtacttt taccagtttc tttgtcccac    2280
caacttaaaa aaaaaagta caattcattg ttttgcaaaa gtgtatggta ggggcttaaa     2340
agaaactata aagttttatt tgaatgaaca ctatgcactg ctgtaactgg tagtgttcag    2400
taaaagcaaa atgatagttt tctagatgac ataaaattta catttaatac agataagtgt    2460
tcttcagtgt aatgtgactt catgctatat atcttttgta agacatttcc ttttttaaaa   2520
aaattttgc aaataactga tctcaagtat atgtcattta ctcaaaatct gtcataagca    2580
ttacttata gctagtgaca gtgcatgcac agccttgttc aactatgttt gctgcttttg    2640
gacaatgttg caagaactct atttttgaca tgcattaatc ttttattttg cacttttatg   2700
ggtgacagtt tttagcataa cctttgataa aatacactca agtgacttgg acttagatgc   2760
ttatccttac gtccttggta ccttttttgt attaacaaac actgcaattt atagattaca   2820
tttgtaggaa gttatgcttt tttctggttt ttgttttact ttcaacctag gttataagac   2880
tgttattcta tagctccaac ttaaggtgcc ttttaattc cctacagttt tatgggtgtt    2940
atcagtgctg gagaatcatg tagttaatcc cattgctctt acaagtgtca gcttacttgt   3000
atcagcctcc ctacgcaagg acctatgcac tggagccgta ggaggctctt cagttgggcc   3060
ccaaggataa ggctactgat ttgatactaa atgaatcagc agtggatgta gggatagctg   3120
attttaaaac actcggctgg gcacagtggc tcacacctgt aatcccagca ctttgggagg   3180
ctgaggcagg cagatcatga tgtcaggagt ttgagaccag cctggccaat atggtgaaac   3240
cctgtctcta caaaaaatac aaaaattagc tgggcatggt ggtgcgtgcc tgaagtccca   3300
gctactcggg aagctgaggc agaagaatca cttgaacctg ggaggcggag gttgtggtga   3360
gccgagatcg caccactgca ctccagcctg ggcgacagag cgagactctg cctcaaaaaa   3420
caaaacaaaa caaaacactc acccatcaac gaatatagac tcttctctca tttatcgatg   3480
atcctctttt tccattttt aagtactat gtggaagcta gtctcccaaa acacaatctt    3540
tagagagaaa agacatgaac gaactccaaa atatccattt aatcaatcat gtttttggct   3600
ttggataaag aactttgaac cagttttttt ctcaggagct gtcaaatgga cacttaatta   3660
tgacatgaga atgaagaaat tattttggaa aaaaaaatg acctaattta cctatcagtg    3720
aaagctttat tttctggtgc cttttgaaag tatatggagt catatcattc ttctgtttaa   3780
aatgttagtt tggtttgact ttccactttg tccttctgc tcttgtgaag aaaaaaaaaa     3840
gcattttcga ggaaagaatt atgcaatttc ttttgttttc tgtgtcatta tttattgctt   3900
tttcaatgtg cagccagtgg atggttttag ttctttcaga tgaactgcca tttgtgtttc   3960
agctcacagt tctttgctgg gtaaaagaaa tactttctga cagtcacctg agccttaaat   4020
gtaagtatta catgacatgc attctgtttc ttccagagtt ctgtctgcca cacgaaagag   4080
aatatttgct tacttgatag aactttggca ttttcatcat tcttttactt aaccaggctt   4140
atggcatgat ctctggaaca aatttgtagg aaaaaattac tccaattgaa tgactgatgt   4200
atgtaatcaa cttcattggg ctgcagtaaa ctagtggaaa ttagagagtt gttttattgg   4260
tgttttctac tgtgagttaa ttaaaaattg ttttatttg gggtcattat gtcacagtct    4320
tgagttaaca agatcttacg tgattggcct tttctttgtt ttctcttagg agttgtgtct   4380
catgaatgac agtactaaag ctattaacaa ctaagagttt gacagagaac tataagcctg   4440
```

```
ttgtatctcc taaaagttgt caactcccca cccttggact ttaaatgaaa attttattca   4500
gtccagctat tcttacagtc cctaaggatt ttcatatatc tatgtatagg agataaaatt   4560
tgctagtaag attttaaaa  actggctagt gaaaggaaag tacctctgaa agaaaccatt   4620
ttagcaaatt atggttatat gttttaattt aatctacaga atgttttata gtaaaattct   4680
agcaccacta gaataatcac atagcatgta caatatattt atgctggctg aaaagacaga   4740
atctgggaat aataaaattg caaccagttt ggtaatgcaa acagcagaat agaatgaaat   4800
ctcagtaatg aattaaagca acaaaaagat attgattggc aaaaagcaag atataagaga   4860
ttcatttgct taacatttct acataatatt tatggtctgg tcagtattgg tctggtcagt   4920
attgcctggc tgacgtgaaa tgtaaactag taggcgtgtt attgatctgc taaaactaac   4980
cctcttttta agaggagatt taaggaagac gtcaatcaaa atgtcaaata tgtgtgtcag   5040
aatataaata attttttcaca ttgtattgtt gctatataaa aaaaataata gaattggttg   5100
ggtttctgag gtgaaatcca gagtaagagt actagacagt tcaacaagcc acatctaatg   5160
gcacagatag aggatgtagc tattttatac ctttcataac atttgagagt aagatatcct   5220
tcaggatgtg aagtgattat taagtactca tacctgaaat ctgttgtcaa gattagaact   5280
ggggttcatg ttaaaaacct tccatattac ctgagggtac ctgtggggaa cagttccttc   5340
ccctgtgtgg tagtattttg ttggaagaga atgtttatac aaaaaatgaa attcttccaa   5400
cagcagagaa actctaaaaa gtttgatagt acctatcaaa gtgctgtact tctgtgatag   5460
agaacatctg atgtaccaat ttagatctat ttctttatac ttttttctaat caattgctta   5520
atagtacttt ggatgattat caccttttgcc acttaaaata tataaatatc ctttttactt   5580
catgaggaag gaagaatttt ttgataatta ctgagttcag cctttttgtga tgacttatat   5640
tttggactta cattttaact ttaaagaatg tcagatccct tctttgtctt actagttaaa   5700
tcctcaccta atctcttggg tatgaatata aatgtgtgtc atcgttatat tgttcagcta   5760
gatgagcaag tatcttaggg tagtaggtag cctggtggtt ttagaagtgt ttggtgattt   5820
ttatggagag agttttccta agtggtggtt tataggtggt atcagatatt attagggcag   5880
cttttttgggg agtaatctca ggtctcccag agcagcagca ttttttctcat tgatataagt   5940
aagattctta ggagcttttc ttatcacaca agatgcctga atcgaatgtg agaattgaag   6000
gcatttcttc tgcataaaca aagaattcta cctgctggac agaaacctgg aaagttcttt   6060
ggaattcgct gaattacagt ttagtatgtc ctgattacag agtgacaata tttatcaagc   6120
ctttgttata ttggattatc ttctctctta aaatacaact gtattataat tgaaatgaca   6180
gcccaaaatt ggatggttta ccaaaaccaa tgaaagggat ttcacacatc aattttttatt   6240
tctgttttga agagcacatg ctatataata attgctagta gcaactgcag taaaacaggt   6300
gataagttat tttctctgaa aagatccagt cctagagcag gattcttcga tcattcatgg   6360
cagagtgaaa aaggtttgta tggttcttgt ccaaataact cagttcttaa aattcttaaa   6420
atgatcgtaa accattatcc tttaaaggtt tatttgaaga tgctgttaaa gtacagaatt   6480
ttgtgtacag gtagattttt ccgtccctca ttaatagtgc cttcttaatt aatacagact   6540
ggtgttagct ataacaaaac tccagtaagg ccaagaatcc caagttctt  tgtgaaaaaa   6600
aaaaaaaaat cttttagggt cagattttcc cttctaatat cattgaagat gatgttgcat   6660
tgatttattc ataaagtatt ttaactatag gaactctaga agataatggt taggcaagtg   6720
atttttttt  taaatatggt tggcgtaagt tgtattttga aattcactta ttttaaaatc   6780
gaagaggatt gtaatcatgg aaatagaatg tttgtatcta cctgcccaca ttttcttaaa   6840
```

```
aagatatttc atatacagat aatgaagacc aagctagtgg ctgcactgta ggtctgctgc    6900
ttatttgtat ttgttgtgct tctgtttatg ttgtagaagc tgaaattcta gcaacatgct    6960
tcaattctgt tattttgata cttatgaaaa tgtattaggt tttactatat tgtgcttttg    7020
aaagccataa ctcttaagaa ctttgttttt gcatattgtt tgctaattct ttactttaat    7080
aaacctcaaa acctgc                                                    7096
```

<210> SEQ ID NO 18
<211> LENGTH: 465
<212> TYPE: PRT
<213> ORGANISM: Homo sapiens

<400> SEQUENCE: 18

```
Met Asn Val Thr Ser Leu Phe Ser Phe Thr Ser Pro Ala Val Lys Arg
1               5                   10                  15

Leu Leu Gly Trp Lys Gln Gly Asp Glu Glu Lys Trp Ala Glu Lys
            20                  25                  30

Ala Val Asp Ala Leu Val Lys Lys Leu Lys Lys Lys Gly Ala Met
        35                  40                  45

Glu Glu Leu Glu Lys Ala Leu Ser Cys Pro Gly Gln Pro Ser Asn Cys
50                  55                  60

Val Thr Ile Pro Arg Ser Leu Asp Gly Arg Leu Gln Val Ser His Arg
65                  70                  75                  80

Lys Gly Leu Pro His Val Ile Tyr Cys Arg Val Trp Arg Trp Pro Asp
                85                  90                  95

Leu Gln Ser His His Glu Leu Lys Pro Leu Glu Cys Cys Glu Phe Pro
            100                 105                 110

Phe Gly Ser Lys Gln Lys Glu Val Cys Ile Asn Pro Tyr His Tyr Lys
        115                 120                 125

Arg Val Glu Ser Pro Val Leu Pro Pro Val Leu Val Pro Arg His Ser
130                 135                 140

Glu Tyr Asn Pro Gln His Ser Leu Leu Ala Gln Phe Arg Asn Leu Gly
145                 150                 155                 160

Gln Asn Glu Pro His Met Pro Leu Asn Ala Thr Phe Pro Asp Ser Phe
                165                 170                 175

Gln Gln Pro Asn Ser His Pro Phe Pro His Ser Pro Asn Ser Ser Tyr
            180                 185                 190

Pro Asn Ser Pro Gly Ser Ser Ser Thr Tyr Pro His Ser Pro Thr
        195                 200                 205

Ser Ser Asp Pro Gly Ser Pro Phe Gln Met Pro Ala Asp Thr Pro Pro
210                 215                 220

Pro Ala Tyr Leu Pro Pro Glu Asp Pro Met Thr Gln Asp Gly Ser Gln
225                 230                 235                 240

Pro Met Asp Thr Asn Met Met Ala Pro Pro Leu Pro Ser Glu Ile Asn
                245                 250                 255

Arg Gly Asp Val Gln Ala Val Ala Tyr Glu Glu Pro Lys His Trp Cys
            260                 265                 270

Ser Ile Val Tyr Tyr Glu Leu Asn Asn Arg Val Gly Glu Ala Phe His
        275                 280                 285

Ala Ser Ser Thr Ser Val Leu Val Asp Gly Phe Thr Asp Pro Ser Asn
    290                 295                 300

Asn Lys Asn Arg Phe Cys Leu Gly Leu Leu Ser Asn Val Asn Arg Asn
305                 310                 315                 320
```

```
Ser Thr Ile Glu Asn Thr Arg Arg His Ile Gly Lys Gly Val His Leu
            325                 330                 335

Tyr Tyr Val Gly Gly Glu Val Tyr Ala Glu Cys Leu Ser Asp Ser Ser
        340                 345                 350

Ile Phe Val Gln Ser Arg Asn Cys Asn Tyr His His Gly Phe His Pro
        355                 360                 365

Thr Thr Val Cys Lys Ile Pro Ser Gly Cys Ser Leu Lys Ile Phe Asn
    370                 375                 380

Asn Gln Glu Phe Ala Gln Leu Leu Ala Gln Ser Val Asn His Gly Phe
385                 390                 395                 400

Glu Thr Val Tyr Glu Leu Thr Lys Met Cys Thr Ile Arg Met Ser Phe
            405                 410                 415

Val Lys Gly Trp Gly Ala Glu Tyr His Arg Gln Asp Val Thr Ser Thr
        420                 425                 430

Pro Cys Trp Ile Glu Ile His Leu His Gly Pro Leu Gln Trp Leu Asp
    435                 440                 445

Lys Val Leu Thr Gln Met Gly Ser Pro His Asn Pro Ile Ser Ser Val
    450                 455                 460

Ser
465

<210> SEQ ID NO 19
<211> LENGTH: 2880
<212> TYPE: DNA
<213> ORGANISM: Homo sapiens

<400> SEQUENCE: 19
cactgcatgt gtattcgtga gttcgcggtt gaacaactgt tcctttactc tgctccctgt      60
ctttgtgctg actgggttac ttttttaaac actaggaatg gtaatttcta ctcttctgga     120
cttcaaacta agaagttaaa gagacttctc tgtaaataaa caaatctctt ctgctgtcct     180
tttgcatttg agacagcttt tatttcacca tatccaagga gtataactag tgctgtcatt     240
atgaatgtga caagtttatt ttcctttaca agtccagctg tgaagagact tcttgggtgg     300
aaacagggcg atgaagaaga aaaatgggca gagaaagctt tgatgctttt ggtgaaaaaa     360
ctgaagaaaa agaaaggtgc catggaggaa ctggaaaagg ccttgagctg cccagggcaa     420
ccgagtaact gtgtcaccat ccccgctct ctggatggca ggctgcaagt ctcccaccgg     480
aagggactgc tcatgtcat ttactgccgt gtgtggcgct ggcccgatct tcagagccac     540
catgaactaa aaccactgga atgctgtgag tttccttttg gttccaagca gaaggaggtc     600
tgcatcaatc cctaccacta agagagta gaaagccctg tacttcctcc tgtgctggtt     660
ccaagacaca gcgaatataa tcctcagcac agcctcttag ctcagttccg taacttagga     720
caaaatgagc tcacatgcc actcaacgcc acttttccag attctttcca gcaacccaac     780
agccacccgt ttcctcactc tcccaatagc agttacccaa actctcctgg gagcagcagc     840
agcacctacc ctcactctcc caccagctca gacccaggaa gccctttcca gatgccagct     900
gatacgcccc cacctgctta cctgcctcct gaagacccca tgacccagga tggctctcag     960
ccgatggaca caaacatgat ggcgcctccc ctgccctcag aaatcaacag aggagatgtt    1020
caggcggttg cttatgagga accaaaacac tggtgctcta ttgtctacta tgagctcaac    1080
aatcgtgtgg gtgaagcgtt ccatgcctcc tccacaagtg tgttggtgga tggtttcact    1140
gatccttcca caataagaa ccgtttctgc cttgggctgc tctccaatgt taaccggaat    1200
tccactattg aaaacaccag gcggcatatt ggaaaaggag ttcatcttta ttatgttgga    1260
```

```
ggggaggtgt atgccgaatg ccttagtgac agtagcatct ttgtgcaaag tcggaactgc    1320
aactaccatc atggatttca tcctactact gtttgcaaga tccctagtgg gtgtagtctg    1380
aaaatttta acaaccaaga atttgctcag ttattggcac agtctgtgaa ccatggattt    1440
gagacagtct atgagcttac aaaaatgtgt actatacgta tgagctttgt gaagggctgg    1500
ggagcagaat accaccgcca ggatgttact agcaccccct gctggattga gatacatctg    1560
cacggccccc tccagtggct ggataaagtt cttactcaaa tgggttcacc tcataatcct    1620
atttcatctg tatcttaaat ggccccaggc atctgcctct ggaaaactat tgagccttgc    1680
atgtacttga aggatggatg agtcagacac gattgagaac tgacaaagga gccttgataa    1740
tacttgacct ctgtgaccaa ctgttggatt cagaaattta acaaaaaaa aaaaaaaaca    1800
cacacacctt ggtaacatac tgttgatatc aagaacctgt ttagtttaca ttgtaacatt    1860
ctattgtaaa atcaactaaa attcagactt ttagcaggac tttgtgtaca gttaaaggag    1920
agatggccaa gccagggaca aattgtctat tagaaaacgg tcctaagaga ttctttggtg    1980
tttggcactt taaggtcatc gttgggcaga agtttagcat taatagttgt tctgaaacgt    2040
gttttatcag gttagagcc catgttgagt cttcttttca tgggttttca taatatttta    2100
aaactatttg tttagcgatg gttttgttcg tttaagtaaa ggttaatctt gatgatatac    2160
ataataatct ttctaaaatt gtatgctgac catacttgct gtcagaataa tgctaggcat    2220
atgcttttg ctaaatatgt atgtacagag tatttggaag ttaagaattg attagactag    2280
tgaatttagg agtatttgag gtgggtgggg ggaagaggga aatgacaact gcaaatgtag    2340
actatactgt aaaaattcag tttgttgctt taaagaaaca aactgatacc tgaattttgc    2400
tgtgttccca tttttagag attttatca tttttttctc tctcggcatt ctttttctc    2460
atactcttca aaaagcagtt ctgcagctgg ttaattcatg taactgtgag agcaaatgaa    2520
taattcctgc tattctgaaa ttgcctacat gtttcaatac cagttatatg gagtgcttga    2580
atttaataag cagttttac ggagtttaca gtacagaaat aggctttaat tttcaagtga    2640
attttttgcc aaacttagta actctgttaa atatttggag gatttaaaga acatcccagt    2700
ttgaattcat ttcaaacttt ttaaatttt ttgtactatg tttggtttta ttttccttct    2760
gttaatcttt tgtattcact tatgctctcg tacattgagt acttttattc caaaactagt    2820
gggttttctc tactgaaaat tttcaataaa cctgtcatta ttgcttactt tgattaaaaa    2880
```

<210> SEQ ID NO 20
<211> LENGTH: 372
<212> TYPE: PRT
<213> ORGANISM: Homo sapiens

<400> SEQUENCE: 20

Met His Phe Ser Thr Val Thr Arg Asp Met Glu Ala Phe Thr Ala Ser
1               5                   10                  15

Ser Leu Ser Ser Leu Gly Ala Ala Gly Gly Phe Pro Gly Ala Ala Ser
            20                  25                  30

Pro Gly Ala Asp Pro Tyr Gly Pro Arg Glu Pro Pro Pro Pro Pro Pro
        35                  40                  45

Arg Tyr Asp Pro Cys Ala Ala Ala Pro Gly Ala Pro Gly Pro Pro
    50                  55                  60

Pro Pro Pro His Ala Tyr Pro Phe Ala Pro Ala Gly Ala Ala Thr
65                  70                  75                  80

Ser Ala Ala Ala Glu Pro Glu Gly Pro Gly Ala Ser Cys Ala Ala Ala

```
                    85                  90                  95
Ala Lys Ala Pro Val Lys Lys Asn Ala Lys Val Ala Gly Val Ser Val
                100                 105                 110

Gln Leu Glu Met Lys Ala Leu Trp Asp Glu Phe Asn Gln Leu Gly Thr
            115                 120                 125

Glu Met Ile Val Thr Lys Ala Gly Arg Arg Met Phe Pro Thr Phe Gln
130                 135                 140

Val Lys Leu Phe Gly Met Asp Pro Met Ala Asp Tyr Met Leu Leu Met
145                 150                 155                 160

Asp Phe Val Pro Val Asp Asp Lys Arg Tyr Arg Tyr Ala Phe His Ser
                165                 170                 175

Ser Ser Trp Leu Val Ala Gly Lys Ala Asp Pro Ala Thr Pro Gly Arg
            180                 185                 190

Val His Tyr His Pro Asp Ser Pro Ala Lys Gly Ala Gln Trp Met Lys
        195                 200                 205

Gln Ile Val Ser Phe Asp Lys Leu Lys Leu Thr Asn Asn Leu Leu Asp
    210                 215                 220

Asp Asn Gly His Ile Ile Leu Asn Ser Met His Arg Tyr Gln Pro Arg
225                 230                 235                 240

Phe His Val Val Tyr Val Asp Pro Arg Lys Asp Ser Glu Lys Tyr Ala
                245                 250                 255

Glu Glu Asn Phe Lys Thr Phe Val Phe Glu Glu Thr Arg Phe Thr Ala
            260                 265                 270

Val Thr Ala Tyr Gln Asn His Arg Ile Thr Gln Leu Lys Ile Ala Ser
        275                 280                 285

Asn Pro Phe Ala Lys Gly Phe Arg Asp Cys Asp Pro Glu Asp Trp Pro
    290                 295                 300

Arg Asn His Arg Pro Gly Ala Leu Pro Leu Met Ser Ala Phe Ala Arg
305                 310                 315                 320

Ser Arg Asn Pro Val Ala Ser Pro Thr Gln Pro Ser Gly Thr Glu Lys
                325                 330                 335

Gly Leu Val Thr Glu Gly Ser Gly Leu Gln Pro Gly Leu Leu Asp Val
            340                 345                 350

Leu Leu Lys Pro Pro Ser Lys Lys Ser Glu Ser Leu Arg Pro Pro His
        355                 360                 365

Cys Lys Asp Thr
    370

<210> SEQ ID NO 21
<211> LENGTH: 398
<212> TYPE: PRT
<213> ORGANISM: Homo sapiens

<400> SEQUENCE: 21

Met His Phe Ser Thr Val Thr Arg Asp Met Glu Ala Phe Thr Ala Ser
1               5                   10                  15

Ser Leu Ser Ser Leu Gly Ala Ala Gly Gly Phe Pro Gly Ala Ala Ser
            20                  25                  30

Pro Gly Ala Asp Pro Tyr Gly Pro Arg Glu Pro Pro Pro Pro Pro Pro
        35                  40                  45

Arg Tyr Asp Pro Cys Ala Ala Ala Pro Gly Ala Pro Gly Pro Pro
    50                  55                  60

Pro Pro Pro His Ala Tyr Pro Phe Ala Pro Ala Ala Gly Ala Ala Thr
65                  70                  75                  80
```

```
Ser Ala Ala Ala Glu Pro Glu Gly Pro Gly Ala Ser Cys Ala Ala Ala
                85                  90                  95

Ala Lys Ala Pro Val Lys Lys Asn Ala Lys Val Ala Gly Val Ser Val
            100                 105                 110

Gln Leu Glu Met Lys Ala Leu Trp Asp Glu Phe Asn Gln Leu Gly Thr
        115                 120                 125

Glu Met Ile Val Thr Lys Ala Gly Arg Arg Met Phe Pro Thr Phe Gln
130                 135                 140

Val Lys Leu Phe Gly Met Asp Pro Met Ala Asp Tyr Met Leu Leu Met
145                 150                 155                 160

Asp Phe Val Pro Val Asp Asp Lys Arg Tyr Arg Tyr Ala Phe His Ser
                165                 170                 175

Ser Ser Trp Leu Val Ala Gly Lys Ala Asp Pro Ala Thr Pro Gly Arg
            180                 185                 190

Val His Tyr His Pro Asp Ser Pro Ala Lys Gly Ala Gln Trp Met Lys
        195                 200                 205

Gln Ile Val Ser Phe Asp Lys Leu Lys Leu Thr Asn Asn Leu Leu Asp
    210                 215                 220

Asp Asn Gly His Ile Ile Leu Asn Ser Met His Arg Tyr Gln Pro Arg
225                 230                 235                 240

Phe His Val Val Tyr Val Asp Pro Arg Lys Asp Ser Glu Lys Tyr Ala
                245                 250                 255

Glu Glu Asn Phe Lys Thr Phe Val Phe Glu Glu Thr Arg Phe Thr Ala
            260                 265                 270

Val Thr Ala Tyr Gln Asn His Arg Ile Thr Gln Leu Lys Ile Ala Ser
        275                 280                 285

Asn Pro Phe Ala Lys Gly Phe Arg Asp Cys Asp Pro Glu Asp Trp Pro
    290                 295                 300

Arg Asn His Arg Pro Gly Ala Leu Pro Leu Met Ser Ala Phe Ala Arg
305                 310                 315                 320

Ser Arg Asn Pro Val Ala Ser Pro Thr Gln Pro Ser Gly Thr Glu Lys
                325                 330                 335

Gly Gly His Val Leu Lys Asp Lys Glu Val Lys Ala Glu Thr Ser Arg
            340                 345                 350

Asn Thr Pro Glu Arg Glu Val Glu Leu Leu Arg Asp Ala Gly Gly Cys
        355                 360                 365

Val Asn Leu Gly Leu Pro Cys Pro Ala Glu Cys Gln Pro Phe Asn Thr
    370                 375                 380

Gln Gly Leu Val Ala Gly Arg Thr Ala Gly Asp Arg Leu Cys
385                 390                 395

<210> SEQ ID NO 22
<211> LENGTH: 495
<212> TYPE: PRT
<213> ORGANISM: Homo sapiens

<400> SEQUENCE: 22

Met His Phe Ser Thr Val Thr Arg Asp Met Glu Ala Phe Thr Ala Ser
1               5                   10                  15

Ser Leu Ser Leu Gly Ala Ala Gly Gly Phe Pro Gly Ala Ala Ser
            20                  25                  30

Pro Gly Ala Asp Pro Tyr Gly Pro Arg Glu Pro Pro Pro Pro
        35                  40                  45

Arg Tyr Asp Pro Cys Ala Ala Ala Pro Gly Ala Pro Gly Pro Pro
    50                  55                  60
```

-continued

```
Pro Pro Pro His Ala Tyr Pro Phe Ala Pro Ala Ala Gly Ala Ala Thr
65                  70                  75                  80

Ser Ala Ala Ala Glu Pro Glu Gly Pro Gly Ala Ser Cys Ala Ala Ala
            85                  90                  95

Ala Lys Ala Pro Val Lys Lys Asn Ala Lys Val Ala Gly Val Ser Val
        100                 105                 110

Gln Leu Glu Met Lys Ala Leu Trp Asp Glu Phe Asn Gln Leu Gly Thr
    115                 120                 125

Glu Met Ile Val Thr Lys Ala Gly Arg Arg Met Phe Pro Thr Phe Gln
130                 135                 140

Val Lys Leu Phe Gly Met Asp Pro Met Ala Asp Tyr Met Leu Leu Met
145                 150                 155                 160

Asp Phe Val Pro Val Asp Asp Lys Arg Tyr Arg Tyr Ala Phe His Ser
                165                 170                 175

Ser Ser Trp Leu Val Ala Gly Lys Ala Asp Pro Ala Thr Pro Gly Arg
            180                 185                 190

Val His Tyr His Pro Asp Ser Pro Ala Lys Gly Ala Gln Trp Met Lys
        195                 200                 205

Gln Ile Val Ser Phe Asp Lys Leu Lys Leu Thr Asn Asn Leu Leu Asp
    210                 215                 220

Asp Asn Gly His Ile Ile Leu Asn Ser Met His Arg Tyr Gln Pro Arg
225                 230                 235                 240

Phe His Val Val Tyr Val Asp Pro Arg Lys Asp Ser Glu Lys Tyr Ala
                245                 250                 255

Glu Glu Asn Phe Lys Thr Phe Val Phe Glu Glu Thr Arg Phe Thr Ala
            260                 265                 270

Val Thr Ala Tyr Gln Asn His Arg Ile Thr Gln Leu Lys Ile Ala Ser
        275                 280                 285

Asn Pro Phe Ala Lys Gly Phe Arg Asp Cys Asp Pro Glu Asp Trp Pro
    290                 295                 300

Arg Asn His Arg Pro Gly Ala Leu Pro Leu Met Ser Ala Phe Ala Arg
305                 310                 315                 320

Ser Arg Asn Pro Val Ala Ser Pro Thr Gln Pro Ser Gly Thr Glu Lys
                325                 330                 335

Asp Ala Ala Glu Ala Arg Arg Glu Phe Gln Arg Asp Ala Gly Gly Pro
            340                 345                 350

Ala Val Leu Gly Asp Pro Ala His Pro Pro Gln Leu Leu Ala Arg Val
        355                 360                 365

Leu Ser Pro Ser Leu Pro Gly Ala Gly Ala Gly Gly Leu Val Pro
    370                 375                 380

Leu Pro Gly Ala Pro Gly Gly Arg Pro Ser Pro Asn Pro Glu Leu
385                 390                 395                 400

Arg Leu Glu Ala Pro Gly Ala Ser Glu Pro Leu His His Pro Tyr
                405                 410                 415

Lys Tyr Pro Ala Ala Tyr Asp His Tyr Leu Gly Ala Lys Ser Arg
            420                 425                 430

Pro Ala Pro Tyr Pro Leu Pro Gly Leu Arg Gly His Gly Tyr His Pro
        435                 440                 445

His Ala His Pro His His His His Pro Val Ser Pro Ala Ala Ala
    450                 455                 460

Ala Ala Ala Ala Ala Ala Ala Ala Ala Ala Ala Asn Met Tyr Ser
465                 470                 475                 480
```

Ser Ala Gly Ala Ala Pro Pro Gly Ser Tyr Asp Tyr Cys Pro Arg
            485                 490                 495

<210> SEQ ID NO 23
<211> LENGTH: 1538
<212> TYPE: DNA
<213> ORGANISM: Homo sapiens

<400> SEQUENCE: 23

| | | | | | |
|---|---|---|---|---|---|
| ccggcagggg | gagcgaggag | gaagggaacc | gcggccgggc | cagcggaggc | ggcggagcgc | 60 |
| accgcccacc | agggctcagg | gtcctccgac | cgggtgaagc | ttcgctggct | gccaggatcc | 120 |
| ccggcaggga | tgcacttcag | caccgtcacc | agggacatgg | aagccttcac | ggccagcagc | 180 |
| ctgagcagcc | tggggccgc | gggggggcttc | ccggcgccg | cgtcgcccgg | cgccgacccg | 240 |
| tacgcccgc | cgagccccc | gccgccgccg | ccgcgctacg | acccgtgcgc | cgccgccgcc | 300 |
| cccggcgccc | cgggcccgcc | ccgccgccg | cacgcctacc | cgtttgcgcc | ggccgccggg | 360 |
| gccgccacca | cgccgccgc | cgagcccgag | ggccccgggg | ccagctgcgc | ggccgcagcc | 420 |
| aaggcgccgg | tgaagaagaa | cgcgaaggtg | gccggtgtga | gcgtgcagct | agagatgaag | 480 |
| gcgctgtggg | acgagttcaa | ccagctgggc | accgagatga | tcgtcaccaa | ggccggcagg | 540 |
| cggatgtttc | ccaccttcca | agtgaagctc | ttcggcatgg | atcccatggc | cgactatatg | 600 |
| ctgctcatgg | acttcgtgcc | ggtggacgat | aagcgctacc | ggtacgcctt | ccacagctcc | 660 |
| tcctggctgg | tggcggggaa | ggccgaccct | gccacgccag | gccgcgtgca | ctaccacccg | 720 |
| gactcgcctg | ccaagggcgc | gcagtggatg | aagcaaatcg | tgtccttcga | caagctcaag | 780 |
| ctgaccaaca | acctactgga | cgacaacggc | cacattattc | tgaattccat | gcacagatac | 840 |
| cagccccgct | tccacgtggt | ctatgtggac | ccacgcaaag | atagcgagaa | atatgccgag | 900 |
| gagaacttca | aaccctttgt | gttcgaggag | acacgattca | ccgcggtcac | tgcctaccag | 960 |
| aaccatcgga | tcacgcagct | caagattgcc | agcaatccct | tcgcgaaagg | cttccgggac | 1020 |
| tgtgaccctg | aggactggcc | ccggaaccac | cggcccggcg | cactgccgct | catgagcgcc | 1080 |
| ttcgcgcgct | cgcggaaccc | cgtggcttcc | ccgacgcagc | ccagcggcac | ggagaaaggg | 1140 |
| ctggtcacag | aaggctctgg | gctccaacct | ggcttgctgg | acgtgctctt | gaagccccca | 1200 |
| agtaagaagt | ctgagtccct | gagaccacca | cactgcaagg | cacttgaag | gtactcaggt | 1260 |
| ttcagagccc | aagtcaggag | gtcaagtgtg | catgcaagag | gtggcagggg | acagatgtgc | 1320 |
| tgctgttccc | aggccacctg | cacagctgga | tggtggaagc | agttcactta | aaggccatga | 1380 |
| gttactcggg | aggctgaggc | aggaggatca | cttgagccta | ttagttggag | gctgcagtaa | 1440 |
| gctatgatca | tgccactgca | ctccagcctg | ggtgacagag | tgagaccccc | actgtccctg | 1500 |
| gtctcttaaa | agaaaaaaca | aacaaacaaa | ccaaaaaa | | | 1538 |

<210> SEQ ID NO 24
<211> LENGTH: 1482
<212> TYPE: DNA
<213> ORGANISM: Homo sapiens

<400> SEQUENCE: 24

| | | | | | |
|---|---|---|---|---|---|
| ccggcagggg | gagcgaggag | gaagggaacc | gcggccgggc | cagcggaggc | ggcggagcgc | 60 |
| accgcccacc | agggctcagg | gtcctccgac | cgggtgaagc | ttcgctggct | gccaggatcc | 120 |
| ccggcaggga | tgcacttcag | caccgtcacc | agggacatgg | aagccttcac | ggccagcagc | 180 |
| ctgagcagcc | tggggccgc | gggggggcttc | ccggcgccg | cgtcgcccgg | cgccgacccg | 240 |

-continued

```
tacggcccgc gcgagccccc gccgccgccg ccgcgctacg acccgtgcgc cgccgccgcc    300
cccggcgccc cgggcccgcc gccgccgccg cacgcctacc cgtttgcgcc ggccgccggg    360
gccgccacca gcgccgccgc cgagcccgag ggccccgggg ccagctgcgc ggccgcagcc    420
aaggcgccgt tgaagaagaa cgcgaaggtg gccggtgtga gcgtgcagct agagatgaag    480
gcgctgtggg acgagttcaa ccagctgggc accgagatga tcgtcaccaa ggccggcagg    540
cggatgtttc ccaccttcca agtgaagctc ttcggcatgg atcccatggc cgactatatg    600
ctgctcatgg acttcgtgcc ggtggacgat aagcgctacc ggtacgcctt ccacagctcc    660
tcctggctgg tggcggggaa ggccgaccct gccacgccag gccgcgtgca ctaccacccg    720
gactcgcctg ccaagggcgc gcagtggatg aagcaaatcg tgtccttcga caagctcaag    780
ctgaccaaca acctactgga cgacaacggc cacattattc tgaattccat gcacagatac    840
cagccccgct tccacgtggt ctatgtggac ccacgcaaag atagcgagaa atatgccgag    900
gagaacttca aaccctttgt gttcgaggag acacgattca ccgcggtcac tgcctaccag    960
aaccatcgga tcacgcagct caagattgcc agcaatccct tcgcgaaagg cttccggac   1020
tgtgaccctg aggactggcc ccggaaccac cggcccggcg cactgccgct catgagcgcc   1080
ttcgcgcgct cgcggaaccc cgtggcttcc ccgacgcagc ccagcggcac ggagaaaggt   1140
ggacatgtcc tgaaggacaa ggaagtgaaa gctgagacgt ctaggaacac accagagaga   1200
gaagtggagc ttctgaggga tgcaggtggc tgtgtgaacc tggggctccc ctgccccgca   1260
gagtgccaac ccttcaatac ccagggcctg gtggctggga ggaccgcagg tgaccgtctt   1320
tgttgaatgc tgaggccggg ccatgggcac atggagttgt cgtgtttccc ttcactttgg   1380
ttcatgtttg aaatttccaa aattaaaaaa acagtgactt gttcagtaaa ttccaatatg   1440
aataaagtgc atgttttgta ataaaaaaaa aaaaaaaaa aa                       1482
```

<210> SEQ ID NO 25
<211> LENGTH: 2082
<212> TYPE: DNA
<213> ORGANISM: Homo sapiens

<400> SEQUENCE: 25

```
ccggcagggg gagcgaggag gaagggaacc gcggccgggc cagcggaggc ggcggagcgc     60
accgcccacc agggctcagg gtcctccgac cgggtgaagc ttcgctggct gccaggatcc    120
ccggcaggga tgcacttcag caccgtcacc agggacatgg aagccttcac ggccagcagc    180
ctgagcagcc tggggccgc gggggcttc ccgggcgccg cgtcgcccgg cgccgacccg    240
tacggcccgc gcgagccccc gccgccgccg ccgcgctacg acccgtgcgc cgccgccgcc    300
cccggcgccc cgggcccgcc gccgccgccg cacgcctacc cgtttgcgcc ggccgccggg    360
gccgccacca gcgccgccgc cgagcccgag ggccccgggg ccagctgcgc ggccgcagcc    420
aaggcgccgg tgaagaagaa cgcgaaggtg gccggtgtga gcgtgcagct agagatgaag    480
gcgctgtggg acgagttcaa ccagctgggc accgagatga tcgtcaccaa ggccggcagg    540
cggatgtttc ccaccttcca agtgaagctc ttcggcatgg atcccatggc cgactatatg    600
ctgctcatgg acttcgtgcc ggtggacgat aagcgctacc ggtacgcctt ccacagctcc    660
tcctggctgg tggcggggaa ggccgaccct gccacgccag gccgcgtgca ctaccacccg    720
gactcgcctg ccaagggcgc gcagtggatg aagcaaatcg tgtccttcga caagctcaag    780
ctgaccaaca acctactgga cgacaacggc cacattattc tgaattccat gcacagatac    840
cagccccgct tccacgtggt ctatgtggac ccacgcaaag atagcgagaa atatgccgag    900
```

```
gagaacttca aaacctttgt gttcgaggag acacgattca ccgcggtcac tgcctaccag    960
aaccatcgga tcacgcagct caagattgcc agcaatccct tcgcgaaagg cttccgggac  1020
tgtgaccctg aggactggcc ccggaaccac cggcccggcg cactgccgct catgagcgcc  1080
ttcgcgcgct cgcggaaccc cgtggcttcc ccgacgcagc ccagcggcac ggagaaagac  1140
gcggctgagg cccggcgaga attccagcgc gacgcgggcg ggccagcagt gctcggggac  1200
ccggcgcatc ctccgcagct gctggcccgg gtgctaagcc cctcgctgcc cggggccggc  1260
ggcgccggcg gcttagtccc gctgcccggc gcgcccggag gccggcccag tccccgaac   1320 cccgagctgc gcctggaggc gcccggccgca tcggagccgc tgcaccacca ccctacaaa   1380 tatccggccg ccgcctacga ccactatctc ggggccaaga gccggccggc gccctacccg  1440
ctgcccggcc tgcgtggcca cggctaccac ccgcacgcgc atccgcacca ccaccaccac  1500
cccgtgagtc cagccgccgc ggccgccgcc gccgctgccg cagctgccgc ggccgccaac  1560
atgtactcgt cggccggagc cgcgccgccc ggctcctacg actattgccc cagataacac  1620
gggccctgtc gcgctcccgc cccggtcctg cacagccccg aagttcgccg ggcccggcca  1680
ccctgcccca agggcaagca aggaatacgt tcccccagcc caggggcca ccgcggctct   1740 cccctcccc agcctcgaag ccatgggggc cccctcgcca ccccagccc cttgggctat    1800 cgaagtatcc ggttcccag tccctggagc accgcgggt ccttccccgg ccccgagggc    1860
caagggggtc cccgcccgcc agtgccaaag cgcccggtcg gaggcggaag gaagtgatat  1920
ttattgttct ccccgagacc gcgtcgcccg cggcccggcc ggcagttgca gtgtagacag  1980
cccgagagcc ccgcctgcag gcggtgtaga tacatgtaga tactgtagat actgtagata  2040 ccgcccggc gccgacttga taaacggttt cgcctctttt gg                      2082
```

<210> SEQ ID NO 26
<211> LENGTH: 396
<212> TYPE: PRT
<213> ORGANISM: Homo sapiens

<400> SEQUENCE: 26

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
            165                 170                 175

Ile Lys Pro Ala Thr Ala Asn Ser Lys Phe Pro Val Thr Arg Leu Leu
        180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
        210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

```
<210> SEQ ID NO 27
<211> LENGTH: 1173
<212> TYPE: DNA
<213> ORGANISM: Bombyx mori

<400> SEQUENCE: 27
tgtatagtat ataccgattg gtcacataac agaccactaa aatgaagcct atatttttgg      60
tattactcgt cgctacaagc gcctacgctg caccatcggt gaccatcaat caatacagtg     120
ataatgaaat tccacgcgac attgatgatg gaaaagctag ttccgtaatc tcacgtcgat     180
gggactacgt cgatgacact gacaaaagca tcgccatcct caacgttcaa gagatcttga     240
aggacatggc cagccagggc gattatgcaa gtcaagcatc agcggtggcc caaaccgccg     300
gaattatcgc ccatctatct gccggtatcc ccggtgatgc ctgtgcagcc gctaacgtca     360
ttaactctta cacagacggc gtcaggtccg gaaacttcgc cggcttcaga caatctctcg     420
gtcccttctt cggacacgtg ggacaaaact tgaatcttat caatcaactc gtcatcaacc     480
ctggtcaact ccgatactct gtcggaccag ccctgggttg tgccggaggt ggaagaatct     540
atgacttcga agccgcttgg gatgcaatct tagccagcag tgactctagt ttcttaaatg     600
aagagtactg catcgtcaag agattgtaca actctcgcaa cagccaaagc aacaacatcg     660
ctgcctacat aaccgctcac ttacttcctc cggttgctca agtgttccac caatcagctg     720
gatcaatcac agacctcctg agaggcgttg gcaacggtaa tgacgcgacc ggcttagttg     780
```

-continued

```
ctaatgctca aagatatatt gcacaagcag ccagccaggt tcacgtctaa ataagaactg    840
taaataatgt atatatataa ttatataaaa gatatatata accatataca aacatatata    900
tcattataag acaatctacc tatataaaaa cagactaaaa ttaataatta tgtatacttt    960
aattgtgttt aggacatttt atgcaaattg tgtttgcgtt aggattttt ttggaagttt    1020 tttagattat ttatgaatat ataaataaat atacgttaat ataatatata ttatataaat   1080
caacgacacg gcttttcatt ttggtgatga tcaatcttat tgttcttcta attgattttt   1140
ttgtacaata aagatgtatc cagttttcca gat                                 1173
```

```
<210> SEQ ID NO 28
<211> LENGTH: 262
<212> TYPE: PRT
<213> ORGANISM: Bombyx mori

<400> SEQUENCE: 28
```

| | | | | | | | | | | | | | | |
|---|---|---|---|---|---|---|---|---|---|---|---|---|---|---|
| Met | Lys | Pro | Ile | Phe | Leu | Val | Leu | Val | Ala | Thr | Ser | Ala | Tyr | Ala |
| 1 | | | | 5 | | | | | 10 | | | | | 15 |
| Ala | Pro | Ser | Val | Thr | Ile | Asn | Gln | Tyr | Ser | Asp | Asn | Glu | Ile | Pro | Arg |
| | | | 20 | | | | | 25 | | | | | 30 | |
| Asp | Ile | Asp | Asp | Gly | Lys | Ala | Ser | Ser | Val | Ile | Ser | Arg | Arg | Trp | Asp |
| | | 35 | | | | | 40 | | | | | 45 | | |
| Tyr | Val | Asp | Asp | Thr | Asp | Lys | Ser | Ile | Ala | Ile | Leu | Asn | Val | Gln | Glu |
| 50 | | | | | 55 | | | | | 60 | | | | |
| Ile | Leu | Lys | Asp | Met | Ala | Ser | Gln | Gly | Asp | Tyr | Ala | Ser | Gln | Ala | Ser |
| 65 | | | | 70 | | | | | 75 | | | | | 80 |
| Ala | Val | Ala | Gln | Thr | Ala | Gly | Ile | Ile | Ala | His | Leu | Ser | Ala | Gly | Ile |
| | | | | 85 | | | | | 90 | | | | | 95 |
| Pro | Gly | Asp | Ala | Cys | Ala | Ala | Ala | Asn | Val | Ile | Asn | Ser | Tyr | Thr | Asp |
| | | | 100 | | | | | 105 | | | | | 110 | |
| Gly | Val | Arg | Ser | Gly | Asn | Phe | Ala | Gly | Phe | Arg | Gln | Ser | Leu | Gly | Pro |
| | | 115 | | | | | 120 | | | | | 125 | | |
| Phe | Phe | Gly | His | Val | Gly | Gln | Asn | Leu | Asn | Leu | Ile | Asn | Gln | Leu | Val |
| 130 | | | | | 135 | | | | | 140 | | | | |
| Ile | Asn | Pro | Gly | Gln | Leu | Arg | Tyr | Ser | Val | Gly | Pro | Ala | Leu | Gly | Cys |
| 145 | | | | | 150 | | | | | 155 | | | | | 160 |
| Ala | Gly | Gly | Gly | Arg | Ile | Tyr | Asp | Phe | Glu | Ala | Ala | Trp | Asp | Ala | Ile |
| | | | | 165 | | | | | 170 | | | | | 175 |
| Leu | Ala | Ser | Ser | Asp | Ser | Ser | Phe | Leu | Asn | Glu | Glu | Tyr | Cys | Ile | Val |
| | | | 180 | | | | | 185 | | | | | 190 | |
| Lys | Arg | Leu | Tyr | Asn | Ser | Arg | Asn | Ser | Gln | Ser | Asn | Asn | Ile | Ala | Ala |
| | | 195 | | | | | 200 | | | | | 205 | | |
| Tyr | Ile | Thr | Ala | His | Leu | Leu | Pro | Pro | Val | Ala | Gln | Val | Phe | His | Gln |
| 210 | | | | | 215 | | | | | 220 | | | | |
| Ser | Ala | Gly | Ser | Ile | Thr | Asp | Leu | Leu | Arg | Gly | Val | Gly | Asn | Gly | Asn |
| 225 | | | | | 230 | | | | | 235 | | | | | 240 |
| Asp | Ala | Thr | Gly | Leu | Val | Ala | Asn | Ala | Gln | Arg | Tyr | Ile | Ala | Gln | Ala |
| | | | | 245 | | | | | 250 | | | | | 255 |
| Ala | Ser | Gln | Val | His | Val |
| | | | 260 | | |

```
<210> SEQ ID NO 29
<211> LENGTH: 15792
<212> TYPE: DNA
<213> ORGANISM: Bombyx mori
```

```
<400> SEQUENCE: 29
atgagagtca aaacctttgt gatcttgtgc tgcgctctgc agtatgtcgc ttatacaaat      60
gcaaacatca atgattttga tgaggactat tttgggagtg atgtcactgt ccaaagtagt     120
aatacaacag atgaaataat tagagatgca tctggggcag ttatcgaaga acaaattaca     180
actaaaaaaa tgcaacggaa aaataaaaac catggaatac ttggaaaaaa tgaaaaaatg     240
atcaagacgt tcgttataac cacggattcc gacggtaacg agtccattgt agaggaagat     300
gtgctcatga agacactttc cgatggtact gttgctcaaa gttatgttgc tgctgatgcg     360
ggagcatatt ctcagagcgg gccatacgta tcaaacagtg gatacagcac tcatcaagga     420
tatacgagcg atttcagcac tagtgctgca gtcggtgcag gagctggtgc aggtgctgcc     480
gctggttctg gtgcgggtgc cggagctggt tatggagctg cttctggtgc tggtgccggt     540 gctgggggctg gtgccggagc tggttatgga actggtgcag gtgcaggtgc cggagctggt     600
tatggagctg gtgcaggtgc aggtgccgga gctggttatg ggctggtgc aggtgcaggt      660 gccggagctg gttatggagc tggtgcaggt gcaggtgccg agctggtta tggggctggt      720 gcaggtgcag gtgccggagc tggttatgga gctggtgcgg gtgccggtgc cggggctggt     780
tatggagctg cctctggtgc tggtgctggc gctgggtacg gacaaggagt aggaagcgga     840
gctgcttctg gagctggtgc aggtgcagga gcaggttctg ccgctggttc tggggcaggt     900
gccggtgctg gtaccggtgc tggtgcaggt tacggagctg gtgcaggtgc cggtgccgga     960
gctggttatg gagctgcctc tggtactgga gcaggttatg gagctggtgc cggagctggt    1020 tacgaggtg cctctggtgc tggtgctggt gccggtgctg gggctggagc cggtgctggt     1080
gcaggttatg gaactggcgc tggatacgga gcaggagccg gagcaggagc cggagcagga    1140
gctggtgctg gatacggagc aggagctggt gctggatacg gagcaggata tggagtagga    1200
gctggtgctg gatacggagc aggatacgga gcaggagctg gaagcggagc tgcctctggt    1260
gctggttcag gtgccggtgc tggttcaggt gccggtgctg gttcaggtgc cggtgctggt    1320
tcaggtgccg gtgccggttc aggtgctggt gctggttcag gtgctggtgc tggttcaggt    1380
gctggtgcag gttcaggtgc tggtgctggt tcaggtactg gtgctggttc aggagctggt    1440
gctggatacg gagcaggagc tggtgctgga tacggagcag gagcaggaag tggagctgcc    1500
tctggtgccg gtgctggttc aggtgcaggt gctggttcag gtgctggtgc tggttcaggt    1560
gctggtgctg gttcaggtgc tggtgctggt tcaggagctg gtgctggata cggagcagga    1620
gctggtgctg gatacggagc aggagctggt gctggatacg gagcaggagc tggcgttgga    1680
tacggagcag gagctggaag cggagctgcc tctggtgctg gtgctggttc aggagccggt    1740
gctggttcag gtgctggtgc tggttcaggt gctggtgctg gttcaggtgc tggtgctggt    1800
tcaggtgccg gtgctggttc aggtgctggt gctggttcag gagctggtgc tggttcaggt    1860
gctggtgctg gttcaggagc tggagttgga tacggagcag gagttggtgc tggatacgga    1920
gcaggatatg gagcaggagc tggtgctgga tacggagcag gagcaggaag cggagctgcc    1980
tctggtgctg gtgccggtgc tggagctggt gcaggaacag gctcttctgg atttggacca    2040
tatgtagcaa atgcgggata tagcagaagt gatggctacg aatacgcttg gtcgtctgac    2100 tttgaactg gaagcggagc tggtgctggt tcaggtctg gtgctggttc aggtgctggc      2160
gctggctcag gtgctggtgc tggttcaggt gctggtgctg gttcaggagc tggagctgga    2220
tacggagcag gagttggtgt tggatacgga gcaggatatg gagcaggagc tggtgctgga    2280
tacggagcag gagcaggaag cggagctgcc tctggtgccg gtgctggttc aggtgctggt    2340
```

```
gctggttcag gtgccggtgc tggttcaggt gctggtgctg gttcaggtgc cggtgctggt      2400
tcaggtgctg gtgctggctc aggtgccggt gctggttcag gtgctggtgc tggttcaggt      2460
gccggtgctg gttcaggtgc tggtgctggt tcaggtgctg gtgttggctc aggtgctggt      2520
gctggttcag gtgctggtgc tggcgttgga tacggagcag gagctggcgt tggatacgga      2580
gcaggagctg gaagcggagc tgcctctggt gctggtgctg gttcaggagc cggtgctggt      2640
tcaggtgctg gtgctggttc aggtgctggt gctggttcag gtgctggtgc tggttcaggt      2700
gccggtgctg gttcaggtgc tggtgctggt tcaggagctg gtgctggttc aggtgctggt      2760
gctggttcag gagctggagt tggatacgga gcaggagttg gtgctggata cggagcagga      2820
tatggagcag gagctggtgc tggatacgga gcaggagcag gaagcggagc tgcctcaggt      2880
gccggtgctg gttcaggtgc tggtgctggt tcaggtgccg gtgctggttc aggtgctggt      2940
gctggttcag gtgctggtgc tggttcaggt gctggtgctg gttcaggtgc tggtgctggt      3000
tcaggtgctg gtgctggttc aggtgctggt gctggctcag gtgctggagc tggttcaggt      3060
gctggtgctg gttcaggagc tggagctgga tacggagcag gagctggtgc tggatacgga      3120
gcaggatatg gagcaggagc tggtgctgga tacggagcag gagctggaag cggagctgcc      3180
tctggtgctg gttcaggtgc cggtgctggt tcaggtgccg gtgctggtgc tggttcaggt      3240
gctggtgctg gttcaggtgc tggtgctggt tcaggtgctg gtgctggctc aggtgctgga      3300
gctggttcag gtgctggtgc tggttcagga gctggagctg gatacggagc aggagttggt      3360
gctggatacg gagcaggata tggagcagga gctggtgctg gatacggagc aggagcagga      3420
agcggagctg cctctggtgc cggtgctggt tcaggtgctg gagctggttc aggtgccggt      3480
gctggttcag gtgctggtgc tggttcagga gctggtgctg gttcaggagc tggtgctggt      3540
tcaggtgctg gtgctggttc aggagctgga gttggatacg gagcaggata tggagcagga      3600
gctggtgctg gatacggagc aggagcagga agcggagctg cctctggtgc tggtgccggt      3660
gctggagctg gtgcaggaac aggctcttct ggatttggac catatgtagc acatggcgga      3720
tatagcggct acgaatacgc ttggtcgtca gaatctgact ttggaactgg aagcggagct      3780
ggtgctggtt caggtgctgg tgctggttca ggtgctggtc tggctcaggt gctggtgct       3840 ggttcaggag ctggatacgg agcaggagtt ggtgctggat acggagcagg atatggagca      3900
ggagctggtg ctggatacgg agcaggagca ggaagcggag ctggctcagg tgctggtgct      3960
ggttcaggag ctggagctgg ttcaggtgcc ggtgctggtt caggtgctgg tgctggttca      4020
ggagctggtg ctggttcagg tgctggtgct ggttcaggag ctggtgctgg ttcaggtgcc      4080
ggtgctggtt caggtgctgg tgctggatac ggagcaggat atggagcagg agctggtgct      4140
ggatacggag caggagcagg aagcggagct ggctcaggtg ctggtgctgg ttcaggtgct      4200
ggtgctggtt caggagctgg agctggttca ggtgccggtg ctggttcagg tgctggtgct      4260
ggttcaggtg ctggtgctgg ctcaggtgct ggtgctggtt caggagctgg agctggatac      4320
ggagcaggag ttggtgctgg atacggagca ggatatggag caggagctgg tgctggatac      4380
ggagcaggag caggaagcgg agctggctca ggtgctggtg ctggttcagg agctggagct      4440
ggttcaggtg ctggtgctgg ttcaggtgcc ggtgttggtt caggtgctgg tgctggttca      4500
ggagctggtg ctggttcagg tgccggtgct ggttcaggtg ctggtgctgg atacggagca      4560
ggatatggag caggagctgg tgctggatac ggagcaggag caggaagcgg agctggctca      4620
ggtgctggtg ctggttcagg tgctggtgct ggttcaggag ctggagctgg ttcaggtgcc      4680
```

-continued

```
ggtgctggtt caggtgctgg tgctggttca ggagctggtg ctggttcagg tgctggtgct    4740
ggttcaggag ctggagttgg atacggagca ggagttggtg ctggatacgg agcaggatat    4800
ggagcaggag ctggtgctgg atacggagca ggagcaggaa gcggagctgc ctctggtgct    4860
ggtgccggtg ctggagctgg tgcaggaaca ggctcttctg gatttggacc atatgtagca    4920
aatggcggat atagcggcta cgaatacgct tggtcgtcag aatctgactt tggaactgga    4980
agcggagctg gtgctggttc aggtgctggt gctggttcag gtgctggtgc tggctcaggt    5040
gctggtgctg gttcaggagc tggagctgga tacggagcag gatatggagc aggagctggt    5100
gctggatacg gagcaggagc aggaagcgga gctggctcag gtgctggtgc tggttcagga    5160
gctggagctg gttcaggtgc cggtgctggt tcaggtgctg gtgctggttc aggtgccggt    5220
gctggttcag gtgctggtgc tggttcagga gctggtgctg gttcaggtgc cggttctggt    5280
tcaggagctg gtgctggttc aggtgctggt gctggttcag gagctggagc tggatacgga    5340
gcaggagttg gtgctggata cggagtagga tatggagcag gagctggtgc tggatacgga    5400
gcaggagcag gaagcggagc tgcctctggt gctggtgccg gtgctggagc tggtgcagga    5460
acaggctctt ctggatttgg accatatgta gcacatggcg gatatagcgg ctacgaatac    5520
gcttggtcgt cagaatctga ctttggaact ggaagcggag ctggtgctgg ttcaggtgct    5580
ggtgctggtt caggtgctgg tgctggctca ggtgctggtg ctggttcagg agctggtgct    5640
ggttcaggtg ctggtgctgg ttcaggagct ggagctggat acggagcagg agttggtgct    5700
ggatacggag cagcatatgg agcaggagct ggtgctggat acggagctgg agcaggaagc    5760
ggagctgcct ctggtgccgg tgctggttca ggtgctggtg ctggttcagg tgccggtgct    5820
ggttcaggtg ctggtgctgg ttcaggtgct ggtgctggtt caggtgctgg tgctggttca    5880
ggtgctggtg ctggttcagg agctggtgct ggttcaggag ctggtgctgg ttcaggtgcc    5940
ggtgctggtt caggagctgg agcaggatat ggagcaggag ctggtgctgg atacggagca    6000
ggagcaggaa gcggagctgg ctcaggtgct ggtgctggtt caggtgctgg tgctggttca    6060
ggagctggag ctggttcagg tgccggtgct ggttcaggtg ctggtgctgg ttcaggtgcc    6120
ggttctggtt caggagctgg tgctggttca ggtgctggtg ctggttcagg agctggagct    6180
ggatacggag caggagttgg tgctggatac ggagcaggat atggagcagg agctggtgct    6240
ggatacggag caggagcagg aagcggagct ggctcaggtg ccggtgctgg ttcaggagct    6300
ggagcaggat atggagcagg agctggtgct ggatacggag caggatatgg agcaggagct    6360
ggtgctggat acggagcagg agcaggaacc ggagctggct caggtgctgg tgctggttca    6420
ggtgctggtg ctggttcagg tgctggtgct ggttcaggag ctggagctgg ttcaggtgcc    6480
ggtgctggtt caggtgctgg tgctggttca ggtgccggtt ctggtcagg tgctggtgct    6540 ggttcaggag ctggagctgg ttcaggtgcc ggtgctggtt caggtgctgg tgctggttca    6600
ggtgctggtg ctggttcagg agctggagct ggatacggag caggagctgg tgctggatac    6660
ggagcaggat atggagcagg agctggtgct ggatacggag caggagcagg aagcggtgct    6720
ggttcaggtg ctggtgctgg ttcaggtgct ggtgctggtt caggtgctgg tgctggttca    6780
ggagctggtg ctggatatgg agctggatac ggagcaggac tggaagcgg agctgcctct    6840 ggtgctggtg ccggtgctgg agctggtgca ggaacaggct cttctggatt tggaccatat    6900
gtagcacatg gcggatatag cggctacgaa tacgcttggt cgtcagaatc tgactttgga    6960
actggaagcg gagctggtgc tggttcaggt gctggtgctg gcgcaggtgc tggtgctggt    7020
tcaggagctg gagctggata cggagcagga gttggtgctg gatacggagc aggatatgga    7080
```

```
gcaggagctg gtgctggata cggagcagga gcaggaagcg gaactggctc aggtgctggt      7140
gctggttcag gagctggagc tggatacgga gcaggagttg gtgctggata cggagcagga      7200
gcaggaagcg gagctgcctt tggtgccggt gctggtgctg gtgctggttc aggtgccggt      7260
gctggttcag gtgctggtgc tggttcaggt gctggtgctg gttcaggtgc tggtgctggt      7320
tcaggagctg gtgctggata cggagcaggg tacggagcag gagttggtgc tggatacgga      7380
gcaggagctg gaagcggagc tgcctctggt gccggtgctg gttcaggtgc tggtgctggt      7440
tcaggtgccg gtgctggttc aggtgctggt gctggctcag gtgctggtgc tggttcagga      7500
gctggagctg gatacggagc aggagttggt gctggatacg gagcaggata tggagcagga      7560
gctggtgctg gatacggagc tggagcagga agcggagctg cctctggtgc cggtgctggt      7620
tcaggtgctg gtgctggtgc tggttcaggt gccggtgctg gttcaggtgc tggtgctggt      7680
tcaggtgctg gtgctggttc aggtgctggt tcaggtgctg gtgctggttc aggtgccggt      7740
gctggttcag gagctggtgc tggatacgga gcaggagcag gaagcggagc tgcctctggt      7800
gctggtgccg gtgctggagc tggtgcagga acaggctctt ctggatttgg accatatgta      7860
gcaaatggcg gatatagcgg ctacgaatac gcttggtcgt cagaatctga ctttggaact      7920
ggaagcggag ctggtgctgg ttcaggtgct ggtgctggtt caggtgctgg tgctggctca      7980
ggtgctggtg ctggttcagg agctggagct ggatacggag caggagttgg tgctggatac      8040
ggagcaggat atggagcagg agctggtgct ggatacggag caggagcagg aagcggagct      8100
ggctcaggtg ctggtgctgg ttcaggagct ggagctggtt caggtgccgg tgctggttca      8160
ggtgctggtg ctggttcagg tgccggtgct ggttcaggtg ctggggctgg ttcaggagct      8220
ggtgctggat acggagcagg agcaggaagc ggagctgcct ctggtgccgg tgctggttca      8280
ggtgctggtg ctggttcagg tgccggtgct ggttcaggtg ctggtgctgg ttcaggagct      8340
ggtgctggtt caggtgctgg tgctggttca ggagctggag ctggatacgg agcaggagtt      8400
ggtgctggat acggagtagg atatggagca ggagctggtg ctggatacgg agcaggagca      8460
ggaagcggag ctggctcagg tgctggtgct ggttcaggtg ctggtgctgg ttcaggtgcc      8520
ggtgctggtt caggtgctgg tgctggttca ggtgccggtt caggtgctgg tgctggttca      8580
ggagctggtg ctggttcagg tgctggtgct ggttcaggtg ctggttcagg tgctggtgct      8640
ggctcaggtg ctggtgctgg atacggagta ggatatggag caggagctgg tgctggatac      8700
ggagcaggag caggaagcgg agctggctca ggtgctggtg ctgggtcagg tgccggtgct      8760
ggttcaggtg ctggtgctgg ttcaggtgcc ggttcaggtg ctggtgctgg ttcaggagct      8820
ggtgctggtt caggtgctgg tgctggttca ggagctggag ctggatacgg agcaggagtt      8880
ggtgctggat acggagtagg atatggagca ggagctggtg ctggatacgg agcaggagca      8940
ggaagcggag ctggctcagg tgctggtgct ggttcaggtg ctggtgctgg ttcaggtgcc      9000
ggtgctggtt caggtgctgg tgctggttca ggagctggtg ctggttcagg tgccggtgct      9060
ggttcaggtg ctggtgctgg ttcaggtgcc ggttcaggtg ctggtgctgg ttcaggagct      9120
ggtgctggtt caggtgccgg tgctggttca ggtgctggtg ctggttcagg tgccggttca      9180
ggtgctggtg ctggttcagg agctggtgct ggttcaggtg ctggtgctgg ttcaggagct      9240
ggagctggat acggagcagg agttggtgct ggatacggag taggatatgg agcaggagtt      9300
ggtgctggat acggagcagg agcaggaagc ggagctgcct ctggtgccgg tgctggttca      9360
ggtgctggtg ctggtgctgg ttcaggtgcc ggtgctggtt caggtgctgg tgctggttca      9420
```

-continued

```
ggtgctggtg ctggttcagg tgctggtgct ggttcaggtg ctggtgctgg ttcaggagct      9480
ggtgctggat acggagcagg gtacggagca ggagttggtg ctggatacgg agcaggagct      9540
ggcgttggat acggagcagg agctggcgct ggatacggag caggagctgg aagcggagct      9600
gcctctggtg ccggtgctgg tgctggttca ggtgccggtg ctggtacagg tgctggggct      9660
ggttcaggag ctggtgctgg atacggagca ggagcaggaa gcggagctgc ctctggtgct      9720
ggtgccggtg ctggagctgg tgcaggaaca ggctcttctg gatttggacc atatgtagca      9780
aatggcggat atagcggcta cgaatacgct tggtcgtcag aatctgactt tggaactgga      9840
agcggagctg gtgctggttc aggtgctggt gctggttcag gtgctggtgc tggctcaggt      9900
gctggtgctg gttcaggagc tggagctgga tacggagcag gagttggtgc tggatacgga      9960
gcaggagcag gaagcggagc tggctcaggt gctggtgctg gttcaggagc tggagctggt     10020
tcaggtgctg gtgctggttc aggagctggt gctggttcag gagctggagc tggatacgga     10080
gcaggagcag gaagcggaac tggctcaggt gctggtgctg gttcaggtgc tggtgctggt     10140
tcaggtgccg gtgctggttc aggtgctggt gctggttcag gagctggtgc tggttcaggt     10200
gctggtgctg gttcaggagt tggtgctgga tacggagtag gatatggagc aggagctggt     10260
gctggatacg gagtaggata tggagcagga gctggtgctg gatacggagc aggagcagga     10320
agcggaactg gctcaggtgc tggtgctggt tcaggtgctg gtgctggttc aggtgccggt     10380
gctggttcag gtgctggtgc tggttcagga gctggtgctg gttcaggtgc tggtgctggt     10440
tcaggagctg gagctggata cggagcagga gttggtgctg gatacggagt aggatatgga     10500
gcaggagctg gtgctggata cggagcagga gcaggaagcg gagctggctc aggtgctggt     10560
gctggttcag gtgctggtgc tggttcaggt gccggtgctg gttcaggtgc tggtgctggt     10620
tcaggtgccg gttcaggtgc tggtgctggt tcaggagctg gtgctggttc aggtgctggt     10680
gctggttcag gtgctggttc aggtgctggt gctggctcag gtgctggtgc tggatacgga     10740
gtaggatatg gagcaggagc tggtgctgga tacggagcag gagcaggaag cggagctggc     10800
tcaggtgctg gtgctgggtc aggtgccggt gctggttcag gtgctggtgc tggttcaggt     10860
gccggttcag gtgctggtgc tggttcagga gctggtgctg gttcaggtgc tggtgctggt     10920
tcaggagctg gagctggata cggagcagga gttggtgctg gatacggagt aggatatgga     10980
gcaggagctg gtgctggata cggagcagga gcaggaagcg gagctggctc aggtgctggt     11040
gctggttcag gtgctggtgc tggttcaggt gccggtgctg gttcaggtgc tggtgctggt     11100
tcaggagctg gtgctggttc aggtgccggt gctggttcag gtgctggtgc tggttcaggt     11160
gccggttcag gtgctggtgc tggttcagga gctggtgctg gttcaggtgc tggtgctggt     11220
tcaggagctg gagctggata cggagcagga gttggtgctg gatacggagt aggatatgga     11280
gcaggagctg gtgctggata cggagcagga gcaggaagcg gagctgcctc tggtgctggt     11340
gccggtgctg gagctggtgc aggaacaggc tcttctggat ttggaccata tgtagcaaat     11400
ggcggatata gcggctacga atacgcttgg tcgtcagaat ctgactttgg aactggaagc     11460
ggagctggtg ctggttcagg tgctggtgct ggttcaggag ctggtgctgg atacggagca     11520
gggtacggag caggagttgg tgctggatac ggagcaggag ctggcgttgg atacggagca     11580
ggagctggcg ctggatacgg agcaggagct ggaagcggag ctgcctctgg tgccggtgct     11640
ggtgccggtg ctggtgctgg ttcaggtgcc ggtgctggtt caggtgctgg tgctggtgct     11700
ggttcaggag ctggtgctgg atacggagca gggtacggaa taggagttgg tgctggatac     11760
ggagcaggag ctggcgttgg atacggagca ggagctggcg ctggatacgg agcaggagct     11820
```

```
ggaagcggag ctgcctctgg tgccggtgct ggttcaggtg ctggtgctgg ttcaggtgct   11880
ggtgctggtt caggtgctgg tgctggttca ggtgctggtg ctggttcagg tgctggtgct   11940
ggttcaggag ctggtgctgg atacggagca gggtacggag caggagttgg tgctggatac   12000
ggagcaggag ctggcgttgg atacggagca ggagctggcg ctggatacgg agcaggagct   12060
ggaagcggag ctgcctctgg tgccggtgct ggtgccggtg ctggtgctgg tgctggttca   12120
ggtgccggtg ctggttcagg tgctggtgct ggttcaggtg ctggtgctgg ttcaggagct   12180
ggtgctggtt caggtgctgg tgctggttca ggtgctggtg ctggttcagg tgctggtgct   12240
ggctcaggtg ctggtgctgg ttcaggagct ggagctggat acggagcagg agttggtgct   12300
ggatacggag caggatatgg aggagctggt gctggatacg gagcaggagc aggaagcgga   12360
gctgcctctg gtgccggtgc tggttcaggt gctggtgctg gttcaggagc tggtgctggt   12420
tcaggtgctg gtgctggttc aggtgctggg ctggttcag gtgctggtgc tggatacgga   12480
gcaggagcag gaagcggagc tgcctctggt gctggtgccg gtgctggagc tggtgcagga   12540
acaggctctt ctggatttgg accatatgta aatggcggat atagcggcta cgaatacgct   12600
tggtcgtcag aatctgactt tggaactgga agcggagctg gtgctggctc aggtgctggt   12660
gctggttcag gagctggagc tggatacgga gcaggagttg gtgctggata cggagcagga   12720
tatggagcag gagctggtgc tggatacgga gcaggagcag gaagcggagc tgcctctggt   12780
gccggtgctg gttcaggtgc tggtgctggt tcaggtgccg gtgctggttc aggtgctggt   12840
gctggttcag gtgctggttc aggtgctggt gctggttcag gtgctggtgc tggttcaggt   12900
gctggtgctg gttcaggtgc tggtgctggt tcaggtgctg gtgctggttc aggagctgga   12960
gctggatacg gagcaggagt tggtgctgga tacggagcag gatatggagc aggagctggt   13020
gctggatacg gagcaggagc aggaagcgga gctgcytctg gcgccggtgc tggttcaggt   13080
gctggtgctg gtgctggttc aggtgccggt gctggttcag gtgctggtgc tggttcaggt   13140
gctggtgctg gttcaggtgc tggtgctggt tcaggtgctg gtgctggttc aggtgctggt   13200
tcaggtgctg gtgctggttc aggagctggt gctggatacg gagcagggta cggagcagga   13260
gttggtgctg gatacggagc aggagctggc gttggatacg gagcaggagc tggcgctgga   13320
tacggagcag gagctggaag cggagctgcc tctggtgccg gtgctggttc aggttctggt   13380
gctggttcag gtgccggtgc tggttcaggt gctggtgctg gttcaggtgc tggtgctggt   13440
gctggttcag gtgctggggc tggttcagga gctggtgctg gttcaggagc tggtgctgga   13500
tacggagcag ggtacggagc aggagcagga agcggagctg cctctggtgc tggtgccggt   13560
gctggagctg gtgcaggaac aggctcttct ggatttggac catatgtagc aaatggcgga   13620
tatagcggct acgaatacgc ttggtcgtca gaatctgact ttggaactgg aagcggagct   13680
ggtgctggct caggtgctgg tgctggttca ggagctggag ctggatacgg agcaggagtt   13740
ggtgctggtt acggagcagg atatggagca ggagctggtg ctggatacgg agcaggagca   13800
ggaagcggag ctggctcagg tgccggtgct ggttcaggtg ctggtgctgg ttcaggtgcc   13860
ggtgctggtt caggtgctgg tgctggttca ggagctggtg ctggttcagg tgctggtgct   13920
ggttcaggtg ctggtgctgg ttcaggtgct ggtgctggat acggagcagg atacggagca   13980
ggagctggtg ctggatacgg agcaggagct ggcgttggat acggagcagg agctggcgct   14040
ggatacggag caggagctgg aagcggagct ggctctggtg ccggtgctgg ttcaggttct   14100
ggtgctggtg ctggttcagg ttctggtgct ggttcaggtg ctggtgctgg ttcaggtgct   14160
```

| | | | | | | | | | | |
|---|---|---|---|---|---|---|---|---|---|---|
| ggtgctggtt | caggtgctgg | tgctggttca | ggagctggtg | ctggttcagg | tgctggtgct | 14220 |
| ggttcaggtg | ctggtgctgg | ttcaggtgct | ggtgctggat | acggagcagg | gtacggaata | 14280 |
| ggagttggtg | ctggatacgg | agcaggagct | ggcgttggat | acggagcagg | agctggcgct | 14340 |
| ggatacggag | caggagctgg | aagcggagct | gcctctggtg | ccggtgctgg | ttcaggtgct | 14400 |
| ggtgctggtt | caggagctgg | tgctggttca | ggtgctggtg | ctggttcagg | tgctggtgct | 14460 |
| ggttcaggtg | ctggtgctgg | ttcaggagct | ggtgctggtt | caggtgctgg | tgctggttca | 14520 |
| ggtgctggtg | ctggttcagg | agctggtgct | ggatacggag | caggagctgg | cgttggatac | 14580 |
| ggagcaggag | ctggaagcgg | agctgcctct | ggtgctggtg | ctggttcagg | tgctggtgct | 14640 |
| ggttcaggtg | ctggtgctgg | ttcaggtgct | ggtgctggtt | caggtgctgg | tgctggttca | 14700 |
| ggtgctggtg | ctggttcagg | tgctggtgct | ggttcaggtg | ctggttcagg | tgctggtgct | 14760 |
| ggctcaggtg | ctggtgctgg | atacggagca | gggtacggag | caggagttgg | tgctggatac | 14820 |
| ggagcaggtg | ctggatacgg | agcaggatat | ggagtaggag | ctggtgctgg | atacggagca | 14880 |
| ggagcaggaa | gcggagctgg | ctctggtgct | ggtgctggtt | caggtgctgg | tgctggttca | 14940 |
| ggtgctggtg | ctggttcagg | tgctggtgct | ggttcaggtg | ctggtgctgg | ttcaggtgct | 15000 |
| ggttcaggag | ctggtgctgg | atacggagca | ggagctggcg | ctggatacgg | agcaggagct | 15060 |
| ggcgctggat | acggagcagg | agctggaagc | ggagctgcct | ctggtgctgg | tgctggtgcc | 15120 |
| ggtgctggtt | caggtgctgg | tgctggttca | ggtgctggtg | ctggttcagg | tgctggttca | 15180 |
| ggtgctggtg | ctggttcagg | agctggtgct | ggatacggag | caggagctgg | aagcggagct | 15240 |
| gcctctggtg | ccggtgctgg | ttcaggtgct | ggtgctggtg | ctggtgccgg | tgctggtgct | 15300 |
| ggttcaggag | ctggtgctgg | ttcaggagct | ggtgctggat | acggagcagg | agcaggaagt | 15360 |
| ggagctgcct | ctggtgctgg | tgctggagct | ggtgcaggaa | caggctcttc | tggatttgga | 15420 |
| ccatatgtag | caaatggcgg | atatagcaga | cgtgaaggct | acgaatacgc | ttggtcgtca | 15480 |
| aaatctgact | ttgaaactgg | aagcggtgct | gcctctggtg | ctggtgctgg | tgctggttca | 15540 |
| ggtgctggtg | ctggttcagg | tgccggtgct | ggttcaggtg | ctggtgctgg | ttcaggtgcc | 15600 |
| ggtgctggtg | gtagcgtcag | ttacggagct | ggcaggggat | acggacaagg | tgcaggaagt | 15660 |
| gcagcttcct | ctgtgtcatc | tgcttcatct | cgcagttacg | actattctcg | tcgtaacgtc | 15720 |
| cgcaaaaact | gtggaattcc | tagaagacaa | ctagttgtta | aattcagagc | actgccttgt | 15780 |
| gtgaattgct | aa | | | | | 15792 |

<210> SEQ ID NO 30
<211> LENGTH: 5263
<212> TYPE: PRT
<213> ORGANISM: Bombyx mori

<400> SEQUENCE: 30

Met Arg Val Lys Thr Phe Val Ile Leu Cys Cys Ala Leu Gln Tyr Val
1               5                   10                  15

Ala Tyr Thr Asn Ala Asn Ile Asn Asp Phe Asp Glu Asp Tyr Phe Gly
            20                  25                  30

Ser Asp Val Thr Val Gln Ser Ser Asn Thr Thr Asp Glu Ile Ile Arg
        35                  40                  45

Asp Ala Ser Gly Ala Val Ile Glu Glu Gln Ile Thr Thr Lys Lys Met
    50                  55                  60

Gln Arg Lys Asn Lys Asn His Gly Ile Leu Gly Lys Asn Glu Lys Met
65                  70                  75                  80

-continued

```
Ile Lys Thr Phe Val Ile Thr Thr Asp Ser Asp Gly Asn Glu Ser Ile
                 85                  90                  95
Val Glu Glu Asp Val Leu Met Lys Thr Leu Ser Asp Gly Thr Val Ala
            100                 105                 110
Gln Ser Tyr Val Ala Ala Asp Ala Gly Ala Tyr Ser Gln Ser Gly Pro
        115                 120                 125
Tyr Val Ser Asn Ser Gly Tyr Ser Thr His Gln Gly Tyr Thr Ser Asp
    130                 135                 140
Phe Ser Thr Ser Ala Ala Val Gly Ala Gly Ala Gly Ala Gly Ala Ala
145                 150                 155                 160
Ala Gly Ser Gly Ala Gly Ala Gly Ala Gly Tyr Gly Ala Ala Ser Gly
                165                 170                 175
Ala Gly Ala Gly Ala Gly Ala Gly Ala Gly Ala Gly Tyr Gly Thr Gly
            180                 185                 190
Ala Gly Ala Gly Ala Gly Ala Gly Tyr Gly Ala Gly Ala Gly Ala Gly
        195                 200                 205
Ala Gly Ala Gly Tyr Gly Ala Gly Ala Gly Ala Gly Ala Gly Ala Gly
    210                 215                 220
Tyr Gly Ala Gly Ala Gly Ala Gly Ala Gly Ala Gly Tyr Gly Ala Gly
225                 230                 235                 240
Ala Gly Ala Gly Ala Gly Ala Gly Tyr Gly Ala Gly Ala Gly Ala Gly
                245                 250                 255
Ala Gly Ala Gly Tyr Gly Ala Ala Ser Gly Ala Gly Ala Gly Ala Gly
            260                 265                 270
Tyr Gly Gln Gly Val Gly Ser Gly Ala Ala Ser Gly Ala Gly Ala Gly
        275                 280                 285
Ala Gly Ala Gly Ser Ala Ala Gly Ser Gly Ala Gly Ala Gly Ala Gly
    290                 295                 300
Thr Gly Ala Gly Ala Gly Tyr Gly Ala Gly Ala Gly Ala Gly Ala Gly
305                 310                 315                 320
Ala Gly Tyr Gly Ala Ala Ser Gly Thr Gly Ala Gly Tyr Gly Ala Gly
                325                 330                 335
Ala Gly Ala Gly Tyr Gly Gly Ala Ser Gly Ala Gly Ala Gly Ala Gly
            340                 345                 350
Ala Gly Ala Gly Ala Gly Ala Gly Ala Gly Tyr Gly Thr Gly Ala Gly
        355                 360                 365
Tyr Gly Ala Gly Ala Gly Ala Gly Ala Gly Ala Gly Ala Gly Ala Gly
    370                 375                 380
Tyr Gly Ala Gly Ala Gly Ala Gly Tyr Gly Ala Gly Tyr Gly Val Gly
385                 390                 395                 400
Ala Gly Ala Gly Tyr Gly Ala Gly Tyr Gly Ala Gly Ala Gly Ser Gly
                405                 410                 415
Ala Ala Ser Gly Ala Gly Ser Gly Ala Gly Ala Gly Ser Gly Ala Gly
            420                 425                 430
Ala Gly Ser Gly Ala Gly Ala Gly Ser Gly Ala Gly Ala Gly Ser Gly
        435                 440                 445
Ala Gly Ala Gly Ser Gly Ala Gly Ala Gly Ser Gly Ala Gly Ala Gly
    450                 455                 460
Ser Gly Ala Gly Ala Gly Ser Gly Thr Gly Ala Gly Ser Gly Ala Gly
465                 470                 475                 480
Ala Gly Tyr Gly Ala Gly Ala Gly Ala Gly Tyr Gly Ala Gly Ala Gly
                485                 490                 495
Ser Gly Ala Ala Ser Gly Ala Gly Ala Gly Ser Gly Ala Gly Ala Gly
```

-continued

```
            500                 505                 510
Ser Gly Ala Gly Ala Gly Ser Gly Ala Gly Ser Gly Ala Gly
        515                 520                 525
Ala Gly Ser Gly Ala Gly Ala Gly Tyr Gly Ala Gly Ala Gly
        530                 535                 540
Tyr Gly Ala Gly Ala Gly Ala Gly Tyr Gly Ala Gly Val Gly
545                 550                 555                 560
Tyr Gly Ala Gly Ala Gly Ser Gly Ala Ala Ser Gly Ala Gly
        565                 570                 575
Ser Gly Ala Gly Ala Gly Ser Gly Ala Gly Ala Gly Ser Gly Ala Gly
        580                 585                 590
Ala Gly Ser Gly Ala Gly Ala Gly Ser Gly Ala Gly Ala Gly Ser Gly
        595                 600                 605
Ala Gly Ala Gly Ser Gly Ala Gly Ala Gly Ser Gly Ala Gly Ala Gly
        610                 615                 620
Ser Gly Ala Gly Val Gly Tyr Gly Ala Gly Val Gly Ala Gly Tyr Gly
625                 630                 635                 640
Ala Gly Tyr Gly Ala Gly Ala Gly Ala Gly Tyr Gly Ala Gly Ala Gly
        645                 650                 655
Ser Gly Ala Ala Ser Gly Ala Gly Ala Gly Ala Gly Ala Gly
        660                 665                 670
Thr Gly Ser Ser Gly Phe Gly Pro Tyr Val Ala Asn Gly Gly Tyr Ser
        675                 680                 685
Arg Ser Asp Gly Tyr Glu Tyr Ala Trp Ser Ser Asp Phe Gly Thr Gly
        690                 695                 700
Ser Gly Ala Gly Ala Gly Ser Gly Ala Gly Ala Gly Ser Gly Ala Gly
705                 710                 715                 720
Ala Gly Ser Gly Ala Gly Ala Gly Ser Gly Ala Gly Ala Gly Ser Gly
        725                 730                 735
Ala Gly Ala Gly Tyr Gly Ala Gly Val Gly Val Gly Tyr Gly Ala Gly
        740                 745                 750
Tyr Gly Ala Gly Ala Gly Ala Gly Tyr Gly Ala Gly Ala Gly Ser Gly
        755                 760                 765
Ala Ala Ser Gly Ala Gly Ala Gly Ser Gly Ala Gly Ala Gly Ser Gly
        770                 775                 780
Ala Gly Ala Gly Ser Gly Ala Gly Ala Gly Ser Gly Ala Gly Ala Gly
785                 790                 795                 800
Ser Gly Ala Gly Ala Gly Ser Gly Ala Gly Ala Gly Ser Gly Ala Gly
        805                 810                 815
Ala Gly Ser Gly Ala Gly Ala Gly Ser Gly Ala Gly Ala Gly Ser Gly
        820                 825                 830
Ala Gly Val Gly Ser Gly Ala Gly Ala Gly Ser Gly Ala Gly Ala Gly
        835                 840                 845
Val Gly Tyr Gly Ala Gly Ala Gly Val Gly Tyr Gly Ala Gly Ala Gly
        850                 855                 860
Ser Gly Ala Ala Ser Gly Ala Gly Ala Gly Ser Gly Ala Gly Ala Gly
865                 870                 875                 880
Ser Gly Ala Gly Ala Gly Ser Gly Ala Gly Ala Gly Ser Gly Ala Gly
        885                 890                 895
Ala Gly Ser Gly Ala Gly Ala Gly Ser Gly Ala Gly Ala Gly Ser Gly
        900                 905                 910
Ala Gly Ala Gly Ser Gly Ala Gly Ala Gly Ser Gly Ala Gly Val Gly
        915                 920                 925
```

Tyr Gly Ala Gly Val Gly Ala Gly Tyr Gly Ala Gly
        930                 935                 940

Ala Gly Ala Gly Tyr Gly Ala Gly Ala Gly Ser Ala Ala Ser Gly
945                 950                 955                 960

Ala Gly Ala Gly Ser Gly Ala Gly Ala Gly Ser Gly Ala Gly Ala Gly
                965                 970                 975

Ser Gly Ala Gly Ala Gly Ser Gly Ala Gly Ala Gly Ser Gly Ala Gly
            980                 985                 990

Ala Gly Ser Gly Ala Gly Ala Gly Ser Gly Ala Gly Ala Gly Ser Gly
            995                 1000                1005

Ala Gly Ala Gly Ser Gly Ala Gly Ala Gly Ser Gly Ala Gly Ala
        1010                1015                1020

Gly Ser Gly Ala Gly Ala Gly Tyr Gly Ala Gly Ala Gly Ala Gly
        1025                1030                1035

Tyr Gly Ala Gly Tyr Gly Ala Gly Ala Gly Ala Gly Tyr Gly Ala
        1040                1045                1050

Gly Ala Gly Ser Gly Ala Ala Ser Gly Ala Gly Ser Gly Ala Gly
        1055                1060                1065

Ala Gly Ser Gly Ala Gly Ala Gly Ala Gly Ser Gly Ala Gly Ala
        1070                1075                1080

Gly Ser Gly Ala Gly Ala Gly Ser Gly Ala Gly Ala Gly Ser Gly
        1085                1090                1095

Ala Gly Ala Gly Ser Gly Ala Gly Ala Gly Ser Gly Ala Gly Ala
        1100                1105                1110

Gly Tyr Gly Ala Gly Val Gly Ala Gly Tyr Gly Ala Gly Tyr Gly
        1115                1120                1125

Ala Gly Ala Gly Ala Gly Tyr Gly Ala Gly Ala Gly Ser Gly Ala
        1130                1135                1140

Ala Ser Gly Ala Gly Ala Gly Ser Gly Ala Gly Ala Gly Ser Gly
        1145                1150                1155

Ala Gly Ala Gly Ser Gly Ala Gly Ala Gly Ser Gly Ala Gly Ala
        1160                1165                1170

Gly Ser Gly Ala Gly Ala Gly Ser Gly Ala Gly Ala Gly Ser Gly
        1175                1180                1185

Ala Gly Val Gly Tyr Gly Ala Gly Tyr Gly Ala Gly Ala Gly Ala
        1190                1195                1200

Gly Tyr Gly Ala Gly Ala Gly Ser Gly Ala Ala Ser Gly Ala Gly
        1205                1210                1215

Ala Gly Ala Gly Ala Gly Ala Gly Thr Gly Ser Ser Gly Phe Gly
        1220                1225                1230

Pro Tyr Val Ala His Gly Gly Tyr Ser Gly Tyr Glu Tyr Ala Trp
        1235                1240                1245

Ser Ser Glu Ser Asp Phe Gly Thr Gly Ser Gly Ala Gly Ala Gly
        1250                1255                1260

Ser Gly Ala Gly Ala Gly Ser Gly Ala Gly Ala Gly Ser Gly Ala
        1265                1270                1275

Gly Ala Gly Ser Gly Ala Gly Tyr Gly Ala Gly Val Gly Ala Gly
        1280                1285                1290

Tyr Gly Ala Gly Tyr Gly Ala Gly Ala Gly Ala Gly Tyr Gly Ala
        1295                1300                1305

Gly Ala Gly Ser Gly Ala Gly Ser Gly Ala Gly Ala Gly Ser Gly
        1310                1315                1320

-continued

```
Ala Gly Ala Gly Ser Gly Ala  Gly Ala Gly Ser  Gly Ala Gly Ala
    1325                1330                1335
Gly Ser Gly Ala Gly Ala Gly  Ser Gly Ala Gly  Ala Gly Ser Gly
    1340                1345                1350
Ala Gly Ala Gly Ser Gly Ala  Gly Ala Gly Ser  Gly Ala Gly Ala
    1355                1360                1365
Gly Tyr Gly Ala Gly Tyr Gly  Ala Gly Ala Gly  Ala Gly Tyr Gly
    1370                1375                1380
Ala Gly Ala Gly Ser Gly Ala  Gly Ser Gly Ala  Gly Ala Gly Ser
    1385                1390                1395
Gly Ala Gly Ala Gly Ser Gly  Ala Gly Ala Gly Ser  Gly Ala Gly
    1400                1405                1410
Ala Gly Ser Gly Ala Gly Ala  Gly Ser Gly Ala Gly  Ala Gly Ser
    1415                1420                1425
Gly Ala Gly Ala Gly Ser Gly  Ala Gly Ala Gly Tyr  Gly Ala Gly
    1430                1435                1440
Val Gly Ala Gly Tyr Gly Ala  Gly Tyr Gly Ala Gly  Ala Gly Ala
    1445                1450                1455
Gly Tyr Gly Ala Gly Ala Gly  Ser Gly Ala Gly Ser  Gly Ala Gly
    1460                1465                1470
Ala Gly Ser Gly Ala Gly Ala  Gly Ser Gly Ala Gly  Ala Gly Ser
    1475                1480                1485
Gly Ala Gly Val Gly Ser Gly  Ala Gly Ala Gly Ser  Gly Ala Gly
    1490                1495                1500
Ala Gly Ser Gly Ala Gly Ala  Gly Ser Gly Ala Gly  Ala Gly Tyr
    1505                1510                1515
Gly Ala Gly Tyr Gly Ala Gly  Ala Gly Ala Gly Tyr  Gly Ala Gly
    1520                1525                1530
Ala Gly Ser Gly Ala Gly Ser  Gly Ala Gly Ala Gly  Ser Gly Ala
    1535                1540                1545
Gly Ala Gly Ser Gly Ala Gly  Ala Gly Ser Gly Ala  Gly Ala Gly
    1550                1555                1560
Ser Gly Ala Gly Ala Gly Ser  Gly Ala Gly Ala Gly  Ser Gly Ala
    1565                1570                1575
Gly Ala Gly Ser Gly Ala Gly  Val Gly Tyr Gly Ala  Gly Val Gly
    1580                1585                1590
Ala Gly Tyr Gly Ala Gly Tyr  Gly Ala Gly Ala Gly  Ala Gly Tyr
    1595                1600                1605
Gly Ala Gly Ala Gly Ser Gly  Ala Ala Ser Gly Ala  Gly Ala Gly
    1610                1615                1620
Ala Gly Ala Gly Ala Gly Thr  Gly Ser Ser Gly Phe  Gly Pro Tyr
    1625                1630                1635
Val Ala Asn Gly Gly Tyr Ser  Gly Tyr Glu Tyr Ala  Trp Ser Ser
    1640                1645                1650
Glu Ser Asp Phe Gly Thr Gly  Ser Gly Ala Gly Ala  Gly Ser Gly
    1655                1660                1665
Ala Gly Ala Gly Ser Gly Ala  Gly Ala Gly Ser Gly  Ala Gly Ala
    1670                1675                1680
Gly Ser Gly Ala Gly Ala Gly  Tyr Gly Ala Gly Tyr  Gly Ala Gly
    1685                1690                1695
Ala Gly Ala Gly Tyr Gly Ala  Gly Ala Gly Ser Gly  Ala Gly Ser
    1700                1705                1710
Gly Ala Gly Ala Gly Ser Gly  Ala Gly Ala Gly Ser  Gly Ala Gly
```

```
            1715                1720                1725

Ala Gly Ser Gly Ala Gly Ala Gly Ser Gly Ala Gly Ala Gly Ser
            1730                1735                1740

Gly Ala Gly Ala Gly Ser Gly Ala Gly Ala Ser Gly Ala Gly
            1745                1750                1755

Ser Gly Ser Gly Ala Gly Ala Gly Ser Gly Ala Gly Ala Gly Ser
            1760                1765                1770

Gly Ala Gly Ala Gly Tyr Gly Ala Gly Val Gly Ala Gly Tyr Gly
            1775                1780                1785

Val Gly Tyr Gly Ala Gly Ala Gly Ala Gly Tyr Gly Ala Gly Ala
            1790                1795                1800

Gly Ser Gly Ala Ala Ser Gly Ala Gly Ala Gly Ala Gly Ala Gly
            1805                1810                1815

Ala Gly Thr Gly Ser Ser Gly Phe Gly Pro Tyr Val Ala His Gly
            1820                1825                1830

Gly Tyr Ser Gly Tyr Glu Tyr Ala Trp Ser Ser Glu Ser Asp Phe
            1835                1840                1845

Gly Thr Gly Ser Gly Ala Gly Ala Gly Ser Gly Ala Gly Ala Gly
            1850                1855                1860

Ser Gly Ala Gly Ala Gly Ser Gly Ala Gly Ala Gly Ser Gly Ala
            1865                1870                1875

Gly Ala Gly Ser Gly Ala Gly Ala Gly Ser Gly Ala Gly Ala Gly
            1880                1885                1890

Tyr Gly Ala Gly Val Gly Ala Gly Tyr Gly Ala Ala Tyr Gly Ala
            1895                1900                1905

Gly Ala Gly Ala Gly Tyr Gly Ala Gly Ala Gly Ser Gly Ala Ala
            1910                1915                1920

Ser Gly Ala Gly Ala Gly Ser Gly Ala Gly Ala Gly Ser Gly Ala
            1925                1930                1935

Gly Ala Gly Ser Gly Ala Gly Ala Gly Ser Gly Ala Gly Ala Gly
            1940                1945                1950

Ser Gly Ala Gly Ala Gly Ser Gly Ala Gly Ala Gly Ser Gly Ala
            1955                1960                1965

Gly Ala Gly Ser Gly Ala Gly Ala Gly Ser Gly Ala Gly Ala Gly
            1970                1975                1980

Ser Gly Ala Gly Ala Gly Tyr Gly Ala Gly Ala Gly Ala Gly Tyr
            1985                1990                1995

Gly Ala Gly Ala Gly Ser Gly Ala Gly Ser Gly Ala Gly Ala Gly
            2000                2005                2010

Ser Gly Ala Gly Ala Gly Ser Gly Ala Gly Ala Gly Ser Gly Ala
            2015                2020                2025

Gly Ala Gly Ser Gly Ala Gly Ala Gly Ser Gly Ala Gly Ser Gly
            2030                2035                2040

Ser Gly Ala Gly Ala Gly Ser Gly Ala Gly Ala Gly Ser Gly Ala
            2045                2050                2055

Gly Ala Gly Tyr Gly Ala Gly Val Gly Ala Gly Tyr Gly Ala Gly
            2060                2065                2070

Tyr Gly Ala Gly Ala Gly Ala Gly Tyr Gly Ala Gly Ala Gly Ser
            2075                2080                2085

Gly Ala Gly Ser Gly Ala Gly Ala Gly Ser Gly Ala Gly Ala Gly
            2090                2095                2100

Tyr Gly Ala Gly Ala Gly Ala Gly Tyr Gly Ala Gly Tyr Gly Ala
            2105                2110                2115
```

```
Gly Ala Gly Ala Gly Tyr Gly Ala Gly Ala Thr Gly Ala Gly
    2120            2125            2130

Ser Gly Ala Gly Ala Gly Ser Gly Ala Gly Ala Ser Gly Ala
    2135            2140            2145

Gly Ala Gly Ser Gly Ala Gly Ala Gly Ser Gly Ala Gly Ala Gly
    2150            2155            2160

Ser Gly Ala Gly Ala Gly Ser Gly Ala Gly Ser Gly Ser Gly Ala
    2165            2170            2175

Gly Ala Gly Ser Gly Ala Gly Ala Gly Ser Gly Ala Gly Ala Gly
    2180            2185            2190

Ser Gly Ala Gly Ala Gly Ser Gly Ala Gly Ala Gly Ser Gly Ala
    2195            2200            2205

Gly Ala Gly Tyr Gly Ala Gly Ala Gly Ala Gly Tyr Gly Ala Gly
    2210            2215            2220

Tyr Gly Ala Gly Ala Gly Ala Gly Tyr Gly Ala Gly Ala Gly Ser
    2225            2230            2235

Gly Ala Gly Ser Gly Ala Gly Ala Gly Ser Gly Ala Gly Ala Gly
    2240            2245            2250

Ser Gly Ala Gly Ala Gly Ser Gly Ala Gly Ala Gly Tyr Gly Ala
    2255            2260            2265

Gly Tyr Gly Ala Gly Ala Gly Ser Gly Ala Ala Ser Gly Ala Gly
    2270            2275            2280

Ala Gly Ala Gly Ala Gly Ala Gly Thr Gly Ser Ser Gly Phe Gly
    2285            2290            2295

Pro Tyr Val Ala His Gly Gly Tyr Ser Gly Tyr Glu Tyr Ala Trp
    2300            2305            2310

Ser Ser Glu Ser Asp Phe Gly Thr Gly Ser Gly Ala Gly Ala Gly
    2315            2320            2325

Ser Gly Ala Gly Ala Gly Ala Gly Ala Gly Ala Gly Ser Gly Ala
    2330            2335            2340

Gly Ala Gly Tyr Gly Ala Gly Val Gly Ala Gly Tyr Gly Ala Gly
    2345            2350            2355

Tyr Gly Ala Gly Ala Gly Ala Gly Tyr Gly Ala Gly Ala Gly Ser
    2360            2365            2370

Gly Thr Gly Ser Gly Ala Gly Ala Gly Ser Gly Ala Gly Ala Gly
    2375            2380            2385

Tyr Gly Ala Gly Val Gly Ala Gly Tyr Gly Ala Gly Ala Gly Ser
    2390            2395            2400

Gly Ala Ala Phe Gly Ala Gly Ala Gly Ala Gly Ala Gly Ser Gly
    2405            2410            2415

Ala Gly Ala Gly Ser Gly Ala Gly Ala Gly Ser Gly Ala Gly Ala
    2420            2425            2430

Gly Ser Gly Ala Gly Ala Gly Ser Gly Ala Gly Ala Gly Tyr Gly
    2435            2440            2445

Ala Gly Tyr Gly Ala Gly Val Gly Ala Gly Tyr Gly Ala Gly Ala
    2450            2455            2460

Gly Ser Gly Ala Ala Ser Gly Ala Gly Ala Gly Ser Gly Ala Gly
    2465            2470            2475

Ala Gly Ser Gly Ala Gly Ala Gly Ser Gly Ala Gly Ala Gly Ser
    2480            2485            2490

Gly Ala Gly Ala Gly Ser Gly Ala Gly Ala Gly Tyr Gly Ala Gly
    2495            2500            2505
```

```
Val Gly Ala Gly Tyr Gly Ala Gly Tyr Gly Ala Gly Ala Gly Ala
2510                2515                2520

Gly Tyr Gly Ala Gly Ala Gly Ser Gly Ala Ala Ser Gly Ala Gly
2525                2530                2535

Ala Gly Ser Gly Ala Gly Ala Gly Ala Gly Ser Gly Ala Gly Ala
2540                2545                2550

Gly Ser Gly Ala Gly Ala Gly Ser Gly Ala Gly Ala Gly Ser Gly
2555                2560                2565

Ala Gly Ser Gly Ala Gly Ala Gly Ser Gly Ala Gly Ala Gly Ser
2570                2575                2580

Gly Ala Gly Ala Gly Tyr Gly Ala Gly Ala Gly Ser Gly Ala Ala
2585                2590                2595

Ser Gly Ala Gly Ala Gly Ala Gly Ala Gly Ala Gly Thr Gly Ser
2600                2605                2610

Ser Gly Phe Gly Pro Tyr Val Ala Asn Gly Gly Tyr Ser Gly Tyr
2615                2620                2625

Glu Tyr Ala Trp Ser Ser Glu Ser Asp Phe Gly Thr Gly Ser Gly
2630                2635                2640

Ala Gly Ala Gly Ser Gly Ala Gly Ala Gly Ser Gly Ala Gly Ala
2645                2650                2655

Gly Ser Gly Ala Gly Ala Gly Ser Gly Ala Gly Ala Gly Tyr Gly
2660                2665                2670

Ala Gly Val Gly Ala Gly Tyr Gly Ala Gly Tyr Gly Ala Gly Ala
2675                2680                2685

Gly Ala Gly Tyr Gly Ala Gly Ala Gly Ser Gly Ala Gly Ser Gly
2690                2695                2700

Ala Gly Ala Gly Ser Gly Ala Gly Ala Gly Ser Gly Ala Gly Ala
2705                2710                2715

Gly Ser Gly Ala Gly Ala Gly Ser Gly Ala Gly Ala Gly Ser Gly
2720                2725                2730

Ala Gly Ala Gly Ser Gly Ala Gly Ala Gly Tyr Gly Ala Gly Ala
2735                2740                2745

Gly Ser Gly Ala Ala Ser Gly Ala Gly Ala Gly Ser Gly Ala Gly
2750                2755                2760

Ala Gly Ser Gly Ala Gly Ala Gly Ser Gly Ala Gly Ala Gly Ser
2765                2770                2775

Gly Ala Gly Ala Gly Ser Gly Ala Gly Ala Gly Ser Gly Ala Gly
2780                2785                2790

Ala Gly Tyr Gly Ala Gly Val Gly Ala Gly Tyr Gly Val Gly Tyr
2795                2800                2805

Gly Ala Gly Ala Gly Ala Gly Tyr Gly Ala Gly Ala Gly Ser Gly
2810                2815                2820

Ala Gly Ser Gly Ala Gly Ala Gly Ser Gly Ala Gly Ala Gly Ser
2825                2830                2835

Gly Ala Gly Ala Gly Ser Gly Ala Gly Ala Gly Ser Gly Ala Gly
2840                2845                2850

Ser Gly Ala Gly Ala Gly Ser Gly Ala Gly Ala Gly Ser Gly Ala
2855                2860                2865

Gly Ala Gly Ser Gly Ala Gly Ser Gly Ala Gly Ala Gly Ser Gly
2870                2875                2880

Ala Gly Ala Gly Tyr Gly Val Gly Tyr Gly Ala Gly Ala Gly Ala
2885                2890                2895

Gly Tyr Gly Ala Gly Ala Gly Ser Gly Ala Gly Ser Gly Ala Gly
```

```
                    2900               2905               2910

Ala Gly Ser Gly Ala Gly Ala Gly Ser Gly Ala Gly Ala Gly Ser
        2915               2920               2925

Gly Ala Gly Ser Gly Ala Gly Ala Gly Ser Gly Ala Gly Ala Gly
        2930               2935               2940

Ser Gly Ala Gly Ala Gly Ser Gly Ala Gly Ala Gly Tyr Gly Ala
        2945               2950               2955

Gly Val Gly Ala Gly Tyr Gly Val Gly Tyr Gly Ala Gly Ala Gly
        2960               2965               2970

Ala Gly Tyr Gly Ala Gly Ala Gly Ser Gly Ala Gly Ser Gly Ala
        2975               2980               2985

Gly Ala Gly Ser Gly Ala Gly Ala Gly Ser Gly Ala Gly Ala Gly
        2990               2995               3000

Ser Gly Ala Gly Ala Gly Ser Gly Ala Gly Ala Gly Ser Gly Ala
        3005               3010               3015

Gly Ala Gly Ser Gly Ala Gly Ala Gly Ser Gly Ala Gly Ser Gly
        3020               3025               3030

Ala Gly Ala Gly Ser Gly Ala Gly Ala Gly Ser Gly Ala Gly Ala
        3035               3040               3045

Gly Ser Gly Ala Gly Ala Gly Ser Gly Ala Gly Ser Gly Ala Gly
        3050               3055               3060

Ala Gly Ser Gly Ala Gly Ala Gly Ser Gly Ala Gly Ala Gly Ser
        3065               3070               3075

Gly Ala Gly Ala Gly Tyr Gly Ala Gly Val Gly Ala Gly Tyr Gly
        3080               3085               3090

Val Gly Tyr Gly Ala Gly Val Gly Ala Gly Tyr Gly Ala Gly Ala
        3095               3100               3105

Gly Ser Gly Ala Ala Ser Gly Ala Gly Ala Gly Ser Gly Ala Gly
        3110               3115               3120

Ala Gly Ala Gly Ser Gly Ala Gly Ala Gly Ser Gly Ala Gly Ala
        3125               3130               3135

Gly Ser Gly Ala Gly Ala Gly Ser Gly Ala Gly Ala Gly Ser Gly
        3140               3145               3150

Ala Gly Ala Gly Ser Gly Ala Gly Ala Gly Tyr Gly Ala Gly Tyr
        3155               3160               3165

Gly Ala Gly Val Gly Ala Gly Tyr Gly Ala Gly Ala Gly Val Gly
        3170               3175               3180

Tyr Gly Ala Gly Ala Gly Ala Gly Tyr Gly Ala Gly Ala Gly Ser
        3185               3190               3195

Gly Ala Ala Ser Gly Ala Gly Ala Gly Ala Gly Ser Gly Ala Gly
        3200               3205               3210

Ala Gly Thr Gly Ala Gly Ala Gly Ser Gly Ala Gly Ala Gly Tyr
        3215               3220               3225

Gly Ala Gly Ala Gly Ser Gly Ala Ala Ser Gly Ala Gly Ala Gly
        3230               3235               3240

Ala Gly Ala Gly Ala Gly Thr Gly Ser Ser Gly Phe Gly Pro Tyr
        3245               3250               3255

Val Ala Asn Gly Gly Tyr Ser Gly Tyr Glu Tyr Ala Trp Ser Ser
        3260               3265               3270

Glu Ser Asp Phe Gly Thr Gly Ser Gly Ala Gly Ala Gly Ser Gly
        3275               3280               3285

Ala Gly Ala Gly Ser Gly Ala Gly Ala Gly Ser Gly Ala Gly Ala
        3290               3295               3300
```

```
Gly Ser Gly Ala Gly Ala Gly Tyr Gly Ala Val Gly Ala Gly
    3305                3310                3315

Tyr Gly Ala Gly Ala Gly Ser Gly Ala Gly Ser Gly Ala Gly Ala
    3320                3325                3330

Gly Ser Gly Ala Gly Ala Gly Ser Gly Ala Gly Ala Gly Ser Gly
    3335                3340                3345

Ala Gly Ala Gly Ser Gly Ala Gly Ala Gly Tyr Gly Ala Gly Ala
    3350                3355                3360

Gly Ser Gly Thr Gly Ser Gly Ala Gly Ala Gly Ser Gly Ala Gly
    3365                3370                3375

Ala Gly Ser Gly Ala Gly Ala Gly Ser Gly Ala Gly Ala Gly Ser
    3380                3385                3390

Gly Ala Gly Ala Gly Ser Gly Ala Gly Ala Gly Ser Gly Val Gly
    3395                3400                3405

Ala Gly Tyr Gly Val Gly Tyr Gly Ala Gly Ala Gly Ala Gly Tyr
    3410                3415                3420

Gly Val Gly Tyr Gly Ala Gly Ala Gly Ala Gly Tyr Gly Ala Gly
    3425                3430                3435

Ala Gly Ser Gly Thr Gly Ser Gly Ala Gly Ala Gly Ser Gly Ala
    3440                3445                3450

Gly Ala Gly Ser Gly Ala Gly Ala Gly Ser Gly Ala Gly Ala Gly
    3455                3460                3465

Ser Gly Ala Gly Ala Gly Ser Gly Ala Gly Ala Gly Ser Gly Ala
    3470                3475                3480

Gly Ala Gly Tyr Gly Ala Gly Val Gly Ala Gly Tyr Gly Val Gly
    3485                3490                3495

Tyr Gly Ala Gly Ala Gly Ala Gly Tyr Gly Ala Gly Ala Gly Ser
    3500                3505                3510

Gly Ala Gly Ser Gly Ala Gly Ala Gly Ser Gly Ala Gly Ala Gly
    3515                3520                3525

Ser Gly Ala Gly Ala Gly Ser Gly Ala Gly Ala Gly Ser Gly Ala
    3530                3535                3540

Gly Ser Gly Ala Gly Ala Gly Ser Gly Ala Gly Ala Gly Ser Gly
    3545                3550                3555

Ala Gly Ala Gly Ser Gly Ala Gly Ser Gly Ala Gly Ala Gly Ser
    3560                3565                3570

Gly Ala Gly Ala Gly Tyr Gly Val Gly Tyr Gly Ala Gly Ala Gly
    3575                3580                3585

Ala Gly Tyr Gly Ala Gly Ala Gly Ser Gly Ala Gly Ser Gly Ala
    3590                3595                3600

Gly Ala Gly Ser Gly Ala Gly Ala Gly Ser Gly Ala Gly Ala Gly
    3605                3610                3615

Ser Gly Ala Gly Ser Gly Ala Gly Ala Gly Ser Gly Ala Gly Ala
    3620                3625                3630

Gly Ser Gly Ala Gly Ala Gly Ser Gly Ala Gly Ala Gly Tyr Gly
    3635                3640                3645

Ala Gly Val Gly Ala Gly Tyr Gly Val Gly Tyr Gly Ala Gly Ala
    3650                3655                3660

Gly Ala Gly Tyr Gly Ala Gly Ala Gly Ser Gly Ala Gly Ser Gly
    3665                3670                3675

Ala Gly Ala Gly Ser Gly Ala Gly Ala Gly Ser Gly Ala Gly Ala
    3680                3685                3690
```

```
Gly Ser Gly Ala Gly Ala Gly Ser Gly Ala Gly Ser Gly
    3695                3700                3705

Ala Gly Ala Gly Ser Gly Ala Gly Ser Gly Ala Gly Ser
    3710                3715                3720

Gly Ala Gly Ala Gly Ser Gly Ala Gly Ala Gly Ser Gly Ala Gly
    3725                3730                3735

Ala Gly Ser Gly Ala Gly Ala Gly Tyr Gly Ala Gly Val Gly Ala
    3740                3745                3750

Gly Tyr Gly Val Gly Tyr Gly Ala Gly Ala Gly Tyr Gly
    3755                3760                3765

Ala Gly Ala Gly Ser Gly Ala Ala Ser Gly Ala Gly Ala Gly Ala
    3770                3775                3780

Gly Ala Gly Ala Gly Thr Gly Ser Ser Gly Phe Gly Pro Tyr Val
    3785                3790                3795

Ala Asn Gly Gly Tyr Ser Gly Tyr Glu Tyr Ala Trp Ser Ser Glu
    3800                3805                3810

Ser Asp Phe Gly Thr Gly Ser Gly Ala Gly Ala Gly Ser Gly Ala
    3815                3820                3825

Gly Ala Gly Ser Gly Ala Gly Ala Gly Tyr Gly Ala Gly Tyr Gly
    3830                3835                3840

Ala Gly Val Gly Ala Gly Tyr Gly Ala Gly Ala Gly Val Gly Tyr
    3845                3850                3855

Gly Ala Gly Ala Gly Ala Gly Tyr Gly Ala Gly Ala Gly Ser Gly
    3860                3865                3870

Ala Ala Ser Gly Ala Gly Ala Gly Ala Gly Ala Gly Ala Gly Ser
    3875                3880                3885

Gly Ala Gly Ala Gly Ser Gly Ala Gly Ala Gly Ala Gly Ser Gly
    3890                3895                3900

Ala Gly Ala Gly Tyr Gly Ala Gly Tyr Gly Ile Gly Val Gly Ala
    3905                3910                3915

Gly Tyr Gly Ala Gly Ala Gly Val Gly Tyr Gly Ala Gly Ala Gly
    3920                3925                3930

Ala Gly Tyr Gly Ala Gly Ala Gly Ser Gly Ala Ala Ser Gly Ala
    3935                3940                3945

Gly Ala Gly Ser Gly Ala Gly Ala Gly Ser Gly Ala Gly Ala Gly
    3950                3955                3960

Ser Gly Ala Gly Ala Gly Ser Gly Ala Gly Ala Gly Ser Gly Ala
    3965                3970                3975

Gly Ala Gly Ser Gly Ala Gly Ala Gly Tyr Gly Ala Gly Tyr Gly
    3980                3985                3990

Ala Gly Val Gly Ala Gly Tyr Gly Ala Gly Ala Gly Val Gly Tyr
    3995                4000                4005

Gly Ala Gly Ala Gly Ala Gly Tyr Gly Ala Gly Ala Gly Ser Gly
    4010                4015                4020

Ala Ala Ser Gly Ala Gly Ala Gly Ala Gly Ala Gly Ala Gly Ala
    4025                4030                4035

Gly Ser Gly Ala Gly Ala Gly Ser Gly Ala Gly Ala Gly Ser Gly
    4040                4045                4050

Ala Gly Ala Gly Ser Gly Ala Gly Ala Gly Ser Gly Ala Gly Ala
    4055                4060                4065

Gly Ser Gly Ala Gly Ala Gly Ser Gly Ala Gly Ala Gly Ser Gly
    4070                4075                4080

Ala Gly Ala Gly Ser Gly Ala Gly Ala Gly Tyr Gly Ala Gly Val
```

-continued

```
                    4085                4090                4095
Gly Ala Gly Tyr Gly Ala Gly Tyr Gly Gly Ala Gly Ala Gly Tyr
        4100                4105                4110
Gly Ala Gly Ala Gly Ser Gly Ala Ala Ser Gly Ala Gly Ala Gly
        4115                4120                4125
Ser Gly Ala Gly Ala Gly Ser Gly Ala Gly Ala Gly Ser Gly Ala
        4130                4135                4140
Gly Ala Gly Ser Gly Ala Gly Ala Gly Ser Gly Ala Gly Ala Gly
        4145                4150                4155
Tyr Gly Ala Gly Ala Gly Ser Gly Ala Ala Ser Gly Ala Gly Ala
        4160                4165                4170
Gly Ala Gly Ala Gly Ala Gly Thr Gly Ser Ser Gly Phe Gly Pro
        4175                4180                4185
Tyr Val Asn Gly Gly Tyr Ser Gly Tyr Glu Tyr Ala Trp Ser Ser
        4190                4195                4200
Glu Ser Asp Phe Gly Thr Gly Ser Gly Ala Gly Ala Gly Ser Gly
        4205                4210                4215
Ala Gly Ala Gly Ser Gly Ala Gly Ala Gly Tyr Gly Ala Gly Val
        4220                4225                4230
Gly Ala Gly Tyr Gly Ala Gly Tyr Gly Ala Gly Ala Gly Ala Gly
        4235                4240                4245
Tyr Gly Ala Gly Ala Gly Ser Gly Ala Ala Ser Gly Ala Gly Ala
        4250                4255                4260
Gly Ser Gly Ala Gly Ala Gly Ser Gly Ala Gly Ala Gly Ser Gly
        4265                4270                4275
Ala Gly Ala Gly Ser Gly Ala Gly Ser Gly Ala Gly Ala Gly Ser
        4280                4285                4290
Gly Ala Gly Ala Gly Ser Gly Ala Gly Ala Gly Ser Gly Ala Gly
        4295                4300                4305
Ala Gly Ser Gly Ala Gly Ala Gly Ser Gly Ala Gly Ala Gly Tyr
        4310                4315                4320
Gly Ala Gly Val Gly Ala Gly Tyr Gly Ala Gly Tyr Gly Ala Gly
        4325                4330                4335
Ala Gly Ala Gly Tyr Gly Ala Gly Ala Gly Ser Gly Ala Ala Ser
        4340                4345                4350
Gly Ala Gly Ala Gly Ser Gly Ala Gly Ala Gly Ala Gly Ser Gly
        4355                4360                4365
Ala Gly Ala Gly Ser Gly Ala Gly Ala Gly Ser Gly Ala Gly Ala
        4370                4375                4380
Gly Ser Gly Ala Gly Ala Gly Ser Gly Ala Gly Ala Gly Ser Gly
        4385                4390                4395
Ala Gly Ser Gly Ala Gly Ala Gly Ser Gly Ala Gly Ala Gly Tyr
        4400                4405                4410
Gly Ala Gly Tyr Gly Ala Gly Val Gly Ala Gly Tyr Gly Ala Gly
        4415                4420                4425
Ala Gly Val Gly Tyr Gly Ala Gly Ala Gly Ala Gly Tyr Gly Ala
        4430                4435                4440
Gly Ala Gly Ser Gly Ala Ala Ser Gly Ala Gly Ala Gly Ser Gly
        4445                4450                4455
Ser Gly Ala Gly Ser Gly Ala Gly Ala Gly Ser Gly Ala Gly Ala
        4460                4465                4470
Gly Ser Gly Ala Gly Ala Gly Ala Gly Ser Gly Ala Gly Ala Gly
        4475                4480                4485
```

```
Ser Gly Ala Gly Ala Gly Ser Gly Ala Gly Ala Gly Tyr Gly Ala
    4490                4495                4500

Gly Tyr Gly Ala Gly Ala Gly Ser Gly Ala Ala Ser Gly Ala Gly
    4505                4510                4515

Ala Gly Ala Gly Ala Gly Ala Gly Thr Gly Ser Ser Gly Phe Gly
    4520                4525                4530

Pro Tyr Val Ala Asn Gly Tyr Ser Gly Tyr Glu Tyr Ala Trp
    4535                4540                4545

Ser Ser Glu Ser Asp Phe Gly Thr Gly Ser Gly Ala Gly Ala Gly
    4550                4555                4560

Ser Gly Ala Gly Ala Gly Ser Gly Ala Gly Ala Gly Tyr Gly Ala
    4565                4570                4575

Gly Val Gly Ala Gly Tyr Gly Ala Gly Tyr Gly Ala Gly Ala Gly
    4580                4585                4590

Ala Gly Tyr Gly Ala Gly Ala Gly Ser Gly Ala Gly Ser Gly Ala
    4595                4600                4605

Gly Ala Gly Ser Gly Ala Gly Ala Gly Ser Gly Ala Gly Ala Gly
    4610                4615                4620

Ser Gly Ala Gly Ala Gly Ser Gly Ala Gly Ala Gly Ser Gly Ala
    4625                4630                4635

Gly Ala Gly Ser Gly Ala Gly Ala Gly Ser Gly Ala Gly Ala Gly
    4640                4645                4650

Tyr Gly Ala Gly Tyr Gly Ala Gly Ala Gly Ala Gly Tyr Gly Ala
    4655                4660                4665

Gly Ala Gly Val Gly Tyr Gly Ala Gly Ala Gly Ala Gly Tyr Gly
    4670                4675                4680

Ala Gly Ala Gly Ser Gly Ala Gly Ser Gly Ala Gly Ala Gly Ser
    4685                4690                4695

Gly Ser Gly Ala Gly Ala Gly Ser Gly Ser Gly Ala Gly Ser Gly
    4700                4705                4710

Ala Gly Ala Gly Ser Gly Ala Gly Ala Gly Ser Gly Ala Gly Ala
    4715                4720                4725

Gly Ser Gly Ala Gly Ala Gly Ser Gly Ala Gly Ala Gly Ser Gly
    4730                4735                4740

Ala Gly Ala Gly Ser Gly Ala Gly Ala Gly Tyr Gly Ala Gly Tyr
    4745                4750                4755

Gly Ile Gly Val Gly Ala Gly Tyr Gly Ala Gly Ala Gly Val Gly
    4760                4765                4770

Tyr Gly Ala Gly Ala Gly Ala Gly Tyr Gly Ala Gly Ala Gly Ser
    4775                4780                4785

Gly Ala Ala Ser Gly Ala Gly Ala Gly Ser Gly Ala Gly Ala Gly
    4790                4795                4800

Ser Gly Ala Gly Ala Gly Ser Gly Ala Gly Ala Gly Ser Gly Ala
    4805                4810                4815

Gly Ala Gly Ser Gly Ala Gly Ala Gly Ser Gly Ala Gly Ala Gly
    4820                4825                4830

Ser Gly Ala Gly Ala Gly Ser Gly Ala Gly Ala Gly Ser Gly Ala
    4835                4840                4845

Gly Ala Gly Tyr Gly Ala Gly Ala Gly Val Gly Tyr Gly Ala Gly
    4850                4855                4860

Ala Gly Ser Gly Ala Ala Ser Gly Ala Gly Ala Gly Ser Gly Ala
    4865                4870                4875
```

```
Gly Ala Gly Ser Gly Ala Gly Ala Gly Ser Gly Ala Gly Ala Gly
    4880            4885                4890
Ser Gly Ala Gly Ala Gly Ser Gly Ala Gly Ala Gly Ser Gly Ala
    4895            4900                4905
Gly Ala Gly Ser Gly Ala Gly Ser Gly Ala Gly Ala Gly Ser Gly
    4910            4915                4920
Ala Gly Ala Gly Tyr Gly Ala Gly Tyr Gly Ala Gly Val Gly Ala
    4925            4930                4935
Gly Tyr Gly Ala Gly Ala Tyr Gly Ala Gly Tyr Gly Val Gly
    4940            4945                4950
Ala Gly Ala Gly Tyr Gly Ala Gly Ala Gly Ser Gly Ala Gly Ser
    4955            4960                4965
Gly Ala Gly Ala Gly Ser Gly Ala Gly Ala Gly Ser Gly Ala Gly
    4970            4975                4980
Ala Gly Ser Gly Ala Gly Ala Gly Ser Gly Ala Gly Ala Gly Ser
    4985            4990                4995
Gly Ala Gly Ser Gly Ala Gly Ala Gly Tyr Gly Ala Gly Ala Gly
    5000            5005                5010
Ala Gly Tyr Gly Ala Gly Ala Gly Ala Gly Tyr Gly Ala Gly Ala
    5015            5020                5025
Gly Ser Gly Ala Ala Ser Gly Ala Gly Ala Gly Ala Gly Ala Gly
    5030            5035                5040
Ser Gly Ala Gly Ala Gly Ser Gly Ala Gly Ala Gly Ser Gly Ala
    5045            5050                5055
Gly Ser Gly Ala Gly Ala Gly Ser Gly Ala Gly Ala Gly Tyr Gly
    5060            5065                5070
Ala Gly Ala Gly Ser Gly Ala Ala Ser Gly Ala Gly Ala Gly Ser
    5075            5080                5085
Gly Ala Gly Ala Gly Ala Gly Ala Gly Ala Gly Ala Gly Ser Gly
    5090            5095                5100
Ala Gly Ala Gly Ser Gly Ala Gly Ala Gly Tyr Gly Ala Gly Ala
    5105            5110                5115
Gly Ser Gly Ala Ala Ser Gly Ala Gly Ala Gly Ala Gly Ala Gly
    5120            5125                5130
Thr Gly Ser Ser Gly Phe Gly Pro Tyr Val Ala Asn Gly Gly Tyr
    5135            5140                5145
Ser Arg Arg Glu Gly Tyr Glu Tyr Ala Trp Ser Ser Lys Ser Asp
    5150            5155                5160
Phe Glu Thr Gly Ser Gly Ala Ala Ser Gly Ala Gly Ala Gly Ala
    5165            5170                5175
Gly Ser Gly Ala Gly Ala Gly Ser Gly Ala Gly Ala Gly Ser Gly
    5180            5185                5190
Ala Gly Ala Gly Ser Gly Ala Gly Ala Gly Gly Ser Val Ser Tyr
    5195            5200                5205
Gly Ala Gly Arg Gly Tyr Gly Gln Gly Ala Gly Ser Ala Ala Ser
    5210            5215                5220
Ser Val Ser Ser Ala Ser Ser Arg Ser Tyr Asp Tyr Ser Arg Arg
    5225            5230                5235
Asn Val Arg Lys Asn Cys Gly Ile Pro Arg Arg Gln Leu Val Val
    5240            5245                5250
Lys Phe Arg Ala Leu Pro Cys Val Asn Cys
    5255            5260
```